(12) United States Patent
Bonsignore et al.

(10) Patent No.: US 9,649,211 B2
(45) Date of Patent: May 16, 2017

(54) ALTERNATING CIRCUMFERENTIAL BRIDGE STENT DESIGN AND METHODS FOR USE THEREOF

(75) Inventors: Craig L. Bonsignore, Pleasanton, CA (US); Stephen J. Kleshinski, San Jose, CA (US); Andrea Seba Les, Menlo Park, CA (US)

(73) Assignee: Confluent Medical Technologies, Inc., Fremont, CA (US)

( * ) Notice: Subject to any disclaimer, the term of this patent is extended or adjusted under 35 U.S.C. 154(b) by 44 days.

(21) Appl. No.: 13/100,132

(22) Filed: May 3, 2011

(65) Prior Publication Data

US 2011/0230957 A1 Sep. 22, 2011

Related U.S. Application Data

(63) Continuation-in-part of application No. 12/939,894, filed on Nov. 4, 2010.
(Continued)

(51) Int. Cl.
*A61F 2/86* (2013.01)
*A61F 2/915* (2013.01)
(Continued)

(52) U.S. Cl.
CPC ........ *A61F 2/915* (2013.01); *A61F 2002/044* (2013.01); *A61F 2002/91558* (2013.01);
(Continued)

(58) Field of Classification Search
CPC .......... A61F 2/91558; A61F 2250/0036; A61F 2250/0018
(Continued)

(56) References Cited

U.S. PATENT DOCUMENTS 3,593,854 A 7/1971 Swank
3,659,593 A 5/1972 Vail
(Continued)

FOREIGN PATENT DOCUMENTS

EP 0362113 A1 4/1990
EP 0221570 B1 1/1991
(Continued)

OTHER PUBLICATIONS

Boston Scientific Corp.; UltraflexTM Tracheobronchial Stent System (product info.); retrieved from: <http://www.bostonscientific.com/templatedata/imports/collateral/PulmonaryEndoscopy/prospec_ultrfxtb_01_us.pdf>; 2 pgs.; ©2007 (year of publication is sufficiently earlier than the effective U.S. filed and any foreign priority date).
(Continued)

*Primary Examiner* — Brian Pellegrino
(74) *Attorney, Agent, or Firm* — Shay Glenn LLP

(57) ABSTRACT

A stent includes a first section and a second section. The second section is aligned with the first section along a longitudinal axis of the stent. Each section includes a plurality of expandable modules and a plurality of bridging modules. Each expandable module includes a plurality of strut elements that join together at a plurality of apices. Each bridging module includes bridging elements that connect an apex of a first module with an apex of a second module. The plurality of expandable modules or the plurality of bridging modules in the first section are more radially stiff than the plurality of expandable modules or the plurality of bridging modules in the second section such that at least a portion of the first section is configured to be placed in a region of a vein subjected to physiologic compression.

41 Claims, 34 Drawing Sheets

Related U.S. Application Data

(60) Provisional application No. 61/258,145, filed on Nov. 4, 2009, provisional application No. 61/290,836, filed on Dec. 29, 2009, provisional application No. 61/391,462, filed on Oct. 8, 2010.

(51) Int. Cl.
  *A61F 2/04* (2013.01)
  *A61M 1/36* (2006.01)

(52) U.S. Cl.
  CPC . *A61F 2230/008* (2013.01); *A61F 2230/0054* (2013.01); *A61F 2250/0018* (2013.01); *A61F 2250/0036* (2013.01); *A61F 2250/0039* (2013.01); *A61M 1/3655* (2013.01)

(58) Field of Classification Search
  USPC ............................. 623/1.15, 1.16, 1.18, 1.19
  See application file for complete search history.

(56) References Cited

U.S. PATENT DOCUMENTS

| | | |
|---|---|---|
| 3,765,536 A | 10/1973 | Rosenberg |
| 3,765,537 A | 10/1973 | Rosenberg |
| 3,788,328 A | 1/1974 | Alley et al. |
| 3,807,401 A | 4/1974 | Riggle et al. |
| 3,843,974 A | 10/1974 | Miller et al. |
| 3,874,388 A | 4/1975 | King et al. |
| 3,935,111 A | 1/1976 | Bentley |
| 3,952,747 A | 4/1976 | Kimmell, Jr. |
| 3,953,566 A | 4/1976 | Gore |
| 3,970,565 A | 7/1976 | Ahlstrand et al. |
| 4,007,743 A | 2/1977 | Blake |
| 4,014,318 A | 3/1977 | Dockum et al. |
| 4,016,884 A | 4/1977 | Kwan-Gett |
| 4,073,723 A | 2/1978 | Swank et al. |
| 4,101,984 A | 7/1978 | MacGregor |
| 4,115,277 A | 9/1978 | Swank |
| 4,157,965 A | 6/1979 | Raible |
| 4,303,530 A | 12/1981 | Shah et al. |
| 4,319,580 A | 3/1982 | Colley et al. |
| 4,353,996 A | 10/1982 | Marconi et al. |
| 4,374,669 A | 2/1983 | Mac Gregor |
| 4,425,908 A | 1/1984 | Simon |
| 4,444,198 A | 4/1984 | Petre |
| 4,447,227 A | 5/1984 | Kotsanis |
| 4,457,487 A | 7/1984 | Steigerwald |
| 4,494,531 A | 1/1985 | Gianturco |
| 4,523,592 A | 6/1985 | Daniel |
| 4,542,748 A | 9/1985 | Roy |
| 4,553,545 A | 11/1985 | Maass et al. |
| 4,565,823 A | 1/1986 | Ohata et al. |
| 4,586,501 A | 5/1986 | Claracq |
| 4,592,356 A | 6/1986 | Gutierrez |
| 4,616,656 A | 10/1986 | Nicholson et al. |
| 4,619,246 A | 10/1986 | Molgaard-Nielsen et al. |
| 4,627,836 A | 12/1986 | MacGregor |
| 4,642,089 A | 2/1987 | Zupkas et al. |
| 4,643,184 A | 2/1987 | Mobin-Uddin |
| 4,650,466 A | 3/1987 | Luther |
| 4,655,771 A | 4/1987 | Wallsten |
| 4,662,885 A | 5/1987 | DiPisa, Jr. |
| 4,664,682 A | 5/1987 | Monzen |
| 4,666,426 A | 5/1987 | Aigner |
| 4,666,543 A | 5/1987 | Kawano |
| 4,676,771 A | 6/1987 | Henke |
| 4,680,029 A | 7/1987 | Ranford et al. |
| 4,688,553 A | 8/1987 | Metals |
| 4,699,611 A | 10/1987 | Bowden |
| 4,722,724 A | 2/1988 | Schocket |
| 4,727,873 A | 3/1988 | Mobin-Uddin |
| 4,732,152 A | 3/1988 | Wallsten |
| 4,756,884 A | 7/1988 | Hillman et al. |
| 4,760,849 A | 8/1988 | Kropf |
| 4,774,949 A | 10/1988 | Fogarty |
| 4,781,177 A | 11/1988 | Lebigot |
| 4,790,329 A | 12/1988 | Simon |
| 4,793,348 A | 12/1988 | Palmaz |
| 4,795,446 A | 1/1989 | Fecht |
| 4,817,600 A | 4/1989 | Herms et al. |
| 4,826,478 A | 5/1989 | Schocket |
| 4,828,563 A | 5/1989 | Muller-Lierheim |
| 4,832,055 A | 5/1989 | Palestrant |
| 4,858,623 A | 8/1989 | Bradshaw et al. |
| 4,873,978 A | 10/1989 | Ginsburg |
| 4,899,543 A | 2/1990 | Romanelli et al. |
| 4,917,089 A | 4/1990 | Sideris |
| 4,923,464 A | 5/1990 | DiPisa, Jr. |
| 4,944,727 A | 7/1990 | McCoy |
| 4,946,457 A | 8/1990 | Elliott |
| 4,954,251 A | 9/1990 | Barnes et al. |
| 4,957,501 A | 9/1990 | Lahille et al. |
| 4,969,891 A | 11/1990 | Gewertz |
| 4,969,902 A | 11/1990 | Ravo |
| 4,986,279 A | 1/1991 | O'Neill |
| 4,990,156 A | 2/1991 | Lefebvre |
| 5,018,530 A | 5/1991 | Rank et al. |
| 5,059,205 A | 10/1991 | El-Nounou et al. |
| 5,071,407 A | 12/1991 | Termin et al. |
| 5,092,996 A | 3/1992 | Spielberg |
| 5,102,417 A | 4/1992 | Palmaz |
| 5,108,407 A | 4/1992 | Geremia et al. |
| 5,108,418 A | 4/1992 | Lefebvre |
| 5,108,419 A | 4/1992 | Reger et al. |
| 5,108,420 A | 4/1992 | Marks |
| 5,127,916 A | 7/1992 | Spencer et al. |
| 5,133,733 A | 7/1992 | Rasmussen et al. |
| 5,147,379 A | 9/1992 | Sabbaghian et al. |
| 5,151,105 A | 9/1992 | Kwan-Gett |
| 5,152,777 A | 10/1992 | Goldberg et al. |
| 5,158,533 A | 10/1992 | Strauss et al. |
| 5,158,565 A | 10/1992 | Marcadis et al. |
| 5,171,259 A | 12/1992 | Inoue |
| 5,190,657 A | 3/1993 | Heagle et al. |
| 5,192,286 A | 3/1993 | Phan et al. |
| 5,192,301 A | 3/1993 | Kamiya et al. |
| 5,195,984 A | 3/1993 | Schatz |
| 5,197,978 A | 3/1993 | Hess |
| 5,201,757 A | 4/1993 | Heyn et al. |
| 5,234,458 A | 8/1993 | Metais |
| 5,257,621 A | 11/1993 | Bardy et al. |
| 5,269,924 A | 12/1993 | Rochat |
| 5,273,517 A | 12/1993 | Barone et al. |
| 5,275,622 A | 1/1994 | Lazarus et al. |
| 5,282,823 A | 2/1994 | Schwartz et al. |
| 5,284,488 A | 2/1994 | Sideris |
| 5,292,321 A | 3/1994 | Lee |
| 5,300,086 A | 4/1994 | Gory et al. |
| 5,311,908 A | 5/1994 | Barone et al. |
| 5,334,217 A | 8/1994 | Das |
| 5,344,427 A | 9/1994 | Cottenceau et al. |
| 5,350,398 A | 9/1994 | Pavcnik et al. |
| 5,354,317 A | 10/1994 | Alt |
| 5,356,432 A | 10/1994 | Rutkow et al. |
| 5,366,504 A | 11/1994 | Andersen et al. |
| 5,370,657 A | 12/1994 | Irie |
| 5,375,612 A | 12/1994 | Cottenceau et al. |
| 5,383,887 A | 1/1995 | Nadal |
| 5,413,586 A | 5/1995 | Dibie et al. |
| 5,415,630 A | 5/1995 | Gory et al. |
| 5,421,832 A | 6/1995 | Lefebvre |
| 5,423,851 A | 6/1995 | Samuels |
| 5,425,744 A | 6/1995 | Fagan et al. |
| 5,433,727 A | 7/1995 | Sideris |
| 5,443,500 A | 8/1995 | Sigwart |
| 5,449,373 A | 9/1995 | Pinchasik et al. |
| 5,449,382 A | 9/1995 | Dayton |
| 5,451,233 A | 9/1995 | Yock |
| 5,451,235 A | 9/1995 | Lock et al. |
| 5,464,449 A | 11/1995 | Ryan et al. |
| 5,466,216 A | 11/1995 | Brown et al. |
| 5,480,423 A | 1/1996 | Ravenscroft et al. |
| 5,484,424 A | 1/1996 | Cottenceau et al. |

(56) References Cited

U.S. PATENT DOCUMENTS

| | | |
|---|---|---|
| 5,486,193 A | 1/1996 | Bourne et al. |
| 5,503,801 A | 4/1996 | Brugger |
| 5,507,811 A | 4/1996 | Koike et al. |
| 5,522,881 A | 6/1996 | Lentz |
| 5,527,338 A | 6/1996 | Purdy |
| 5,531,788 A | 7/1996 | Dibie et al. |
| 5,545,206 A | 8/1996 | Carson |
| 5,545,210 A | 8/1996 | Hess et al. |
| 5,549,626 A | 8/1996 | Miller et al. |
| 5,554,182 A | 9/1996 | Dinh et al. |
| 5,562,698 A | 10/1996 | Parker |
| 5,569,273 A | 10/1996 | Titone et al. |
| 5,571,166 A | 11/1996 | Dinh et al. |
| 5,578,045 A | 11/1996 | Das |
| 5,591,197 A | 1/1997 | Orth et al. |
| 5,591,224 A | 1/1997 | Schwartz et al. |
| 5,591,227 A | 1/1997 | Dinh et al. |
| 5,591,251 A | 1/1997 | Brugger |
| 5,593,441 A | 1/1997 | Lichtenstein et al. |
| 5,595,909 A | 1/1997 | Hu et al. |
| 5,599,352 A | 2/1997 | Dinh et al. |
| 5,601,595 A | 2/1997 | Smith |
| 5,603,698 A | 2/1997 | Roberts et al. |
| 5,617,854 A | 4/1997 | Munsif |
| 5,626,599 A | 5/1997 | Bourne et al. |
| 5,626,605 A | 5/1997 | Irie et al. |
| 5,632,734 A | 5/1997 | Galel et al. |
| 5,634,474 A | 6/1997 | Grippi |
| 5,634,936 A | 6/1997 | Linden et al. |
| 5,634,942 A | 6/1997 | Chevillon et al. |
| 5,636,644 A | 6/1997 | Hart et al. |
| 5,637,097 A | 6/1997 | Yoon |
| 5,643,320 A | 7/1997 | Lower et al. |
| 5,643,321 A | 7/1997 | McDevitt |
| 5,649,949 A | 7/1997 | Wallace et al. |
| 5,649,950 A | 7/1997 | Bourne et al. |
| 5,653,747 A | 8/1997 | Dereume et al. |
| 5,653,755 A | 8/1997 | Ledergerber |
| 5,669,932 A | 9/1997 | Fischell et al. |
| 5,669,933 A | 9/1997 | Simon et al. |
| 5,672,585 A | 9/1997 | Pierschbacher et al. |
| 5,681,347 A | 10/1997 | Cathcart et al. |
| 5,693,085 A | 12/1997 | Buirge et al. |
| 5,695,518 A | 12/1997 | Laerum |
| 5,695,519 A | 12/1997 | Summers et al. |
| 5,702,421 A | 12/1997 | Schneidt |
| 5,704,910 A | 1/1998 | Humes |
| 5,709,704 A | 1/1998 | Nott et al. |
| 5,709,707 A | 1/1998 | Lock et al. |
| 5,713,853 A | 2/1998 | Clark et al. |
| 5,713,879 A | 2/1998 | Schneider |
| 5,713,921 A | 2/1998 | Bonutti |
| 5,716,408 A | 2/1998 | Eldridge et al. |
| 5,718,717 A | 2/1998 | Bonutti |
| 5,720,764 A | 2/1998 | Naderlinger |
| 5,722,964 A | 3/1998 | Herweck et al. |
| 5,725,552 A | 3/1998 | Kotula et al. |
| 5,728,133 A | 3/1998 | Kontos |
| 5,733,294 A | 3/1998 | Forber et al. |
| 5,733,303 A | 3/1998 | Israel et al. |
| 5,733,325 A | 3/1998 | Robinson et al. |
| 5,735,892 A | 4/1998 | Myers et al. |
| 5,741,297 A | 4/1998 | Simon |
| 5,743,873 A | 4/1998 | Cai et al. |
| 5,755,663 A | 5/1998 | Larsen et al. |
| 5,755,776 A | 5/1998 | Al Saadon |
| 5,755,778 A | 5/1998 | Kleshinski |
| 5,755,781 A | 5/1998 | Jayaraman |
| 5,755,790 A | 5/1998 | Chevillon et al. |
| 5,766,246 A | 6/1998 | Mulhauser et al. |
| 5,772,668 A | 6/1998 | Summers et al. |
| 5,776,142 A | 7/1998 | Gunderson |
| 5,788,661 A | 8/1998 | Japuntich |
| 5,792,179 A | 8/1998 | Sideris |
| 5,795,322 A | 8/1998 | Boudewijn |
| 5,795,325 A | 8/1998 | Valley et al. |
| 5,795,335 A | 8/1998 | Zinreich |
| 5,799,350 A | 9/1998 | Ferek-Petric et al. |
| 5,800,457 A | 9/1998 | Gelbfish |
| 5,800,507 A | 9/1998 | Schwartz |
| 5,800,522 A | 9/1998 | Campbell et al. |
| 5,810,872 A | 9/1998 | Kanesaka et al. |
| 5,824,034 A | 10/1998 | Schmitt et al. |
| 5,827,229 A | 10/1998 | Auth et al. |
| 5,830,224 A | 11/1998 | Cohn et al. |
| 5,836,962 A | 11/1998 | Gianotti |
| 5,836,964 A | 11/1998 | Richter et al. |
| 5,836,969 A | 11/1998 | Kim et al. |
| 5,843,167 A | 12/1998 | Dwyer et al. |
| 5,843,171 A | 12/1998 | Campbell et al. |
| 5,843,176 A | 12/1998 | Weier |
| 5,846,261 A | 12/1998 | Kotula et al. |
| 5,849,004 A | 12/1998 | Bramlet |
| 5,849,034 A | 12/1998 | Schwartz |
| 5,853,420 A | 12/1998 | Chevillon et al. |
| 5,853,422 A | 12/1998 | Huebsch et al. |
| 5,860,998 A | 1/1999 | Robinson et al. |
| 5,861,003 A | 1/1999 | Latson et al. |
| 5,871,693 A | 2/1999 | Lindsay |
| 5,873,906 A | 2/1999 | Lau et al. |
| 5,873,907 A | 2/1999 | Frantzen |
| 5,876,432 A | 3/1999 | Lau et al. |
| 5,879,366 A | 3/1999 | Shaw et al. |
| 5,882,340 A | 3/1999 | Yoon |
| 5,882,351 A | 3/1999 | Fox |
| 5,893,869 A | 4/1999 | Barnhart et al. |
| 5,893,887 A | 4/1999 | Jayaraman |
| 5,895,398 A | 4/1999 | Wensel et al. |
| 5,902,333 A | 5/1999 | Roberts et al. |
| 5,904,703 A | 5/1999 | Gilson |
| 5,907,893 A | 6/1999 | Zadno-Azizi et al. |
| 5,908,447 A | 6/1999 | Schroeppel et al. |
| 5,910,129 A | 6/1999 | Koblish et al. |
| 5,925,061 A | 7/1999 | Ogi et al. |
| 5,925,074 A | 7/1999 | Gingras et al. |
| 5,928,261 A | 7/1999 | Ruiz |
| 5,928,269 A | 7/1999 | Alt |
| 5,938,683 A | 8/1999 | Lefebvre |
| 5,941,896 A | 8/1999 | Kerr |
| 5,947,995 A | 9/1999 | Samuels et al. |
| 5,954,741 A | 9/1999 | Fox |
| 5,954,743 A | 9/1999 | Jang |
| 5,954,767 A | 9/1999 | Pajotin et al. |
| 5,957,940 A | 9/1999 | Tanner et al. |
| 5,957,977 A | 9/1999 | Melvin |
| 5,965,089 A | 10/1999 | Jarvik et al. |
| 5,967,976 A | 10/1999 | Larsen et al. |
| 5,968,053 A | 10/1999 | Revelas |
| 5,968,071 A | 10/1999 | Chevillon et al. |
| 5,976,172 A | 11/1999 | Homsma et al. |
| 5,980,558 A | 11/1999 | Wiley |
| 5,980,564 A | 11/1999 | Stinson |
| 5,984,917 A | 11/1999 | Fleischman et al. |
| 5,984,947 A | 11/1999 | Smith |
| 5,991,657 A | 11/1999 | Kim |
| 6,001,118 A | 12/1999 | Daniel et al. |
| 6,007,558 A | 12/1999 | Ravenscroft et al. |
| 6,013,093 A | 1/2000 | Nott et al. |
| 6,024,096 A | 2/2000 | Buckberg |
| 6,024,756 A | 2/2000 | Huebsch et al. |
| 6,042,597 A | 3/2000 | Kveen et al. |
| 6,046,381 A | 4/2000 | Mucke et al. |
| 6,048,329 A | 4/2000 | Thompson et al. |
| 6,051,014 A | 4/2000 | Jang |
| 6,053,932 A | 4/2000 | Daniel et al. |
| 6,059,825 A | 5/2000 | Hobbs et al. |
| 6,068,645 A | 5/2000 | Tu |
| 6,071,279 A | 6/2000 | Whayne et al. |
| 6,077,281 A | 6/2000 | Das |
| 6,077,291 A | 6/2000 | Das |
| 6,080,178 A | 6/2000 | Meglin |
| 6,080,182 A | 6/2000 | Shaw et al. |
| 6,090,096 A | 7/2000 | St. Goar et al. |
| 6,090,097 A | 7/2000 | Barbut et al. |

(56) References Cited

U.S. PATENT DOCUMENTS

| | | |
|---|---|---|
| 6,090,127 A | 7/2000 | Globerman |
| 6,099,493 A | 8/2000 | Swisher |
| 6,099,549 A | 8/2000 | Bosma et al. |
| 6,117,105 A | 9/2000 | Bresnaham et al. |
| 6,120,539 A | 9/2000 | Eldridge et al. |
| 6,123,715 A | 9/2000 | Amplatz |
| 6,123,723 A | 9/2000 | Konya et al. |
| 6,129,755 A | 10/2000 | Mathis et al. |
| 6,142,987 A | 11/2000 | Tsugita |
| 6,146,404 A | 11/2000 | Kim et al. |
| 6,152,946 A | 11/2000 | Broome et al. |
| 6,171,328 B1 | 1/2001 | Addis |
| 6,171,329 B1 | 1/2001 | Shaw et al. |
| 6,174,322 B1 | 1/2001 | Schneidt |
| 6,193,745 B1 | 2/2001 | Fogarty et al. |
| 6,200,276 B1 | 3/2001 | Biesel et al. |
| 6,206,888 B1 | 3/2001 | Bicek et al. |
| 6,214,020 B1 | 4/2001 | Mulhauser et al. |
| 6,214,025 B1 | 4/2001 | Thistle et al. |
| 6,214,029 B1 | 4/2001 | Thill et al. |
| 6,217,600 B1 | 4/2001 | DiMatteo |
| 6,221,092 B1 | 4/2001 | Koike et al. |
| 6,231,581 B1 | 5/2001 | Shank et al. |
| 6,231,589 B1 | 5/2001 | Wessman et al. |
| 6,234,995 B1 | 5/2001 | Peacock, III |
| 6,235,044 B1 | 5/2001 | Root et al. |
| 6,238,416 B1 | 5/2001 | Sideris |
| 6,241,727 B1 | 6/2001 | Tu et al. |
| 6,241,738 B1 | 6/2001 | Dereume et al. |
| 6,241,757 B1 | 6/2001 | An et al. |
| 6,245,012 B1 | 6/2001 | Kleshinski |
| 6,245,103 B1 | 6/2001 | Stinson |
| 6,251,122 B1 | 6/2001 | Tsukernik |
| 6,254,612 B1 | 7/2001 | Hieshima |
| 6,258,026 B1 | 7/2001 | Ravenscroft et al. |
| 6,258,124 B1 | 7/2001 | Darois et al. |
| 6,261,318 B1 | 7/2001 | Lee et al. |
| 6,264,654 B1 | 7/2001 | Swartz et al. |
| 6,264,690 B1 | 7/2001 | Von Oepen |
| 6,267,747 B1 | 7/2001 | Samson et al. |
| 6,267,772 B1 | 7/2001 | Mulhauser et al. |
| 6,267,776 B1 | 7/2001 | O'Connell |
| 6,267,777 B1 | 7/2001 | Bosma et al. |
| 6,270,515 B1 | 8/2001 | Linden et al. |
| 6,273,901 B1 | 8/2001 | Whitcher et al. |
| 6,277,139 B1 | 8/2001 | Levinson et al. |
| 6,280,413 B1 | 8/2001 | Clark et al. |
| 6,287,335 B1 | 9/2001 | Drasler et al. |
| 6,311,692 B1 | 11/2001 | Vaska et al. |
| 6,325,815 B1 | 12/2001 | Kusleika et al. |
| 6,328,755 B1 | 12/2001 | Marshall |
| 6,331,183 B1 | 12/2001 | Suon |
| 6,334,864 B1 | 1/2002 | Amplatz et al. |
| 6,336,938 B1 | 1/2002 | Kavteladze et al. |
| 6,340,364 B2 | 1/2002 | Kanesaka |
| 6,342,062 B1 | 1/2002 | Suon et al. |
| 6,342,063 B1 | 1/2002 | DeVries et al. |
| 6,344,053 B1 | 2/2002 | Boneau |
| 6,352,552 B1 | 3/2002 | Levinson et al. |
| 6,355,052 B1 | 3/2002 | Neuss et al. |
| 6,358,230 B1 | 3/2002 | Davey |
| 6,361,545 B1 | 3/2002 | Macoviak et al. |
| 6,361,546 B1 | 3/2002 | Khosravi |
| 6,371,969 B1 | 4/2002 | Tsugita et al. |
| 6,371,971 B1 | 4/2002 | Tsugita et al. |
| 6,379,368 B1 | 4/2002 | Corcoran et al. |
| 6,391,044 B1 | 5/2002 | Yadav et al. |
| 6,398,792 B1 | 6/2002 | O'Connor |
| 6,402,736 B1 | 6/2002 | Brown et al. |
| 6,416,293 B1 | 7/2002 | Bouchard et al. |
| 6,422,397 B1 | 7/2002 | Lynn et al. |
| 6,428,559 B1 | 8/2002 | Johnson |
| 6,436,112 B2 | 8/2002 | Wensel et al. |
| 6,436,120 B1 | 8/2002 | Meglin |
| 6,436,121 B1 | 8/2002 | Blom |
| 6,440,077 B1 | 8/2002 | Jung et al. |
| 6,440,152 B1 | 8/2002 | Gainor et al. |
| 6,443,972 B1 | 9/2002 | Bosma et al. |
| 6,447,530 B1 | 9/2002 | Ostrovsky et al. |
| 6,451,257 B1 | 9/2002 | Flamer |
| 6,454,775 B1 | 9/2002 | Demarais et al. |
| 6,461,370 B1 | 10/2002 | Gray et al. |
| 6,468,299 B2 | 10/2002 | Stack et al. |
| 6,468,303 B1 | 10/2002 | Amplatz et al. |
| 6,482,222 B1 | 11/2002 | Bruckheimer et al. |
| 6,485,497 B2 | 11/2002 | Wensel et al. |
| 6,485,502 B2 | 11/2002 | Don Michael et al. |
| 6,488,692 B1 | 12/2002 | Spence et al. |
| 6,491,712 B1 | 12/2002 | O'Connor |
| 6,497,709 B1 | 12/2002 | Heath |
| 6,506,204 B2 | 1/2003 | Mazzocchi |
| 6,506,205 B2 | 1/2003 | Goldberg et al. |
| 6,506,408 B1 | 1/2003 | Palasis |
| 6,508,777 B1 | 1/2003 | Macoviak et al. |
| 6,508,782 B1 | 1/2003 | Evans et al. |
| 6,508,833 B2 | 1/2003 | Pavcnik et al. |
| 6,517,559 B1 | 2/2003 | O'Connell |
| 6,517,573 B1 | 2/2003 | Pollock et al. |
| 6,527,962 B1 | 3/2003 | Nadal |
| 6,533,805 B1 | 3/2003 | Jervis |
| 6,534,035 B1 | 3/2003 | Reed |
| 6,537,300 B2 | 3/2003 | Girton |
| 6,540,767 B1 | 4/2003 | Walak et al. |
| 6,540,768 B1 | 4/2003 | Diaz et al. |
| 6,544,167 B2 | 4/2003 | Buckberg et al. |
| 6,544,279 B1 | 4/2003 | Hopkins et al. |
| 6,544,280 B1 | 4/2003 | Daniel et al. |
| 6,547,754 B1 | 4/2003 | Evans et al. |
| 6,551,303 B1 | 4/2003 | Van Tassel et al. |
| 6,551,344 B2 | 4/2003 | Thill |
| 6,562,064 B1 | 5/2003 | deBeer |
| 6,562,071 B2 | 5/2003 | Jarvinen |
| 6,576,001 B2 | 6/2003 | Werneth et al. |
| 6,579,308 B1 | 6/2003 | Jansen et al. |
| 6,582,447 B1 | 6/2003 | Patel et al. |
| 6,585,689 B1 | 7/2003 | Macoviak et al. |
| 6,585,756 B1 | 7/2003 | Strecker |
| 6,585,758 B1 | 7/2003 | Chouinard et al. |
| 6,592,546 B1 | 7/2003 | Barbut et al. |
| 6,596,011 B2 | 7/2003 | Johnson et al. |
| 6,596,013 B2 | 7/2003 | Yang et al. |
| 6,599,314 B2 | 7/2003 | Mathis |
| 6,602,272 B2 | 8/2003 | Boylan et al. |
| 6,602,281 B1 | 8/2003 | Klein |
| 6,605,074 B2 | 8/2003 | Zadno-Azizi et al. |
| 6,605,102 B1 | 8/2003 | Mazzocchi et al. |
| 6,605,110 B2 | 8/2003 | Harrison |
| 6,610,006 B1 | 8/2003 | Amid et al. |
| 6,610,085 B1 | 8/2003 | Lazarus |
| 6,613,076 B1 | 9/2003 | Cherif-Cheikh |
| 6,616,679 B1 | 9/2003 | Khosravi et al. |
| 6,616,680 B1 | 9/2003 | Thielen |
| 6,616,681 B2 | 9/2003 | Hanson et al. |
| 6,616,684 B1 | 9/2003 | Vidlund et al. |
| 6,623,448 B2 | 9/2003 | Slater |
| 6,623,506 B2 | 9/2003 | McGuckin, Jr. et al. |
| 6,623,507 B2 | 9/2003 | Saleh |
| 6,626,899 B2 | 9/2003 | Houser et al. |
| 6,626,937 B1 | 9/2003 | Cox |
| 6,635,070 B2 | 10/2003 | Leeflang et al. |
| 6,638,259 B1 | 10/2003 | Palasis et al. |
| 6,645,143 B2 | 11/2003 | VanTassel et al. |
| 6,645,152 B1 | 11/2003 | Jung et al. |
| 6,645,202 B1 | 11/2003 | Pless et al. |
| 6,645,225 B1 | 11/2003 | Atkinson |
| 6,652,554 B1 | 11/2003 | Wholey et al. |
| 6,652,555 B1 | 11/2003 | VanTassel et al. |
| 6,652,556 B1 | 11/2003 | VanTassel et al. |
| 6,656,203 B2 | 12/2003 | Roth et al. |
| 6,656,206 B2 | 12/2003 | Corcoran et al. |
| 6,656,220 B1 | 12/2003 | Gomez et al. |
| 6,656,221 B2 | 12/2003 | Taylor et al. |
| 6,660,021 B1 | 12/2003 | Palmer et al. |
| 6,660,031 B2 | 12/2003 | Tran et al. |

(56) References Cited

U.S. PATENT DOCUMENTS

| | | | |
|---|---|---|---|
| 6,663,606 B1 | 12/2003 | Barry et al. |
| 6,663,651 B2 | 12/2003 | Krolik et al. |
| 6,669,708 B1 | 12/2003 | Nissenbaum et al. |
| 6,673,102 B1 | 1/2004 | Vonesh et al. |
| 6,676,666 B2 | 1/2004 | Vrba et al. |
| 6,676,682 B1 | 1/2004 | Tsugita et al. |
| 6,682,505 B2 | 1/2004 | Bates et al. |
| 6,682,554 B2 * | 1/2004 | Oepen et al. | 623/1.15 |
| 6,685,738 B2 | 2/2004 | Chouinard et al. |
| 6,689,150 B1 | 2/2004 | VanTassel et al. |
| 6,692,459 B2 | 2/2004 | Teitelbaum |
| 6,692,508 B2 | 2/2004 | Wensel et al. |
| 6,692,509 B2 | 2/2004 | Wensel et al. |
| 6,694,983 B2 | 2/2004 | Wolf et al. |
| 6,695,858 B1 | 2/2004 | Dubrul et al. |
| 6,695,864 B2 | 2/2004 | Macoviak et al. |
| 6,699,278 B2 | 3/2004 | Fischell et al. |
| 6,702,835 B2 | 3/2004 | Ginn |
| 6,706,065 B2 | 3/2004 | Langberg et al. |
| 6,709,442 B2 | 3/2004 | Miller et al. |
| 6,712,834 B2 | 3/2004 | Yassour et al. |
| 6,712,835 B2 | 3/2004 | Mazzocchi et al. |
| 6,712,836 B1 | 3/2004 | Berg et al. |
| 6,716,238 B2 | 4/2004 | Elliott |
| 6,723,133 B1 | 4/2004 | Pajotin |
| 6,726,701 B2 | 4/2004 | Gilson et al. |
| 6,726,703 B2 | 4/2004 | Broome et al. |
| 6,731,982 B1 | 5/2004 | Kroll et al. |
| 6,736,823 B2 | 5/2004 | Darois et al. |
| 6,736,839 B2 | 5/2004 | Cummings |
| 6,736,854 B2 | 5/2004 | Vadurro et al. |
| 6,740,061 B1 | 5/2004 | Oslund et al. |
| 6,740,094 B2 | 5/2004 | Maitland et al. |
| 6,740,112 B2 | 5/2004 | Yodfat et al. |
| 6,740,122 B1 | 5/2004 | Pajotin |
| 6,749,629 B1 | 6/2004 | Hong et al. |
| 6,752,825 B2 | 6/2004 | Eskuri |
| 6,754,528 B2 | 6/2004 | Bardy et al. |
| 6,754,531 B1 | 6/2004 | Kroll et al. |
| 6,755,846 B1 | 6/2004 | Yadav |
| 6,755,847 B2 | 6/2004 | Eskuri |
| 6,756,094 B1 | 6/2004 | Wang et al. |
| 6,758,830 B1 | 7/2004 | Schaer et al. |
| 6,761,731 B2 | 7/2004 | Majercak |
| 6,764,510 B2 | 7/2004 | Vidlund et al. |
| 6,766,196 B1 | 7/2004 | Kroll et al. |
| 6,776,770 B1 | 8/2004 | Trerotola |
| 6,776,784 B2 | 8/2004 | Ginn |
| 6,776,793 B2 | 8/2004 | Brown et al. |
| 6,780,183 B2 | 8/2004 | Jimenez, Jr. et al. |
| 6,783,499 B2 | 8/2004 | Schwartz |
| 6,783,538 B2 | 8/2004 | McGuckin, Jr. et al. |
| 6,790,213 B2 | 9/2004 | Cherok et al. |
| 6,790,218 B2 | 9/2004 | Jayaraman |
| 6,790,230 B2 | 9/2004 | Beyersdorf et al. |
| 6,790,231 B2 | 9/2004 | Liddicoat et al. |
| 6,793,666 B2 | 9/2004 | Hansen et al. |
| 6,795,731 B1 | 9/2004 | Kroll et al. |
| 6,797,083 B2 | 9/2004 | Peterson |
| 6,799,357 B2 | 10/2004 | Webb et al. |
| 6,805,128 B1 | 10/2004 | Pless et al. |
| 6,805,129 B1 | 10/2004 | Pless et al. |
| 6,805,711 B2 | 10/2004 | Quijano et al. |
| 6,808,537 B2 | 10/2004 | Michelson |
| 6,827,731 B2 | 12/2004 | Armstrong et al. |
| 6,835,378 B2 | 12/2004 | Davis et al. |
| 6,840,950 B2 | 1/2005 | Stanford et al. |
| 6,843,798 B2 | 1/2005 | Kusleika et al. |
| 6,849,084 B2 | 2/2005 | Rabkin et al. |
| 6,866,662 B2 | 3/2005 | Fuimaono et al. |
| 6,866,680 B2 | 3/2005 | Yassour et al. |
| 6,878,162 B2 | 4/2005 | Bales et al. |
| 6,881,218 B2 | 4/2005 | Beyer et al. |
| 6,887,214 B1 | 5/2005 | Levin et al. |
| 6,887,257 B2 | 5/2005 | Salahieh et al. |
| 6,887,268 B2 | 5/2005 | Butaric et al. |
| 6,890,353 B2 | 5/2005 | Cohn et al. |
| 6,895,265 B2 | 5/2005 | Silver |
| 6,899,727 B2 | 5/2005 | Armstrong et al. |
| 6,902,572 B2 | 6/2005 | Beulke et al. |
| 6,905,479 B1 | 6/2005 | Bouchard et al. |
| 6,907,286 B1 | 6/2005 | Kroll et al. |
| 6,911,037 B2 | 6/2005 | Gainor et al. |
| 6,913,614 B2 | 7/2005 | Marino et al. |
| 6,929,633 B2 | 8/2005 | Evans et al. |
| 6,929,660 B1 | 8/2005 | Ainsworth et al. |
| 6,931,280 B1 | 8/2005 | Yang |
| 6,939,361 B1 | 9/2005 | Kleshinski |
| 6,942,635 B2 | 9/2005 | Rosenblatt et al. |
| 6,951,570 B2 | 10/2005 | Linder et al. |
| 6,955,688 B2 | 10/2005 | Wilson et al. |
| 6,962,598 B2 | 11/2005 | Linder et al. |
| 6,966,886 B2 | 11/2005 | Appling |
| 6,972,025 B2 | 12/2005 | WasDyke |
| 6,974,469 B2 | 12/2005 | Broome et al. |
| 6,976,967 B2 | 12/2005 | Dahl et al. |
| 6,988,983 B2 | 1/2006 | Connors et al. |
| 6,989,021 B2 | 1/2006 | Bosma et al. |
| 6,994,718 B2 | 2/2006 | Groothuis et al. |
| 6,997,938 B2 | 2/2006 | Wang et al. |
| 6,997,939 B2 | 2/2006 | Linder et al. |
| 7,001,406 B2 | 2/2006 | Eskuri et al. |
| 7,004,964 B2 | 2/2006 | Thompson et al. |
| 7,011,671 B2 | 3/2006 | Welch |
| 7,012,106 B2 | 3/2006 | Yuan et al. |
| 7,014,765 B2 | 3/2006 | Dannenmaier |
| 7,052,487 B2 | 5/2006 | Cohn et al. |
| 7,052,500 B2 | 5/2006 | Bashiri et al. |
| 7,052,511 B2 | 5/2006 | Weldon et al. |
| 7,056,286 B2 | 6/2006 | Ravenscroft et al. |
| 7,056,336 B2 | 6/2006 | Armstrong et al. |
| 7,060,082 B2 | 6/2006 | Goll et al. |
| 7,063,682 B1 | 6/2006 | Whayne et al. |
| 7,066,951 B2 | 6/2006 | Chobotov |
| 7,083,633 B2 | 8/2006 | Morrill et al. |
| 7,087,069 B2 | 8/2006 | Petrovic et al. |
| 7,094,249 B1 | 8/2006 | Broome et al. |
| 7,112,219 B2 | 9/2006 | Vidlund et al. |
| 7,122,034 B2 | 10/2006 | Belhe et al. |
| 7,122,049 B2 | 10/2006 | Banas et al. |
| 7,125,420 B2 | 10/2006 | Rourke et al. |
| 7,131,966 B1 | 11/2006 | Tamari |
| 7,131,993 B2 | 11/2006 | Gregorich |
| 7,137,991 B2 | 11/2006 | Fedie |
| 7,137,993 B2 | 11/2006 | Acosta et al. |
| 7,147,649 B2 | 12/2006 | Thomas |
| 7,149,587 B2 | 12/2006 | Wardle et al. |
| 7,152,452 B2 | 12/2006 | Kokish |
| 7,163,553 B2 * | 1/2007 | Limon | 623/1.15 |
| 7,169,165 B2 | 1/2007 | Belef et al. |
| 7,179,274 B2 | 2/2007 | Bruckheimer et al. |
| 7,179,275 B2 | 2/2007 | McGuckin, Jr. et al. |
| 7,179,291 B2 | 2/2007 | Rourke et al. |
| 7,181,261 B2 | 2/2007 | Silver et al. |
| 7,186,262 B2 | 3/2007 | Saadat |
| 7,186,264 B2 | 3/2007 | Liddicoat et al. |
| 7,189,203 B2 | 3/2007 | Lau et al. |
| 7,192,434 B2 | 3/2007 | Anderson et al. |
| 7,209,783 B2 | 4/2007 | Fellows et al. |
| 7,214,237 B2 | 5/2007 | Don Michael et al. |
| 7,220,271 B2 | 5/2007 | Clubb et al. |
| 7,226,464 B2 | 6/2007 | Garner et al. |
| 7,229,462 B2 | 6/2007 | Sutton et al. |
| 7,229,469 B1 | 6/2007 | Witzel et al. |
| 7,231,260 B2 | 6/2007 | Wallace et al. |
| 7,232,453 B2 | 6/2007 | Shimon |
| 7,241,257 B1 | 7/2007 | Ainsworth et al. |
| 7,241,310 B1 | 7/2007 | Taylor et al. |
| 7,250,049 B2 | 7/2007 | Roop et al. |
| 7,252,679 B2 | 8/2007 | Fischell et al. |
| 7,258,697 B1 | 8/2007 | Cox et al. |
| 7,285,119 B2 | 10/2007 | Stewart et al. |
| 7,294,214 B2 | 11/2007 | Craig |
| 7,294,311 B2 | 11/2007 | Coville |

(56) References Cited

U.S. PATENT DOCUMENTS

| | | | |
|---|---|---|---|
| 7,303,560 B2 | 12/2007 | Chin et al. | |
| 7,306,618 B2 | 12/2007 | Demond et al. | |
| 7,306,622 B2 | 12/2007 | Jones et al. | |
| 7,309,354 B2 | 12/2007 | Mathis et al. | |
| 7,316,708 B2 | 1/2008 | Gordon et al. | |
| 7,319,035 B2 | 1/2008 | Vacanti et al. | |
| 7,323,001 B2 | 1/2008 | Clubb et al. | |
| 7,323,002 B2 | 1/2008 | Johnson et al. | |
| 7,323,003 B2 | 1/2008 | Lowe | |
| 7,329,269 B2 | 2/2008 | Shapiro et al. | |
| 7,331,976 B2 | 2/2008 | McGuckin, Jr. et al. | |
| 7,331,992 B2 | 2/2008 | Randall et al. | |
| 7,338,512 B2 | 3/2008 | McGuckin, Jr. et al. | |
| 7,344,553 B2 | 3/2008 | Opolski et al. | |
| 7,344,560 B2* | 3/2008 | Gregorich et al. | 623/1.15 |
| 7,351,259 B2 | 4/2008 | Swinford et al. | |
| 7,357,812 B2 | 4/2008 | Andreas et al. | |
| 7,359,752 B1 | 4/2008 | Bornzin et al. | |
| 7,363,082 B2 | 4/2008 | Ransbury et al. | |
| 7,364,588 B2 | 4/2008 | Mathis et al. | |
| 7,399,308 B2 | 7/2008 | Borillo et al. | |
| 7,431,691 B1 | 10/2008 | Wilk | |
| 7,445,630 B2 | 11/2008 | Lashinski et al. | |
| 7,452,371 B2 | 11/2008 | Pavcnik et al. | |
| 7,520,890 B2 | 4/2009 | Phillips | |
| 7,556,644 B2 | 7/2009 | Burpee | |
| 7,594,927 B2 | 9/2009 | Majercak et al. | |
| 7,611,531 B2 | 11/2009 | Calisse | |
| 7,722,661 B2 | 5/2010 | Lenz et al. | |
| 7,883,538 B2 | 2/2011 | To et al. | |
| 2001/0039434 A1 | 11/2001 | Frazier | |
| 2001/0044650 A1 | 11/2001 | Simso et al. | |
| 2002/0045935 A1 | 4/2002 | Jang | |
| 2002/0082682 A1 | 6/2002 | Barclay et al. | |
| 2002/0120323 A1 | 8/2002 | Thompson et al. | |
| 2002/0169474 A1 | 11/2002 | Kusleika et al. | |
| 2002/0183787 A1 | 12/2002 | Wahr et al. | |
| 2003/0028213 A1 | 2/2003 | Thill et al. | |
| 2003/0040771 A1 | 2/2003 | Hyodoh et al. | |
| 2003/0097172 A1 | 5/2003 | Shalev et al. | |
| 2003/0109887 A1 | 6/2003 | Galdonik et al. | |
| 2003/0114920 A1 | 6/2003 | Caro et al. | |
| 2003/0130726 A1 | 7/2003 | Thorpe et al. | |
| 2003/0144694 A1 | 7/2003 | Chanduszko et al. | |
| 2003/0167068 A1 | 9/2003 | Amplatz | |
| 2003/0191495 A1 | 10/2003 | Ryan et al. | |
| 2003/0195555 A1 | 10/2003 | Khairkhahan et al. | |
| 2003/0195609 A1 | 10/2003 | Berenstein et al. | |
| 2003/0199923 A1 | 10/2003 | Khairkhahan et al. | |
| 2003/0204203 A1 | 10/2003 | Khairkhahan et al. | |
| 2003/0208232 A1 | 11/2003 | Blaeser et al. | |
| 2003/0225421 A1 | 12/2003 | Peavey et al. | |
| 2004/0006381 A1* | 1/2004 | Sequin et al. | 623/1.35 |
| 2004/0039442 A1 | 2/2004 | St. Goar et al. | |
| 2004/0073242 A1 | 4/2004 | Chanduszko | |
| 2004/0088044 A1 | 5/2004 | Brown et al. | |
| 2004/0092973 A1 | 5/2004 | Chanduszko et al. | |
| 2004/0093017 A1 | 5/2004 | Chanduszko | |
| 2004/0102807 A1 | 5/2004 | Kusleika et al. | |
| 2004/0133236 A1 | 7/2004 | Chanduszko | |
| 2004/0147997 A1 | 7/2004 | Gittings | |
| 2004/0158247 A1 | 8/2004 | Sitiso et al. | |
| 2004/0158312 A1 | 8/2004 | Chouinard et al. | |
| 2004/0167609 A1 | 8/2004 | Majercak | |
| 2004/0176799 A1 | 9/2004 | Chanduszko et al. | |
| 2004/0186556 A1 | 9/2004 | Hogendijk et al. | |
| 2004/0186560 A1 | 9/2004 | Alt | |
| 2004/0204752 A1 | 10/2004 | Ehr et al. | |
| 2004/0215219 A1 | 10/2004 | Eldridge et al. | |
| 2004/0220585 A1 | 11/2004 | Nikolchev | |
| 2004/0249408 A1 | 12/2004 | Murphy et al. | |
| 2004/0267191 A1 | 12/2004 | Gifford, III et al. | |
| 2004/0267306 A1 | 12/2004 | Blaeser et al. | |
| 2004/0267350 A1 | 12/2004 | Roubin et al. | |
| 2005/0015136 A1 | 1/2005 | Ikeuchi et al. | |
| 2005/0043759 A1 | 2/2005 | Chanduszko | |
| 2005/0055080 A1 | 3/2005 | Istephanous et al. | |
| 2005/0090857 A1 | 4/2005 | Kusleika et al. | |
| 2005/0090858 A1 | 4/2005 | Pavlovic | |
| 2005/0107863 A1 | 5/2005 | Brown | |
| 2005/0131451 A1 | 6/2005 | Kleshinski et al. | |
| 2005/0131516 A1 | 6/2005 | Greenhalgh | |
| 2005/0192620 A1 | 9/2005 | Cully et al. | |
| 2005/0192626 A1 | 9/2005 | Widomski et al. | |
| 2005/0192654 A1 | 9/2005 | Chanduszko et al. | |
| 2005/0197186 A1 | 9/2005 | Ohta | |
| 2005/0197187 A1 | 9/2005 | Mitsuyoshi et al. | |
| 2005/0216054 A1 | 9/2005 | Widomski et al. | |
| 2005/0288764 A1 | 12/2005 | Snow et al. | |
| 2006/0015137 A1 | 1/2006 | WasDyke | |
| 2006/0020322 A1 | 1/2006 | Leynov et al. | |
| 2006/0106452 A1 | 5/2006 | Niermann | |
| 2006/0116751 A1 | 6/2006 | Bayle et al. | |
| 2006/0142849 A1 | 6/2006 | Killion et al. | |
| 2006/0247759 A1 | 11/2006 | Burpee et al. | |
| 2007/0055348 A1 | 3/2007 | Pryor | |
| 2007/0129786 A1 | 6/2007 | Beach et al. | |
| 2007/0185563 A1 | 8/2007 | Zarbatany et al. | |
| 2007/0198050 A1 | 8/2007 | Ravenscroft et al. | |
| 2007/0219618 A1 | 9/2007 | Cully et al. | |
| 2007/0232981 A1 | 10/2007 | Ravenscroft et al. | |
| 2007/0255387 A1 | 11/2007 | Kramer et al. | |
| 2008/0103584 A1 | 5/2008 | Su et al. | |
| 2008/0109068 A1 | 5/2008 | Fischell et al. | |
| 2008/0125849 A1 | 5/2008 | Burpee et al. | |
| 2008/0208319 A1 | 8/2008 | Rabkin et al. | |
| 2008/0215129 A1 | 9/2008 | Venturelli et al. | |
| 2008/0294240 A1 | 11/2008 | Casey | |
| 2008/0306581 A1 | 12/2008 | Berglund et al. | |
| 2009/0024205 A1 | 1/2009 | Hebert et al. | |
| 2009/0036976 A1 | 2/2009 | Beach et al. | |
| 2009/0099592 A1 | 4/2009 | Buiser et al. | |
| 2009/0118810 A1 | 5/2009 | Klein et al. | |
| 2009/0163989 A1 | 6/2009 | Contiliano et al. | |
| 2009/0182407 A1 | 7/2009 | Leanna et al. | |
| 2009/0210049 A1 | 8/2009 | Thielen et al. | |
| 2009/0264978 A1 | 10/2009 | Dieck et al. | |
| 2010/0004730 A1 | 1/2010 | Benjamin et al. | |
| 2010/0023106 A1 | 1/2010 | Meyer et al. | |
| 2010/0057187 A1 | 3/2010 | Caldarise et al. | |
| 2010/0076545 A1 | 3/2010 | Kleshinski et al. | |
| 2010/0137973 A1 | 6/2010 | Sutermeister et al. | |
| 2010/0222772 A1 | 9/2010 | Kleshinski et al. | |
| 2010/0294287 A1 | 11/2010 | Raju et al. | |
| 2011/0106237 A1 | 5/2011 | Bonsignore et al. | |
| 2011/0251671 A1* | 10/2011 | Heraty | A61F 2/915 623/1.15 |
| 2011/0301685 A1 | 12/2011 | Kao | |
| 2011/0307049 A1 | 12/2011 | Kao | |
| 2012/0078341 A1 | 3/2012 | Kao | |
| 2012/0078344 A1 | 3/2012 | Kao | |

FOREIGN PATENT DOCUMENTS

| | | |
|---|---|---|
| EP | 0335341 B1 | 3/1992 |
| EP | 0541063 A2 | 5/1993 |
| EP | 0621016 A1 | 10/1993 |
| EP | 0657147 A2 | 6/1995 |
| EP | 0701800 A1 | 3/1996 |
| EP | 0962194 A2 | 12/1999 |
| EP | 1050265 A2 | 11/2000 |
| EP | 1304091 A2 | 4/2003 |
| EP | 1917931 A2 | 5/2008 |
| JP | 06189971 A2 | 7/1994 |
| JP | 06343703 A2 | 12/1994 |
| JP | 07265339 A2 | 10/1995 |
| JP | 08089585 A2 | 4/1996 |
| JP | 08215200 | 8/1996 |
| JP | 08257031 | 10/1996 |
| JP | 08299456 A2 | 11/1996 |
| JP | 2000126304 A | 5/2000 |
| JP | 2002119516 A | 4/2002 |
| JP | 2002525183 | 8/2002 |
| JP | 2002355248 A | 12/2002 |

(56) References Cited

FOREIGN PATENT DOCUMENTS

| | | |
|---|---|---|
| JP | 2003521308 | 7/2003 |
| JP | 2003521988 | 7/2003 |
| WO | WO97/13463 A1 | 4/1997 |
| WO | WO 98/38945 A1 | 9/1998 |
| WO | WO 99/44540 A2 | 9/1999 |
| WO | WO 00/16718 A1 | 3/2000 |
| WO | WO 00/28922 A1 | 5/2000 |
| WO | WO 0028922 A1 * | 5/2000 .............. A61F 2/06 |
| WO | WO 00/57813 A1 | 10/2000 |
| WO | WO 03/051425 A2 | 6/2003 |
| WO | WO03/101312 A1 | 12/2003 |
| WO | WO2007/040249 | 4/2007 |
| WO | WO 2007/092276 A2 | 8/2007 |
| WO | WO2008/060345 A1 | 5/2008 |
| WO | WO2011/053737 A2 | 5/2011 |

OTHER PUBLICATIONS

Raju et al.; U.S. Appl. No. 11/944,094 entitled "Venous Stent," filed Nov. 21, 2007.
Raju et al.; U.S. Appl. No. 12/903,056 entitled "Venous Stent," filed Oct. 12, 2010.
Raju et al.; U.S. Appl. No. 12/603,970 entitled "Venous Stent," filed Oct. 22, 2009.
Duerig et al.; An overview of superelastic stent design; Min Invas Ther & Allied Technol; vol. 9(3/4); pp. 235-246; 2000.
Malvé et al.; FSI analysis of the coughing mechanism in a human trachea; Annals of Biomedical Engineering; vol. 38; No. 4; pp. 1556-1565; 2010.

* cited by examiner

|  | Expandable Ring Member | | | | Bridging Member | | | | |
| --- | --- | --- | --- | --- | --- | --- | --- | --- | --- |
|  | Number of Struts | Length of Struts | Width of Struts | Thickness of Struts | Number of Bridging Elements | Length of Bridging Elements | Angle of Bridging Elements | Width of Bridging Elements | Thickness of Bridging Elements |
| Greater Axial Flexibility | + | - | - | - | + | + | ++ | - | - |
| Greater Hoop Stiffness | - | - - | ++ | + | - | + |  | + | + |
| Greater Pinching Stiffness | - | - - | + | ++ | - | + | + | + | ++ |
| Less Rotation with Δ Diameter | 0 | 0 | 0 | 0 | 0 | - | - | 0 | 0 |
| Less Foreshortening | + | 0 | 0 | 0 | 0 | - | - | 0 | 0 |
| Greater Scaffolding performance | + | - | 0 | 0 | + | - | + | 0 | 0 |

FIG. 6C

| Location | Expanded Diameter/ Expanded Length in mm | Number of struts elements | Length/ width/ thickness of struts elements in mm | Length/ width/ thickness of bridging elements in mm | Pitch of bridge elements | Radial Stiffness | Modular Features | Other Notes |
|---|---|---|---|---|---|---|---|---|
| Iliac vein compression syndrome | 10-20/ 60-150 | 30-60 | 1-4/ 0.1-0.3/ 0.1-0.5 | 1-10/ 0.07-0.3/ 0.1-0.5 | Could vary axially, could be 20°-70° | Sufficient radial stiffness to resist thrombotic, post-thrombotic, and external compression in certain regions. Also, see modular features. | Extra stiffness in the form of extra struts/bridge elements in area of compression. Extra flexibility in the form of changing the angle of the bridge elements in region of inguinal ligament | |

FIG. 28a

| Location | Expanded Diameter/ Expanded Length in mm | Number of struts elements | Length/ width/ thickness of struts elements in mm | Length/ width/ thickness of bridging elements in mm | Pitch of bridge elements | Radial Stiffness | Modular Features | Other Notes |
|---|---|---|---|---|---|---|---|---|
| Superficial Femoral Artery | 6-10/ 20-150 | 20-50 | 1-4/ 0.05-0.2/ 0.1-0.3 | 1-108/ 0.03-0.2/ 0.1-0.3 | Could vary axially, could be 20°-70° | Sufficient radial stiffness to resist calcific lesions and recoil. Also, see modular features. | Sections in the pinned area of the adductor hiatus and canal can be made to be higher strength or stiffness relative other sections. The sections between the profunda and the adductor hiatus can be configured to be more flexible relative to other sections | |

FIG. 28b

| Location | Expanded Diameter/ Expanded Length in mm | Number of struts elements | Length/ width/ thickness of struts elements in mm | Length/ width/ thickness of bridging elements in mm | Pitch of bridge elements | Radial Stiffness | Modular Features | Other Notes |
|---|---|---|---|---|---|---|---|---|
| Coronary | 2-3.5/ 8-33 | 10-30 | 0.5-1.5/ 0.03-0.08/ 0.05-0.10 | 0.5-4/ 0.01-0.06/ 0.05-0.10 | Could vary axially, could be 20°-70° | Sufficient stiffness to resist recoil. Also, see modular features. | The section near an ostium can be more flexible than other sections. Other sections can be configured for drug delivery. Sections near side branches can be configured to be more flexible than other sections | The final contour of the implanted stent may needs to be significantly non-cylindrical and include abrupt changes in local diameter or cross section |

FIG. 28c

| Location | Expanded Diameter/ Expanded Length in mm | Number of struts elements | Length/ width/ thickness of struts elements in mm | Length/ width/ thickness of bridging elements in mm | Pitch of bridge elements | Radial Stiffness | Modular Features | Other Notes |
|---|---|---|---|---|---|---|---|---|
| Renal | 5-7/ 12-20 | 20-50 | 1-4/ 0.05-0.2/ 0.1-0.3 | 1-108/ 0.03-0.2/ 0.1-0.3 | Could vary axially, could be 20°-70° | See modular features. | The section near the ostium can be more flexible than the rest of the stent to accommodate movement caused by respiration. The section in the rest of the renal artery can have higher radial stiffness to support the artery | |

FIG. 28d

| Location | Expanded Diameter/ Expanded Length in mm | Number of struts elements | Length/ width/ thickness of struts elements in mm | Length/ width/ thickness of bridging elements in mm | Pitch of bridge elements | Radial Stiffness | Modular Features | Other Notes |
|---|---|---|---|---|---|---|---|---|
| Carotid | 4.0-10/ 20-60 | 20-50 | 1-4/ 0.05-0.2/ 0.1-0.3 | 1-108/ 0.03-0.2/ 0.1-0.3 | Could vary axially, could be 20°-70° | See modular features. | Sufficient stiffness to support a lesion in the carotid artery, but enough flexibility to avoid hemodynamic instability brought on by stimulation of baroreceptors. Section near carotid sinus can allow for abrupt changes in diameter and shape | |

FIG. 28e

| Location | Expanded Diameter/ Expanded Length in mm | Number of struts elements | Length/ width/ thickness of struts elements in mm | Length/ width/ thickness of bridging elements in mm | Pitch of bridge elements | Radial Stiffness | Modular Features | Other Notes |
|---|---|---|---|---|---|---|---|---|
| AV Graft and Fistula | 5-108/ 20-80 | 20-50 | 1-4/ 0.05-0.2/ 0.1-0.53 | 1-108/ 0.053-0.2/ 0.1-0.53 | Could vary axially, could be 20°-70° | Sufficient radial stiffness to resist thrombosis in certain regions. Also, see modular features. | Sections can be designed to allow for the abrupt change in diameter and shape or may need to assume an abrupt angle where the fistula or graft joins the native artery. Variable stiffness for arterial and venous regions. | |

FIG. 28f

| Location | Expanded Diameter/ Expanded Length in mm | Number of struts elements | Length/ width/ thickness of struts elements in mm | Length/ width/ thickness of bridging elements in mm | Pitch of bridge elements | Radial Stiffness | Modular Features | Other Notes |
|---|---|---|---|---|---|---|---|---|
| Tracheal | 11-20/ 30-110 | 20-50 | 2-8/ 0.1-0.5/ 0.15-0.21 | 2-10/ 0.07-0.5/ 0.15-0.21 | Could vary axially, could be 20°-70°, bridges may be always oriented in the same direction rather than alternating directions. | Appropriate radial stiffness to accommodate coughing. | | The bridges could be preferentially oriented in a direction that is closer to axial than circumferential, thus promoting functional mucociliary transport. Bridge orientation would be the same along the length, rather than alternating |

FIG. 28g

| Location | Expanded Diameter/ Expanded Length in mm | Number of struts elements | Length/ width/ thickness of struts elements in mm | Length/ width/ thickness of bridging elements in mm | Pitch of bridge elements | Radial Stiffness | Modular Features | Other Notes |
|---|---|---|---|---|---|---|---|---|
| Neurovascular -ischemic stroke | 2-7/ 5-100 | 10-30 | 0.5-1.5/ 0.03-0.08/ 0.04-0.10 | 0.5-4/ 0.01-0.06/ 0.04-0.10 | 30-60° | Overall low radial stiffness to avoid vessel rupture or dissection | Lower radial stiffness in center of stent to avoid excessive force that might cause vessel rupture or dissection. | May need to be undersized compared to the native vessel to avoid too much outward force that would cause arterial rupture or |

FIG. 28h

| Location | Expanded Diameter/ Expanded Length in mm | Number of struts elements | Length/ width/ thickness of struts elements in mm | Length/ width/ thickness of bridging elements in mm | Pitch of bridge elements | Radial Stiffness | Modular Features | Other Notes |
|---|---|---|---|---|---|---|---|---|
| Esophageal | 16-23/ 90-150 | 20-50 | 2-8/ 0.1-0.5/ 0.15-0.21 | 2-10/ 0.07-0.5/ 0.15-0.21 | Could vary axially, could be 20°-70° | Sufficiently low radial stiffness to enable peristalsis, but sufficiently high radial stiffness to resist migration into the stomach | One end of the stent V may be flared to accommodate the opening to the stomach T | |

FIG. 28i

| Location | Expanded Diameter/ Expanded Length in mm | Number of struts elements | Length/ width/ thickness of struts elements in mm | Length/ width/ thickness of bridging elements in mm | Pitch of bridge elements | Radial Stiffness | Modular Features | Other Notes |
|---|---|---|---|---|---|---|---|---|
| Subclavian & Brachio-cephalic (Innominate) Veins | 8-16/ 20-100 | 20-50 | 1-4/ 0.1-0.3/ 0.1-0.5 | 1-10/ 0.05-0.3/ 0.1-0.5 | Could vary axially, could be 20°-70° | Sufficient radial stiffness to resist thrombotic, post-thrombotic, and external compression in certain regions. Also, see modular features. | Extra stiffness in the form of extra struts/bridge elements in area of compression. Extra flexibility in the form of changing the angle of the bridge elements in region of the shoulder | |

FIG. 28j

ALTERNATING CIRCUMFERENTIAL BRIDGE STENT DESIGN AND METHODS FOR USE THEREOF

CROSS REFERENCE TO RELATED APPLICATIONS

This application claims priority to and is a continuation-in-part of U.S. patent application Ser. No. 12/939,894, filed Nov. 4, 2010, entitled "Alternating Circumferential Bridge Stent Design and Methods for Use Thereof," which claims priority to U.S. Provisional Patent Application Nos. 61/258,145, filed Nov. 4, 2009 entitled "Stent for Relief of Pelvic Venous Outflow Obstruction and Methods for Use Thereof;" 61/290,836, filed on Dec. 29, 2009 entitled "Alternating Circumferential Bridge Stent Design and Methods of Use Therefore;" and 61/391,462, filed on Oct. 8, 2010 entitled "Alternating Circumferential Bridge Stent Design and Methods for Use Thereof."

These applications are herein incorporated by reference in their entirety.

INCORPORATION BY REFERENCE

All publications and patent applications mentioned in this specification are herein incorporated by reference to the same extent as if each individual publication or patent application was specifically and individually indicated to be incorporated by reference.

FIELD OF THE INVENTION

The present invention relates to stents and more particularly to stents having different modules that, when combined, provide advantages for the physiological challenges posed in particular anatomies.

BACKGROUND OF THE INVENTION

Generally, stents are used as an alternative to surgery to obtain and maintain the patency of a variety of body passageways, while maintaining the integrity of the passageway. The environments of human vasculature and body passageways are characterized by varied, dynamic, and mobile anatomy. Vessels vary from simple to complex shapes, can be uniform in diameter or change abruptly or gradually from one diameter to another, and are subjected to a range of internal forces exerted by blood or air pressure, and external forces exerted by an assortment of anatomical structures surrounding and adjacent to these body passageways. It is critical that stents be designed to accommodate significant variation in the shape and size of body passageways while providing structural support and flexibility as required by particular indications of use.

The primary role of a stent is to provide radial expansion and scaffolding within the affected segment, thereby improving patency or flow and preserving the viability and full function of distal tissues. In performing this primary function, however, a stent must exist in harmony with surrounding structures of the body, including vessels, nerves, muscles, organs, and other tissues. Each region of the anatomy presents a unique combination of loads, interactions, and constraints that will be experienced by the implant. In many regions of the anatomy, these boundary conditions will vary not only with location, but also with time. These temporal variations, including motions associated with the cardiac pulsatile cycle, gait cycle, respiratory cycle, or other dynamic events, are especially important considerations for the durability of the implant itself, as well as the efficacy of the therapy. Consequently, stent designs are needed that can (1) provide adequate outward radial support to remodel the lumen and improve distal perfusion in the case of vascular anatomies, (2) provide adequate crush recoverability when subjected to compression by the surrounding muscles or external forces, (3) provide adequate flexibility to accommodate localized stretching, compression, bending, or torsion in mobile segments of the artery or other passageway, (4) provide durability to survive the motions associated with the cardiac, respiratory or gait cycles and/or limb flexion, and (5) provide uniform scaffolding throughout the treatment region, including the local regions adjacent to calcification that may be subjected to highly focal cyclic loading or displacement. These competing demands have proven difficult to resolve with a single design.

SUMMARY OF THE INVENTION

In general, in one aspect, a stent includes a first section and a second section. The second section is aligned with the first section along a longitudinal axis of the stent. Each section includes a plurality of expandable modules and a plurality of bridging modules. Each expandable module includes a plurality of strut elements that join together at a plurality of apices. Each bridging module includes bridging elements that connect an apex of a first module with an apex of a second module. The plurality of expandable modules or the plurality of bridging modules in the first section are more radially stiff than the plurality of expandable modules or the plurality of bridging modules in the second section such that at least a portion of the first section is configured to be placed in a region of a vein subjected to physiologic compression.

Physiologic compression refers to any of a number of forces internal or external to the body that act on a vessel. As a result of the force of physiologic compression, the vessel is partially or fully occluded. Physiologic compression may exist when a structure moves into contact with and acts against a wall of a vessel. Physiologic compression may also exist when a structure moves against a vessel to displace or distend it into contact with another structure to pinch off fully or partially the vessel. In a third example, physiologic compression exists where two structures move in opposition against a vessel, which can result in partial or complete occlusion of the impacted vessel. The structures may be any of the structures of the body that may move against a vessel of lumen. Examples of such structures include a tendon, a vein, an artery, a muscle, a bone or skeletal structure, a cartilage. The impacted vessel or lumen may include veins, arteries, or capillaries of the vasculature or other lumens in the body including lumens found within the gastrointestinal tract, the digestive system, the lymphatic network, the respiratory system, the endocrine system, and the urinary system.

This and other embodiments can include one or more of the following features.

The plurality of bridging modules can be arranged to alternate along the longitudinal axis between clockwise bridging modules and counterclockwise bridging modules, the clockwise bridging modules including bridging elements that extend at a clockwise angle with respect to the longitudinal axis, and the counterclockwise bridging modules including bridging elements that extend at a counterclockwise angle with respect to the longitudinal axis. The clockwise bridging modules can be configured to counterbalance any rotation caused by the counterclockwise bridging modules.

The physiologic compression can be arterial compression. The at least a portion of the first section can be configured to be placed in a left common iliac vein where the right common iliac artery crosses the left common iliac vein or in the left external iliac vein where the left internal iliac artery crosses the left external iliac vein.

The first section can have an axial length of between approximately 1 cm and 3 cm, such as 2 cm. The second section can have an axial length of between approximately 4 cm and 10 cm, such as approximately 7 cm. The first section can have a radial stiffness that is approximately 1.1 to 3 times the radial stiffness of the second section, such as approximately 2 times the radial stiffness of the second section. A length of each strut element in the first section can be 5-50% lower than a length of each strut element in the second section. The length of each strut element in the first section or in the second section can be between approximately 1 mm and 4 mm. The length of each strut element in the first section can be approximately 2.1 mm, and the length of each strut element in the second section is approximately 2.5 mm. A width of each strut element in the first section can be 5-50% higher than a width of each strut element in the second section. The width of each strut element in the first section or in the second section can be between approximately 0.1 mm and 0.3 mm. The width of each strut element in the first section can be approximately 0.16 mm, and the width of each strut element in the second section can be approximately 0.12 mm. A length of each bridging element in the first section can be 5-50% shorter than a length of each bridging element in the second section. The length of each bridging element in the first section or in the second section can be between approximately 1 mm to 10 mm. The length of each bridging element in the first section can be approximately 6 mm, and the length of each bridging element in the second section can be approximately 7 mm. A width of each bridging element in the first section can be 5-50% higher than a width of each bridging element in the second section. The width of each bridging element in the first section or in the second section can be approximately 0.07 mm to 0.3 mm. The width of each bridging element in the first section can be approximately 0.12 mm, and the width of each bridging element in the second section can be approximately 0.1 mm.

The stent can further include a third section. The third section can be adjacent to the second section and located along the longitudinal axis of the stent. The third section can be more radially stiff than the second section such that at least a portion of the third section is configured to be placed in the vein in a second region of physiologic compression. The third section can be configured to have an axial length of approximately 1 cm to 3 cm, such as approximately 2 cm. The at least a portion of the first section can be configured to be placed in a left common iliac vein where a right common iliac artery crosses the left common iliac vein, and the at least a portion of the third section can be configured to be placed in a left internal iliac artery wherein the left internal iliac artery crosses the left external iliac vein.

The stent can further include a fourth section. The fourth section can be located along the longitudinal axis of the stent. The fourth section can be more flexible than the first and third sections such that at least a portion of the fourth section is configured to be placed in an area of the vein having high curvature.

At least a portion of the fourth section can be configured to be placed in the left common iliac vein where the left iliac vein approaches or cross an inguinal ligament. The fourth section can be configured to have an axial length of approximately 3 cm to 5 cm, such as approximately 4 cm.

In general, in one aspect, a stent includes a first section and a second section. The second section is aligned with the first section along a longitudinal axis of the stent. Each section includes a plurality of expandable modules and a plurality of bridging modules. Each expandable module includes a plurality of strut elements that join together at a plurality of apices. Each bridging module includes bridging elements that connect an apex of a first module with an apex of a second module. The plurality of expandable modules or the plurality of bridging modules in the first section are more flexible than the plurality of expandable modules or the plurality of the bridging modules in the second section such that at least a portion of the first section is configured to be placed in a region of a vein having high curvature.

This and other embodiments can include one or more of the following features.

The plurality of bridging modules can be arranged to alternate along the longitudinal axis between clockwise bridging modules and counterclockwise bridging modules, the clockwise bridging modules including bridging elements that extend at a clockwise angle with respect to the longitudinal axis, and the counterclockwise bridging modules including bridging elements that extend at a counterclockwise angle with respect to the longitudinal axis. The clockwise bridging modules can be configured to counterbalance any rotation caused by the counterclockwise bridging modules.

The region of the vein having high curvature can be an area where the vein crosses a ligament. The at least a portion of the first section can be configured to be placed in a left common iliac vein where the left iliac vein approaches or crosses the inguinal ligament. The first section can have an axial length of between approximately 3 cm and 5 cm, such as approximately 4 cm.

The first section can have a flexibility that is approximately 1.1 to 3 times the flexibility of the second section, such as approximately 2 times the flexibility of the second section. A length of each strut element in the first section can be 5-50% higher than a length of each strut element in the second section. The length of each strut element in the first section or in the second section can be between approximately 1 mm and 4 mm. The length of each strut element in the first section can be approximately 3.0 mm, and the length of each strut element in the second section is approximately 2.5 mm. A width of each strut element in the first section can be 5-50% lower than a width of each strut element in the second section. The width of each strut element in the first section or in the second section can be between approximately 0.1 mm and 0.3 mm. The width of each strut element in the first section can be approximately 0.1 mm, the width of each strut element in the second section can be approximately 0.12 mm. A length of each bridging element in the first section can be 5-50% higher than a length of each bridging element in the second section. The length of each bridging element in the first section or in the second section can be between approximately 1 mm and 10 mm. The length of each bridging element in the first section can be approximately 8 mm, the length of each bridging element in the second section can be approximately 7 mm. A width of each bridging element in the first section can be 5-50% lower than a width of each bridging element in the second section. The width of each bridging element in the first section or in the second section can be approximately 0.07 mm to 0.3 mm. The width of each bridging element in the first section can be approximately 0.08 mm, and the width of each bridging element in the second section can be approximately 0.1 mm.

The stent can further include a third section. The third section can be adjacent to the second section and located along the longitudinal axis of the stent. The third section can be more radially stiff than the second section such that at least a portion of the third section is configured to be placed in the vein in a region of physiologic compression.

In general, in one aspect, a method can include inserting a stent into a vein. The stent includes a first section. The first section is more radially stiff than the second section. Each section includes a plurality of expandable modules and a plurality of bridging modules. Each expandable module includes a plurality of strut elements that join together at a plurality of apices. Each bridging module includes bridging elements that connect an apex of a first module with an apex of a second module. The method can further include aligning at least a portion of the first section with a region of the vein that is subjected to physiologic compression.

In general, in one aspect, a method can include inserting a stent into a vein. The stent includes a first section. The first section is more flexible than the second section. Each section includes a plurality of expandable modules and a plurality of bridging modules. Each expandable module includes a plurality of strut elements that join together at a plurality of apices. Each bridging module includes bridging elements that connect an apex of a first module with an apex of a second module. The method can further include aligning at least a portion of the first section with a region of the vein that has high curvature.

In other embodiments, a stent can have the features as described hereinabove, but can be configured to be placed in a different location in the body.

In one aspect, the stent is configured to be placed in a femoral artery. A femoral artery stent could vary in diameter from 6-10 mm, and vary in length from 20-150 mm. There could be 20 to 50 struts elements in each expandable ring member. Further, the length, width and thickness of the strut elements in each expandable ring member can be between 1-4 mm, 0.05-0.2 mm, and 0.1-0.3 mm, respectively. Further, the length, width and thickness of the bridging elements in the bridging members can be between 1-10 mm, 0.03-0.2 mm, and 0.1-0.3 mm, respectively. The pitch of the bridging elements can be between 20° and 70°.

In one aspect, the stent is configured to be placed in a coronary artery. A coronary artery stent could vary in diameter from 2-3.5 mm, and vary in length from 8-33 mm. There could be 20 to 50 strut elements in each expandable ring member. Further, the length, width and thickness of the strut elements in each expandable ring member can be between 0.5-1.5 mm, 0.03-0.0.08 mm, and 0.05-0.10 mm, respectively. Further, the length, width and thickness of the bridging elements in the bridging member can be between 0.5-4 mm, 0.01-0.06 mm, and 0.05-0.10 mm, respectively. The pitch of the bridging elements can be between 20° and 70°.

In one aspect, the stent is configured to be placed in a renal artery. A renal artery stent could vary in diameter from 5-7 mm, and vary in length from 12-20 mm. There could be 20 to 50 strut elements in each expandable ring member. Further, the length, width and thickness of the strut elements in each expandable ring member can be between 1-4 mm, 0.05-0.2 mm, and 0.1-0.3 mm, respectively. Further, the length, width and thickness of the bridging elements in each bridging member can be between 1-10 mm, 0.03-0.2 mm, and 0.1-0.3 mm, respectively. The pitch of the bridging elements can be between 20° and 70°.

In one aspect, the stent if configured to be placed in a carotid artery. A carotid stent could vary in diameter from 4-10 mm, and vary in length from 20-60 mm. There could be 20 to 50 strut elements in each expandable ring member. The length, width and thickness of the strut elements in each expandable ring member can be between 1-4 mm, 0.05-0.2 mm, and 0.1-0.3 mm, respectively. Further, the length, width and thickness of the bridging elements in each bridging member can be between 1-10 mm, 0.03-0.2 mm, and 0.1-0.3 mm, respectively. The pitch of the bridging elements can be between 20° and 70°.

In one aspect, the stent can be configured to be placed in a fistula. A fistula stent could vary in diameter from 5-10 mm, and vary in length from 20-80 mm. There could be 20 to 50 strut elements in each expandable ring member. Further, the length, width and thickness of the strut elements in each expandable ring member can be between 1-4 mm, 0.05-0.2 mm, and 0.1-0.5 mm, respectively. Further, the length, width and thickness bridging elements in each bridging member can be between 1-10 mm, 0.05-0.2 mm, and 0.1-0.5 mm, respectively. The pitch of the bridging elements can be between 20° and 70°.

In one aspect, the stent can be configured to be placed in a trachea. A tracheal stent could vary in diameter from 11-20 mm, and vary in length from 30-110 mm. For example, there can be 20 to 50 strut elements in each expandable ring member. Further, the length, width and thickness of the struts elements in each expandable ring member can be between 2-8 mm, 0.1-0.5 mm, and 0.15-0.21 mm, respectively. Further, the length, width and thickness of bridging elements in each bridging member can be between 2-10 mm, 0.07-0.5 mm, and 0.15-0.21 mm, respectively. The pitch of the bridging elements can be between 20° and 70°.

In one aspect, the stent can be configured to be placed in the neurovascular system. A neurovascular stent could vary in diameter from 2-7 mm, and vary in length from 5-100 mm. For example, there can be 10 and 30 strut elements in each expandable ring member. Further, the length, width and thickness of the strut elements in each expandable ring member can be between 0.5-1.5 mm, 0.03-0.08 mm, and 0.04-0.10 mm, respectively. Further, the length, width and thickness of the bridging elements in each bridging member can be between 0.5-4 mm, 0.01-0.06 mm, and 0.04-0.10 mm, respectively. The pitch of the bridging elements can be between 30° and 60°.

In one aspect, the stent can be configured to be placed in the esophagus. An esophageal stent could vary in diameter from 16-23 mm, and vary in length from 90-150 mm. For example, there can be 20-50 strut elements in each expandable ring member. Further, the length, width and thickness of the strut elements in each expandable ring member can be between 2-8 mm, 0.1-0.5 mm, and 0.15-0.21 mm, respectively. Further, the length, width and thickness of the bridging elements in each bridging member can be between 2-10 mm, 0.07-0.5 mm, and 0.15-0.21 mm, respectively. The pitch of the bridging elements can be between 20° and 70°.

In one aspect, the stent can be configured to be placed in a central vein. A central vein stent could vary in diameter from 8-16 mm, and vary in length from 20-100 mm. There could be 20 to 60 struts elements in each expandable ring member. Further, the length, width and thickness of the strut elements in each expandable ring member can be between 1-4 mm, 0.1-0.3 mm, and 0.1-0.5 mm, respectively. Further, the length, width and thickness of the bridging elements in the bridging members can be between 1-10 mm, 0.05-0.3 mm, and 0.1-0.5 mm, respectively. Further, the pitch of the bridging elements could be between 20° and 70°.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which.

FIG. 6C shows a chart of variables vs. module characteristics for the stents described herein.

FIG. 28 shows a chart of a stent application vs. stent characteristics.

DETAILED DESCRIPTION OF THE INVENTION

Embodiments of the present invention are directed toward stents having a modular architecture that permits regions of the stent to be specifically tailored to the specific anatomical challenges of the vessel undergoing treatment. While applicable to other portions of the body where compression resistive and/or flexible stents are well suited, the illustrative embodiments described herein are directed at stents designed to resolve obstructive lesions of the pelvic veins, femoral arteries, coronary arteries, renal arteries, carotid arteries, fistulae, and trachea, cerebral arteries, or an esophagus.

Embodiments of the stent described herein include a combination of a number of different modules. The physical and engineering properties of each module are tailored depending upon the required function of the module with respect to the rest of the stent. Examples of different types of modules include: (1) modules designed to provide radial stiffness to anchor the stent or to resist external compressive forces; and (2) modules configured to provide added flexibility to the stent within the treated vessel in order to maintain patency of the vessel. Stent embodiments according to the present invention include one or more modules that are specifically sized and positioned with respect to one another so as to conform to a specific anatomical position.

Stent Description

Figure 1:
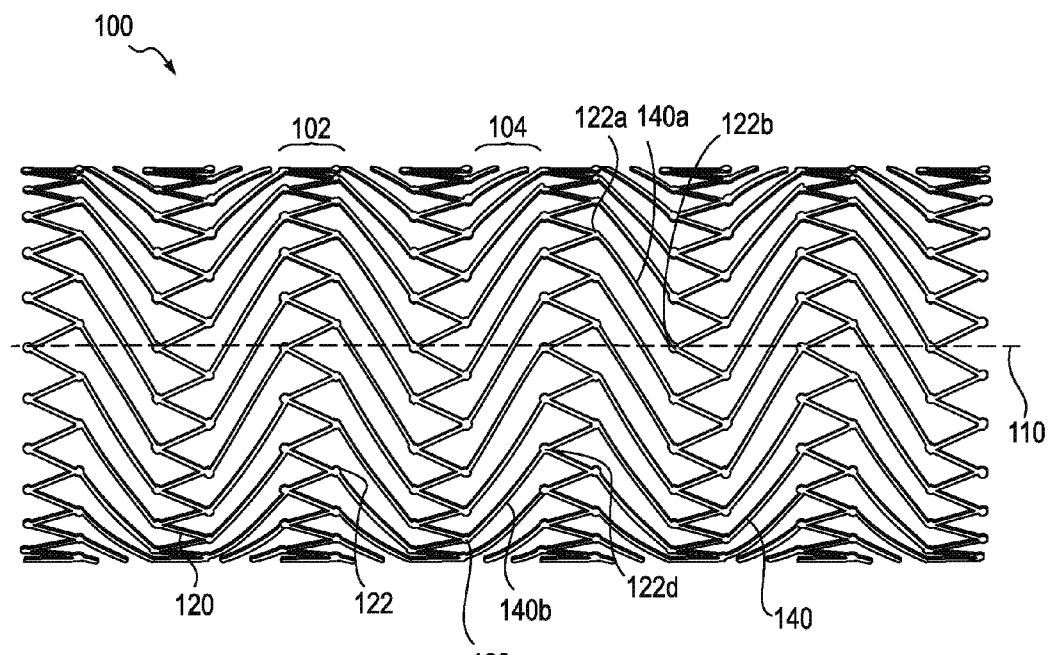
FIG. 1 shows an exemplary stent as described herein.

Referring to FIG. 1, a stent 100 can include a series of expandable ring members 102 connected by bridging members 104. Each expandable ring member 102 can include a series of strut elements 120 disposed around the circumference of the stent 100. Moreover, each bridging member 104 can include circumferential bridging elements 140 connecting the strut elements 120 of adjacent expandable ring members 102. The pitch of the circumferential bridging elements 140 can alternate between bridging members 104. The number, design, order, and connection of the expandable ring members 102 and bridging members 104 define the overall architecture of the stent 100. The strength, stiffness, flexibility, and rotational bias of the stent can be controlled by the selection and design of these expandable ring members 102 and bridging members 104.

Expandable Ring Members

Figure 2:
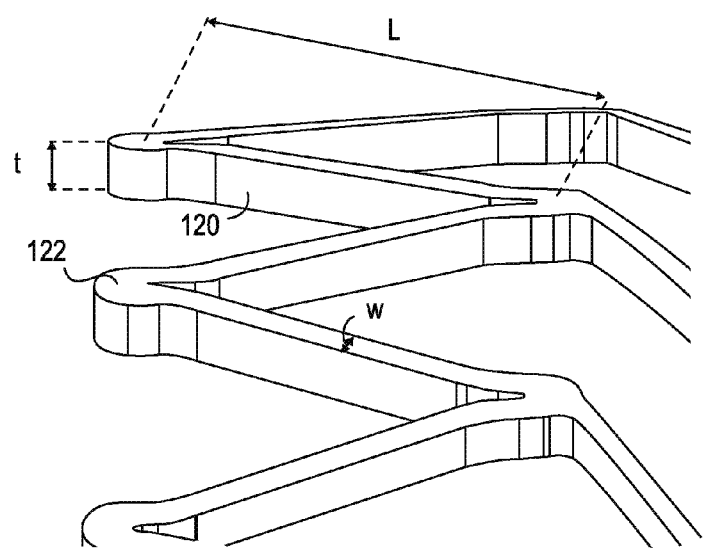
FIG. 2 is a close up of a portion of an expandable ring member described herein.

Referring to FIGS. 1 and 2, the expandable ring members 102 can include a series of struts elements 120 arranged in a zig-zag shape around the circumference of the stent 100. That is, the struts elements 120, arranged around the circumference of the stent 100, can connect together at apices 122.

Axial Flexibility

Figure 6A:
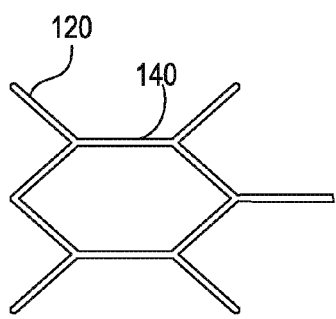
FIG. 6A shows a stent having bridge elements arranged axially.

It is commonly desirable to provide a stent structure that allows for smooth contouring and apposition in curved vessels or lumens following an irregular axial path. In such cases, the ideal stent can vary its local curvature in a continuous manner to accommodate any state of vessel bending. To maximize axial flexibility, it is desirable to decrease the axial length of strut elements 120, as bending is more likely to occur at the transition between the adjacent expandable ring members 102. Generally, axial flexibility of the stent is improved by minimizing the width w and thickness t of these strut elements 120, as this decreases the overall stiffness of the structure. Similarly, as the number of strut elements 120 around the circumference increases, strut width typically decreases, as there is a finite amount of material from which to form the struts, which also tends to improve axial flexibility. Thus, as shown in FIG. 6C, the axial flexibility of an expandable ring member can be increased by increasing the number of struts, decreasing the length of the struts, or decreasing the width, or thickness.

Hoop Stiffness

The zig-zag shape of the expandable ring members 102 can be designed to provide a specific radial stiffness. Such radial stiffness can be important for resisting concentric or eccentric radial forces and maintaining the shape of the stent 100 once deployed.

The stiffness, k, of an expandable ring member 102 when subjected to a hoop load, e.g., as a result of a perfectly concentric lesion, can be approximated by the following relationship:

$$k_{hoop} \alpha (Ew^3 t)/(nL^3) \quad [1]$$

where each expandable ring member 102 include a series of n strut elements 120 disposed around the circumference of the stent 100, each strut having a length L, a width w, a thickness t, (as shown in FIG. 2) and made of a material having a Young's Modulus E. In this mode of loading, the "hoop" stiffness is dominated by the cube of the strut width, and inversely related to the cube of the strut length. Thus, as shown in FIG. 6C, the hoop stiffness of an expandable ring member can thus be increased by decreasing the number of struts, decreasing the length of the struts, increasing the width of the struts, or increasing the thickness of the struts.

Pinching Stiffness

Moreover, the stiffness, k, of an expandable ring member 102 when subject to a pinching or buckling load, e.g., as a result of eccentric loads, can be described by a different stiffness formulation:

$$k_{pinching} \alpha (Ewt^3)/(nL^3) \quad [2]$$

As shown in FIG. 6C, the pinching stiffness, like the hoop stiffness, can thus be increased by decreasing the number of struts, decreasing the length of the struts, increasing the width of the struts, or increasing the thickness of the struts. In this mode of loading, however, "pinching" stiffness is dominated by the cube of wall thickness, rather than strut width as it was for hoop stiffness. An effective stent for treatment of a vessel subject to pinching or buckling, therefore, will maximize wall thickness to maximize resistance to the pinching load experienced.

Foreshortening

Stents commonly experience changes in orientation or length during the transition from constrained to expanded, or the vice versa. For example, a decrease in stent length can occur between the constrained stent and the expanded stent, called foreshortening. Two stents of the same diameter and same strut element 120 dimensions, but different numbers of strut elements 120 in each expandable ring members 102, can experience differing amounts of foreshortening. For example, a stent with few strut elements 120 in the expandable ring members 102 will be stretched significantly during expansion, leading to more foreshortening. Thus, as shown in FIG. 6C, a greater number of strut elements 120 in each expandable ring member 102 will result in decreased foreshortening.

Restorative Force

The zig-zag shape of the expandable ring members 102, in combination with the radial stiffness, can be further designed to provide a specific restorative force, acting in a radially outward direction to restore the patency of the a constricted lumen. Having a high restorative force can be important for providing the initial expansion force and for resisting concentric or eccentric radial forces placed on the stent 100 after implantation.

Figure 3A:
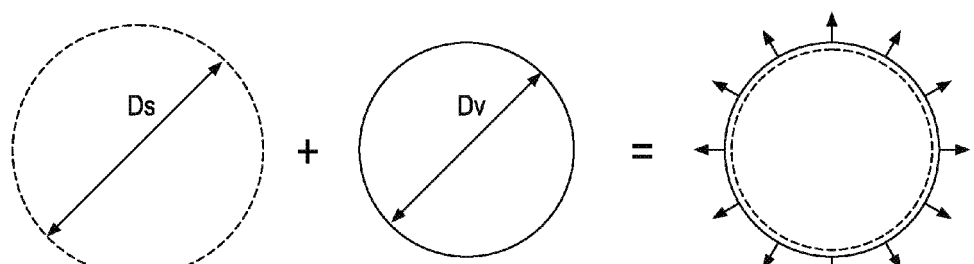
FIGS. 3A-3B are depictions of the relationship of the stent to vessel and lesion diameters.
Figure 3B:
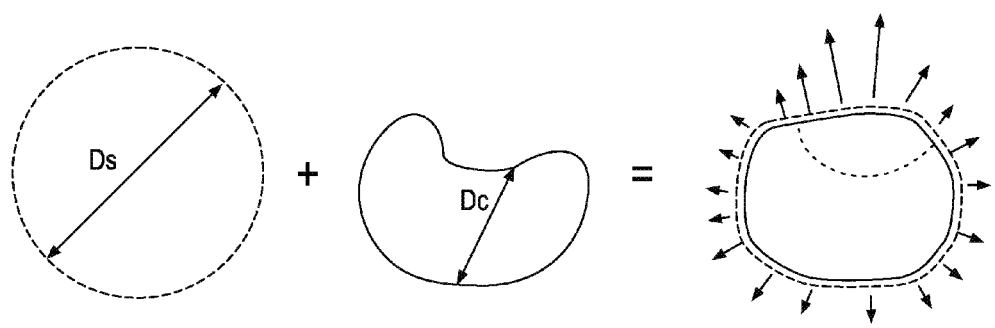

Referring to FIGS. 3A-3B, Dv is the normal effective diameter of the vessel immediately adjacent the lesion, Dc is the constricted effective diameter in the region of the lesion, and Ds is the effective diameter of the expanded stent. To increase the force applied, the diameter Ds of each expandable member can be chosen to be somewhat larger than the largest effective diameter Dv of the reference vessel. Referring to FIG. 3A, for areas having concentric lesions, the expandable member can be designed to have a uniform expansion force. As such, Ds−Dv>0, and the inserted expandable member can remain in contact with the vessel at all times and all locations. In contrast, referring to FIG. 3B, for areas having eccentric lesions, such as in areas where compression, luminal webbing, or spurs further constrict the effective lumen diameter to the constricted diameter Dc, the expandable ring member 102 can be designed to provide additional force at a particular location. Accordingly, the inserted expandable member will be more constrained (or "oversized") in this area of constriction than in the area of normal lumen: (Ds−Dc)>(Ds−Dv).

The amount of restorative force generated by a strut deflected by a distance δ can be expressed by the following equation for hoop force:

$$F_{hoop} = [(12EI)/(L^3)]\delta$$

where E is Young's Modulus for the material, I is the moment of inertia of the strut with respect to its axis of bending as the stent expands or contracts, L is the length of the strut, and δ is the magnitude of strut deflection in the cylindrical plane. Thus, the amount of force that a particular module can apply is enhanced by maximizing the amount of deflection (i.e. increasing oversizing), decreasing strut length, or increasing I by maximizing strut width and thickness.

Bridging Members

Referring back to FIG. 1, adjacent bridging members 104 can have bridging elements 140 that extend between apices 122 of adjacent expandable ring members 102. The bridging elements 140 can extend in a circumferential direction, i.e. between 0° and 90° from the longitudinal axis 110 of the stent.

As shown in FIG. 1, the bridging elements 140 of adjacent bridging members 104 along the longitudinal axis 110 of the stent can have an opposite pitch from one another. The bridging members 104 can thus alternate between having bridging elements 140a that extend from a first apex 122a to a second apex 122b at a clockwise angle (otherwise known as a negative angle) with respect to the longitudinal axis 110 and bridging elements 140b that extend from a first apex 122c to a second apex 122d at a counter-clockwise angle (otherwise known as a positive angle) with respect to the longitudinal axis 110 of the stent.

The alternating pitch of the circumferential bridging members 104 advantageously prevents the stent 100 from responding with a bias to torsional loading. If all of the bridging members 104 were alternatively oriented with the same pitch, a torsional load of a given direction may cause the stent to twist and/or to preferentially expand or contract in diameter. With an alternating pitch, the bias to torsional loading can be partially removed. That is, alternating the pitch allows the tendency for one bridging member 104 to rotate clockwise to be balanced by the adjacent bridging member's tendency to rotate counterclockwise. Further, having alternating pitch allows the stent 100 to accommodate significant axial, bending, or torsional deformation with relatively low amounts of strain because the loads can be distributed across the bridging elements 140. In some embodiments, the pitch of adjacent bridging members 104 is exactly opposite so as to fully balance out the torsional load across the stent 100. In other embodiments, a desired amount of twist can be purposefully imparted into a first section of the stent 100 and balanced out in another section of a stent 100. In still other embodiments, the stent can include an overall twist caused by an unbalanced pitch. Imparting an intentional twist into all or a section of the stent 100 might be important for matching a twist in a particular anatomy.

Figure 4:
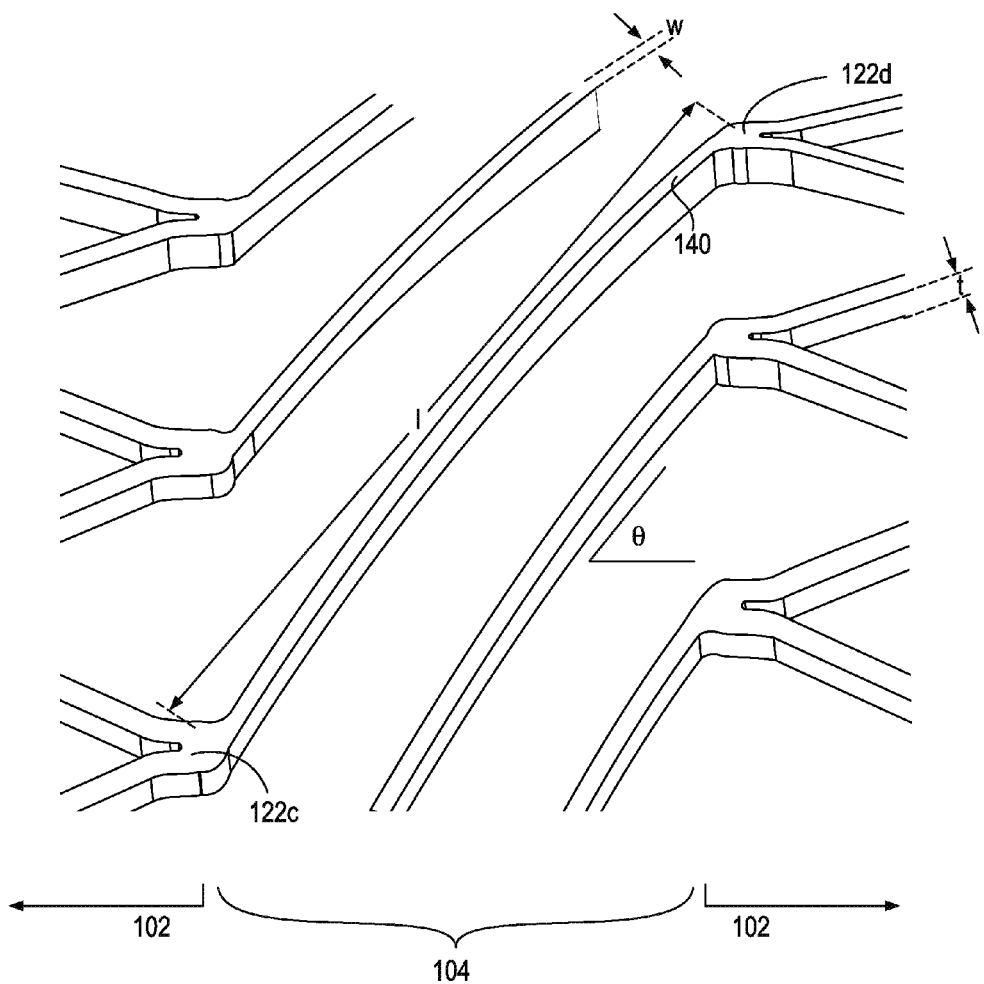
FIG. 4 is a close up of a portion of a bridging member described herein.

Referring to FIG. 4, a bridging element 140 can extend between each pair of internal apices 122c and 122d of expandable ring members 102. The circumferential bridging element 140 can have a length l as measured from apex 122A to apex 122B, a width w and a thickness t. Moreover, the angle between the length of the bridging elements 140 and a line extending parallel with the longitudinal axis of the strut can be offset by a circumferential angle θ. The angle θ can be used to describe the change in circumferential position traversed by a circumferential bridging element 140.

Axial Flexibility

The bridging members 104 can be used to influence the axial flexibility of the stent 100 when subjected to various loads. Flexibility is particularly important for those portions of the stent that approach or cross a ligament, bone, muscle or other anatomical feature that may alter or influence the response characteristics of the treated vessel.

Figure 5:
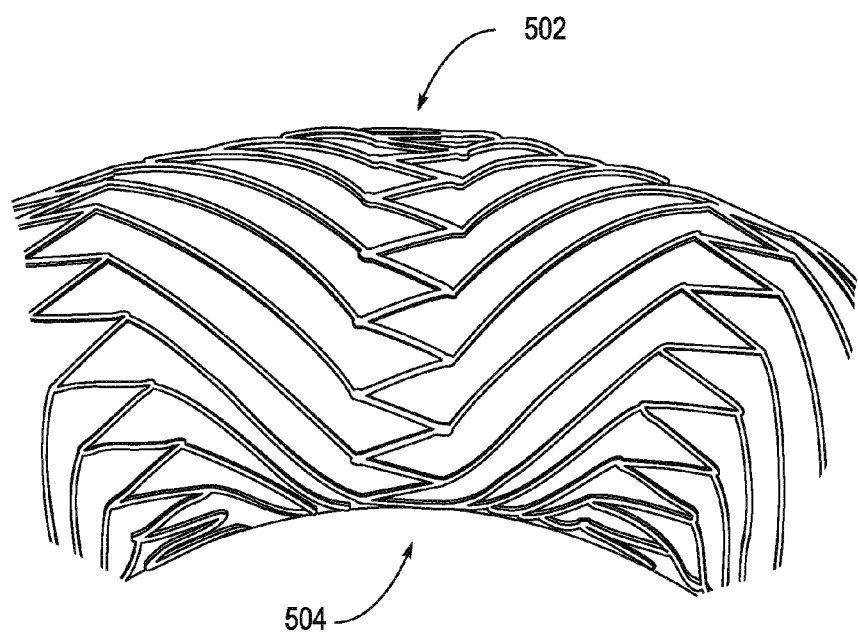
FIG. 5 shows a stent as described herein bent axially.

Referring to FIG. 5, as the stent 100 bends axially, the bridging elements along the outer curve 502 will spread apart, while the bridging elements along the inner curve 504 will draw closer together. Thus, as the length of a bridging element is increased, the longitudinal flexibility of the stent will increase because the bridging elements will be able to spread apart further along the outer curve 502. Likewise, the greater the angle θ, the greater the longitudinal flexibility of the stent because each bridging element 140 has a greater ability to stretch along the outer curve 502. As with the strut elements 120 described above, increasing the width w and thickness t of the bridging elements 140 tends to increase the overall stiffness of the structure, and thus adversely impact axial flexibility of the structure. Again, increasing the number of bridging elements 140, while correspondingly reducing the width of individual bridging elements 140, allows for bending loads to be distributed more uniformly throughout the structure, and generally improve axial flexibility. Thus, as shown in FIG. 6C, the axial flexibility of a bridging member can be increased by increasing the number of bridging elements, increasing the length of each bridging element, increasing the angle θ, and decreasing the width and/or thickness of each bridging element.

Hoop Stiffness

The bridging elements 140 contribute to hoop stiffness by a length l in combination with angle θ. As θ varies from an axial orientation) (0° to a circumferential orientation)(90°, the contribution to hoop stiffness ranges from low to high. Bridging elements that are axially oriented have no impact, as they simply translate in a radial direction as the stent is expanded, contracted, or exposed to hoop forces. Bridging elements that are circumferentially oriented, however, are oriented in the same direction as hoop forces, contribute to carrying hoop loads, and therefore increase hoop stiffness of the structure. The magnitude of this effect is positively correlated with the length l of the bridging element 140; very short bridging elements have little impact at all, while longer bridging elements have an increasing impact. Thus, as shown in FIG. 6C, increasing both the length and angle of the bridging elements 140 in combination increases hoop stiffness. In addition, increasing the width and thickness of the bridging elements 140 also increases hoop stiffness, as shown in equation 1. Lastly, decreasing the number of bridging elements 140 allows the elements to be wider, which also increases the hoop stiffness.

Pinching Stiffness

Altering the bridging elements 140 in the bridging member 104 can alter the pinching stiffness of the stent. Specifically, as shown in FIG. 6C, the pinching stiffness can be increased by decreasing the number of bridging elements 140, increasing the length and angle of the bridging elements 140 in combination, as well as increasing the width of the bridging elements. Most importantly, though, increasing the thickness of the bridging elements has a strong effect on increasing the pinching stiffness of the bridging member 104.

Rotation and Foreshortening

Stents commonly experience changes in orientation or length during the transition from constrained to expanded, or the vice versa. For example, a decrease in stent length can occur between the constrained stent and the expanded stent, called foreshortening. One component of foreshortening results from the change in angle of the struts elements 120 comprising the expandable ring members 102 as the strut is expanded.

The bridging elements 140 can compensate for some of the foreshortening experienced by the expandable ring members 102. As the length l and the angle θ of the bridging elements 140 decrease in combination, the difference in length between the constrained and expanded condition of the stent 100 also decreases. Minimizing the amount of foreshortening is generally desirable to improve the predictability and accuracy of deployment and positioning. Thus, compensating for foreshortening provides motivation to moderate the length l and angle θ of the bridging members 104. Thus, as shown in FIG. 6C, foreshortening can be decreased by decreasing the length and angle of the bridging members in combination:

Further, as length l and angle θ decrease, the expandable ring members 102 will have a decreasing tendency to rotate relative to each other as the stent expands or contracts. Relative rotation between expandable ring members 102 can cause the stent to be unstable, disrupt the surrounding tissue, and/or exert undesirable forces or strain on the surrounding structures, providing further motivation to moderate the length l and angle θ. Moreover, because the angle θ changes as the stent is expanded or constrained, the relative rotational twisting experienced between adjacent expandable ring members 102 during expansion or constraining also increases. Thus, as shown in FIG. 6C, the amount of rotation can be reduced by reducing the length of each bridging member and reducing the angle θ.

EXAMPLES

As an extreme example, consider holding the length l constant and varying the angle θ in a hypothetical series of different designs. In a first design, referring to FIG. 6A, as the angle θ approaches 0°, the bridging elements 140 approach an orientation parallel to the longitudinal axis of the stent. At this extreme, the bridging elements 140 have virtually no contribution to the radial strength of the stent. As the stent expands or contracts, assuming that the bridging elements 140 maintain their horizontal orientation, there is zero relative rotation between adjacent expandable ring members. Further, these horizontally oriented bridging elements inhibit bending flexibility.

Figure 6B:
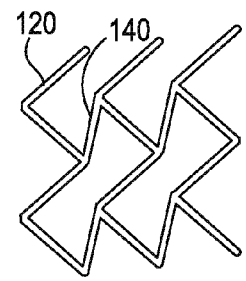
FIG. 6B shows a stent having bridge elements arranged substantially circumferentially.

In a second design, referring to FIG. 6B, as the angle θ approaches 90°, the bridging elements 140 approach a circumferential orientation. At this extreme, the bridging elements 140 have a significant contribution to the radial strength of the stent. Moreover, as the stent expands or contracts, the relative rotation between expandable ring members can be significant (it increases with increasing bridging element length). And at this extreme, the circumferentially oriented bridging elements 140 promote bending flexibility.

Stent Characteristics as a Whole

The stent 100 can be formed from a superelastic material. In one specific aspect, the superelastic material is Nitinol, an intermetallic compound having approximately 50.8 atomic percent Nickel and the balance Titanium. Nitinol has the unique properties of shape memory and superelasticity, and in this application is designed to take advantage of the material's ability to withstand unusually high levels of strain (up to 8% or more), without experiencing plastic deformation. The material can have an unusually pronounced hysteresis effect in its stress-strain relationship: when subjected to loading, stresses are relatively high, as they reach the upper plateau (UP) where a phase change from austenite to martensite occurs. When the material is unloaded, stresses are relatively low, as seen in the lower plateau (LP) where the material transforms from martensite to austenite. The magnitude of the difference between UP and LP stresses is determined by material composition, as well as thermal and processing history. In some embodiments, the transition temperature for the material, known as the Austenite Finish (Af) temperature is preferably set between 10 degrees and 37 degrees C. Preferentially, the Af temperature is set close to body temperature to maximize the hysteresis effect of the material, increasing the difference between UP and LP. As such, forces exerted by the stent as it unloads (expands) from its constrained state are minimized. This force, described as Chronic Outward Force (COF), is controlled by the LP stress. Conversely, the forces exerted by the stent when it is loaded (subjected to external compression) are maximized. This force, described as Radial Resistive Force (RRF), is controlled by the UP stress.

When all internal apices 122 of a stent are connected together through a bridging element 140, as shown in FIG. 1, the stent can be termed a "closed cell" strut. Advantageously, by having a "closed cell" as opposed to an "open cell" stent can prevent potential obstructions from prolapsing through the struts to compromise the lumen. Closed cell stents are also retrievable after partial deployment if initial placement is unsatisfactory, as they do not have any free edges (as in open cell stents) that can be caught on a delivery system during constrained retraction. Conversely, if a stent is "open cell," in which some internal apices are unconnected, the stent can move more freely for enhanced flexibility. In some embodiments, the modules of the stents described herein can be modified such that a closed cell architecture is provided in some stent regions and an open cell architecture is provided in other regions. For example, the areas of the stent expected to lie within the regions of localized constriction can have a closed cell architecture while other areas have an open structure.

Scaffolding Performance

Stents are typically placed within a lumen to restore patency of a compromised lumen, resolve obstructions caused by disease or anatomical formations, and thereby improve flow or function. Obstructions within the lumen are often irregular or non-uniform in nature, and consequently it is desirable for the stent to provide uniform support throughout its contact area with the vessel, and minimize the area of any unsupported regions. "Scaffolding performance" is a term used to describe the ability of a stent to serve this purpose. Cell size, the area bounded by a closed region of struts or bridges, is one measure of scaffolding performance. Minimum inscribed circle (MIC), the smallest circle (or more properly, sphere) that can fit through the structural elements of the stent, passing from inside its cylindrical form to outside, is another measure. Both cell size and MIC can vary as the stent is expanded, stretched, twisted, or otherwise deformed. Ideally, both are minimized throughout any expected loading conditions experienced by the stent. Scaffolding performance tends to improve with the number of bridging elements 140 and strut elements 120 around the circumference and along the length; more bridging elements 140 and strut elements 120 of a smaller size will provide more uniform coverage and support for small and irregular obstructions that the stent may appose in the lumen. Thus, as shown in FIG. 6C, the scaffolding performance with improve as the number of bridging and strut elements is increased, the length of each of the bridging and strut elements is decreased, and the angle θ of the bridging elements is increased.

Typically, designs that provide excellent scaffolding characteristics and outward support are also relatively axially stiff, and therefore experience high local strains with localized axial displacement, bend, or torsional loads. Conversely, designs that offer excellent axial and bend flexibility typically suffer from poor local scaffolding performance as local regions of the stent may flex apart to accommodate a bend, this same local flexion typically exposes a gap in scaffolding support, often at the very region where it is most needed. The stents described herein addresses each of the concerns to provide a superior platform for treatment of various anatomical areas of the body.

Advantageously, the properties of the stents described herein can be customized along the length of the device to correspond to the physiology that is common with a particular anatomy or condition. Thus, each stent can have multiple sections, each section including modules that are modified to have a particular property.

FIG. 6C shows a summary chart of the effect of several variables on the flexibility, stiffness, rotation, and scaffolding, where + indicates positive correlation, ++ indicates strong positive correlation, − indicates negative correlation, − indicated a strong negative correlation, and 0 indicates no influence. Thus, for example, to make a section more axially flexible, the bridging members 104 can include a greater number of bridge elements 140 circumferentially or have elements with a longer length, a higher pitch, a lower width, or a lower thickness. Likewise, expandable ring members 102 can have a greater number of strut elements 120 circumferentially, or have struts elements with a longer length, lower width, or lower thickness. To make a section more radially stiff, there can be fewer strut elements in the expandable ring member, or each strut element can have a shorter length, a greater width, or a greater thickness. Likewise, the bridging members 104 can have a lower number of bridging elements 140 circumferentially, or each bridging element 140 can have a greater length, a greater pitch, a greater width, or a greater thickness. To make a section less rotatable, the bridging elements can have a shorter length or a lower pitch. Scaffolding performance is improved by increasing the number of bridging and strut elements around the circumference and along the length, and minimizing the freedom of these elements to move apart from each other as the stent is expanded, placed in a bend, or otherwise deformed. These parameters can be adjusted and balanced so as to optimize the performance of the stent for a given indication.

The parameters shown in FIG. 6C can vary between sections of the stent in order to obtain the proper stent characteristics. In some embodiments, only one parameter is different between sections. In other embodiments, two or more parameters are different.

IVCS Stents

Chronic venous insufficiency (CVI) is a disease in which the function of the venous system is compromised. As a result of CVI, blood tends to pool in the lower extremities, and insufficient blood may be returned to the heart for re-oxygenation. The patho-physiology of CVI commonly involves veins of the lower extremities and/or pelvic area: the femoral veins, iliac veins, and inferior vena cava. CVI is associated with deep vein thrombosis (DVT), a condition resulting from clotting of stagnant blood in the deep vein system. Thrombotic occlusions in the lower extremities and/or pelvic area and DVT can likely progress into post thrombotic syndrome (PTS) where fibrotic thickening of the vein walls hardens the disease and will require more aggressive treatment to re-establish patency. CVI is also associated with varicose veins in the superficial venous system, a condition relating to incompetent venous valves. CVI is a progressive condition that can result in leg pain and swelling, edema, and ulcers of the leg or ankle.

Figure 7A:
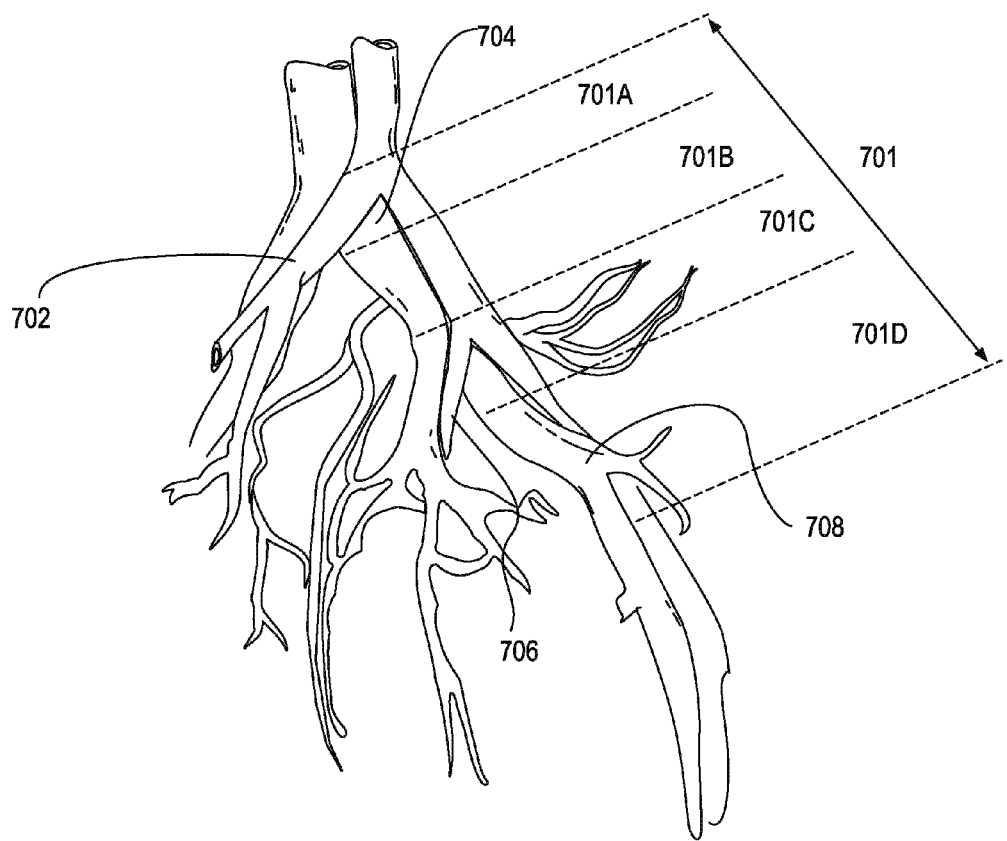
FIG. 7A is an illustration of the anatomy of the venous system within the pelvic region.
Figure 7B:
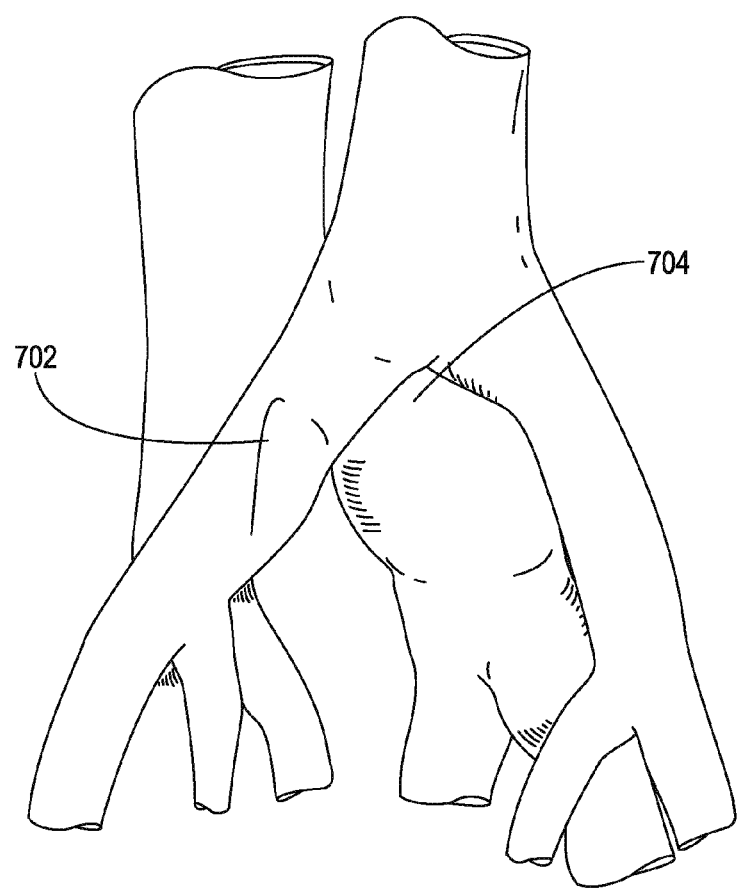
FIG. 7B is an illustration showing the spatial relationship of the anatomy of the right common iliac artery and the left common iliac vein whereby portions of the left common iliac vein are pinched by the right common iliac artery.
Figure 7C:
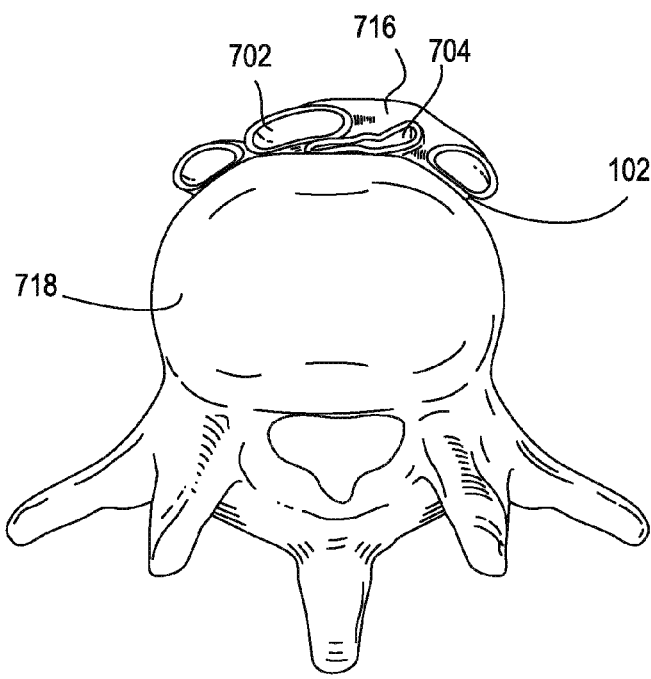
FIG. 7C is an illustration demonstrating the compression of the left common iliac vein between the spine and the right common iliac artery.

A condition known as iliac vein compression syndrome (IVCS), also known as May-Thurner syndrome, or pelvic spur syndrome is recognized as a cause of venous thrombo-occlusive disease. Referring to FIG. 7A, IVCS is commonly observed at the confluence of the common iliac veins, where the right common iliac artery 702 crosses the left common iliac vein (LCIV) 704. As shown in FIGS. 7B and 7C, the IVCS can cause compression of the LCIV 704 between the artery 716 and the spine 718. Symptomatic chronic nonmalignant obstructive lesions most commonly occur in region 701 between the confluence of the iliac veins to the inguinal ligament. Further, compression and consequent webbing or spurs are most common at region 701A where the right common iliac artery 702 crosses the left common iliac vein 704. A similar anatomical condition can occur at region 701C where the left internal iliac artery 706 crosses the left external iliac vein 708. In these regions, chronic pulsatile compression is believed to cause the formation of intraluminal venous webs or spurs. These anomalies have been described as chronic nonmalignant obstructive lesions.

Such obstructive lesions may be observed in clinical practice by diagnostic procedures including venography or intravascular ultrasound. It is believed that these lesions are an important contributor to the cascade of events leading to CVI of escalating severity. These lesions may be dilated by balloon venoplasty in an attempt to restore venous flow, but this technique has been found to provide inadequate resolution in many cases. Studies have found that treating these lesions with intravenous stents is a safe and effective therapy that is more durable than balloon venoplasty alone. To date, no stent has been designed specifically to treat obstructive lesions of the pelvic veins. Therefore, stents designed to treat the particular issues related to obstructive lesions of the pelvic veins are needed.

Figure 8:
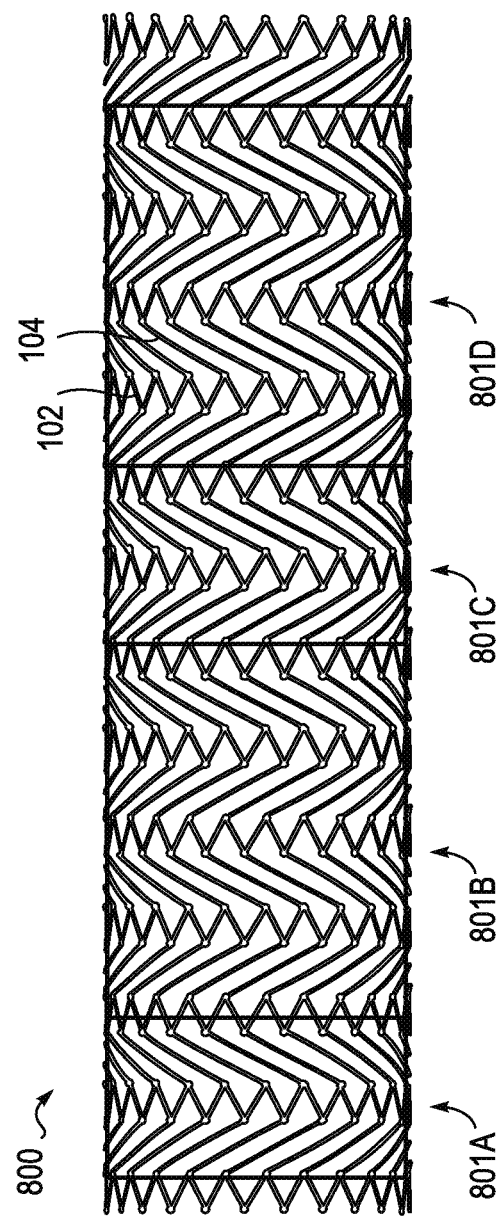
FIG. 8 shows an exemplary stent for treatment of IVCS.

Referring to FIG. 8, a stent 800 for treatment of IVCS may be preferentially designed by varying the parameters described herein. The stent 800 can have a length that covers the region 701, e.g., be at least 130 mm in length. The expanded diameter of the stent 800 can be between 8 mm and 20 mm, such as approximately 14 mm.

The stent 800 can include several expandable ring members 102 connected by bridging members 104. The stent can include sections 801A, 801B, 801C, and 801D that are configured to line up with regions 701A, 701B, 701C, and 701D, respectively, of the vein.

Section 801B can be configured to have a total length of between approximately 4-10 cm, such as 7 cm. Further, the strut elements 120 of the expandable ring members 102 in section 801B can have a length of between approximately 1-4 cm, such as 2.5 mm, a width of between approximately 0.1-0.3 mm, such as approximately 0.12 mm, and a thickness of between approximately 0.1-0.5 mm, such as approximately 0.36 mm. Moreover, the bridging elements 140 can have a length of between approximately 1-10 mm, such as 7 mm; a width of between approximately 0.07-0.3 mm, such as 0.1 mm; and a thickness of between approximately 0.1-0.5 mm, such as 0.36 mm, respectively. Lastly, there can be between 30-60 struts, such as 48 struts, in each expandable ring member 120, and the pitch of the bridging elements 140 can be between 20° and 70°.

Section 801A can be configured to maximize stiffness or resistance to compressive force in the region of the right common iliac artery compression 701A. Likewise, section 801C can be configured to maximize stiffness or resistance to compressive force in the region of the left internal iliac artery compressions 701C. For example, regions 801A and 801C can have 1.1 to 3 times the stiffness of region 801B, such as 2 times the stiffness of section 801B. The parameters shown in FIG. 6C can be different from one section to the next in order to obtain the proper stiffness. In some embodiments, only one parameter will be changed. In other embodiments, two or more parameters are changed.

In one embodiment, the length of the strut elements 120 in the expandable ring members 102 can be decreased and/or the width or thickness of the strut elements 120 can be increased in sections 801A and 801C relative to section 801B so as to maximize stiffness in those areas. The length of the strut elements 120 in sections 801A or 801C can be 5-50% lower than the length of the strut elements 120 in section 801B. For example, the length of the strut elements 120 in each expandable ring member 102 of sections 801A, 801C can be between 1 and 4 mm, such as approximately 2.1 mm. The width of the strut elements 120 in sections 801A and 801C can be 5-50% higher than the width of the strut elements 120 in section 801B. For example, the width of the strut elements 120 in each expandable ring member 120 of sections 801A, 801C can be between approximately 0.1 mm and 0.3 mm, such as approximately 0.16 mm. Likewise, the thickness of the strut elements 120 in sections 801A and 801C can be 5-50% higher than the thickness of the strut elements 120 in section 801B. For example, the thickness of the strut elements 120 in each expandable ring member 120 of sections 801A, 801C can be between approximately 0.1-0.5 mm, such as between 0.2 mm and 0.4 mm, such as approximately 0.36 mm.

In one embodiment, the length width, of the bridging elements 140 in the bridging members 104 in sections 801A and 801C can be increased and/or the angle θ can be increased relative to bridging members 104 in section 801B. Thus, the length, width, and/or thickness of the bridging elements 140 in sections 801A, 801C can be 5-50% greater than the length width, and/or thickness of bridging elements 140 in section 801B. For example, the bridging elements 140 can have a length between approximately 1-10 mm, such as 6 mm; a width between approximately 0.07-0.3 mm, such as 0.12 mm; and a thickness between approximately 0.1-0.5 mm, such as 0.36 mm.

The total lengths of each section 801A and 801C can be between 1 and 3 cm, such as 2 cm. Lastly, there can be 30-60, such as 48 struts, in each expandable ring member 120, and the pitch of the bridging elements 140 can be between 20° and 70°.

Section 801D can be configured to maximize flexibility in the region where the LCIV approaches or crosses the inguinal ligament (region 701D). For example, section 801D could be 1.1 to 3 times as flexible as section 801B, such as 2 times as flexible as section 801B.

In one embodiment, the flexibility of section 801D is increased relative to section 801B by increasing the length of the strut elements 120, decreasing the width of the strut elements 120, and/or decreasing the thickness of the strut elements 120. The difference between the length, width, and/or thickness of the strut elements of section 801D and section 801B can be between 5 and 50%. For example, the struts elements 120 of section 801D can have a length of approximately 1-4 mm, such as approximately 3 mm, a width of 0.1 and 0.3 mm, such as approximately 0.10 mm, and a thickness of between 0.1 and 0.5 mm, which as approximately 0.36 mm.

In one embodiment, the flexibility of section 801D is increased relative to section 801B by increasing the length of the bridging elements 140, decreasing the width of the bridging elements 140, and/or decreasing the thickness of the bridging elements 140. The difference between the length, width, and/or thickness of the bridging elements 140 of section 801D and section 801B can be between 5 and 50%. For example, the bridging elements 140 can have a length between 1-10 mm, such as 8 mm; a width between 0.07-0.3 mm, such as 0.08 mm; and a thickness between 0.1-0.5 mm, such as 0.36 mm, respectively.

Section 801D can have a length of approximately 3-5 cm, such as 4 cm. Lastly, there can be 30-60, such as 48 struts, in each expandable ring member 120, and the pitch of the bridging elements 140 can be between 20° and 70°.

In one embodiment, the total expanded circumference of the stent is 14 mm*π, or approximately 44 mm, and the circumferential component of the bridging member 104 of section 801D is approximately 4.4 mm. Thus, each bridge spans 4.4/44=10% of the circumference, or 360°*10%=36°, when the stent is in its expanded configuration. In the constrained condition, the circumference of this stent is 3.2 mm*π, or approximately 10 mm, so a bridge spans 4.4/10=44% of the circumference (this assumes the circumferential component of the bridge element stays the same), or 360°*44%=160°. Thus, as this stent is expanded or constrained, adjacent expandable ring segments in section 801D undergo rotation of the difference in the expanded and contracted angle, 160° minus 36°, or 124°.

These design parameters of section 801D are chosen so as to enhance flexibility without compromising scaffolding performance.

Femoral Artery Stents

Obstructive or occlusive arterial disease occurs when the natural lumen of an artery narrows or closes, such as when fibro-fatty deposits or calcified plaques grow within the layers of the artery. Consequences of coronary arterial disease may range from angina to myocardial infarction and sudden death.

Figure 9C:
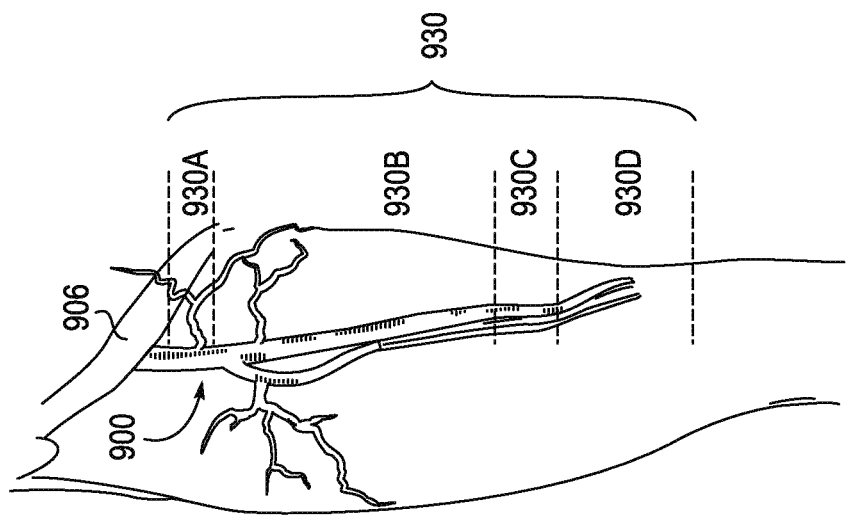
FIGS. 9A-9C show the femoral arteries and surrounding anatomy.
Figure 9B:
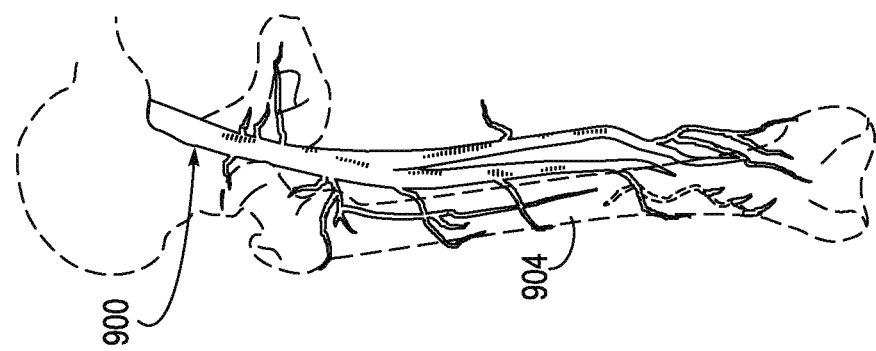
Figure 9A:
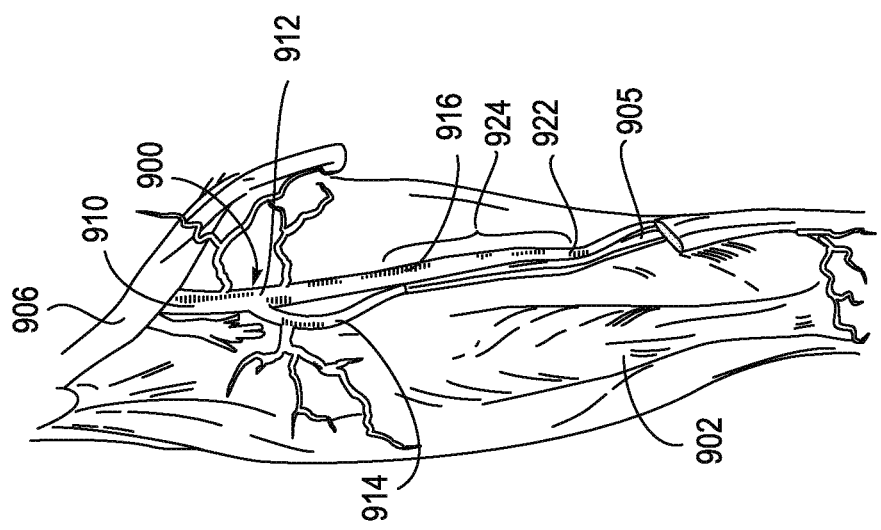

The superficial femoral artery (SFA) is commonly affected by peripheral arterial disease that may be associated with symptoms ranging from mild claudication and difficulty walking to chronic limb ischemia and partial amputation. FIGS. 9A-9C show the femoral arteries 900 in relation to surrounding muscles 902 and skeletal landmarks 904. As the external iliac artery passes posterior to the inguinal ligament 906, its name changes to the common femoral artery 910, which branches (at 912) into the profunda 914 and the superficial femoral artery 916. The profunda 914 supplies blood to the thigh and the superficial femoral artery 916 carries blood to the lower limb.

The SFA is unique in the human arterial system, as it traverses the thigh region with few branches, serving to deliver oxygenated blood to the lower limb by way of the popliteal and tibial arteries. Transiting from the region of the hip to the knee, the SFA passes through several muscle groups, and is subjected to one of most dynamic and mobile environments in the human anatomy. While disease in the SFA can be localized, it is frequently diffuse, commonly spanning 10 cm or more.

The superficial femoral artery is effectively pinned in two major locations: in area 930A near its origin in the area of the inguinal ligament 906 and where it branches into the profunda 914, and in area 930C near its terminus in the area of first genicular arteries 922 and the Hunters canal 924. Between these points, in region 930B, the vessel can be quite mobile, limited to some extent by minor branch vessels, often to a greater extent by rigid calcifications within the diseased regions of the vessel. The areas of the vessel that are less constrained—for example, the area 930B between the inguinal ligament and hunters canal and the area 930D, and away from areas of localized calcification—may be subjected to highly localized deformations including twisting, stretching, and/or compression with flexion of the limb.

The dynamic challenges of this disease prone area of the SFA create a severe fatigue environment for metallic implants intended to improve lumen diameter and distal perfusion. Stents placed in this region have commonly been found to fracture, raising concern about such implants failing to perform their function, creating injury, or causing additional risks to the patient. Accordingly, a stent that is capable of withstanding such an environment is needed.

Figure 10:
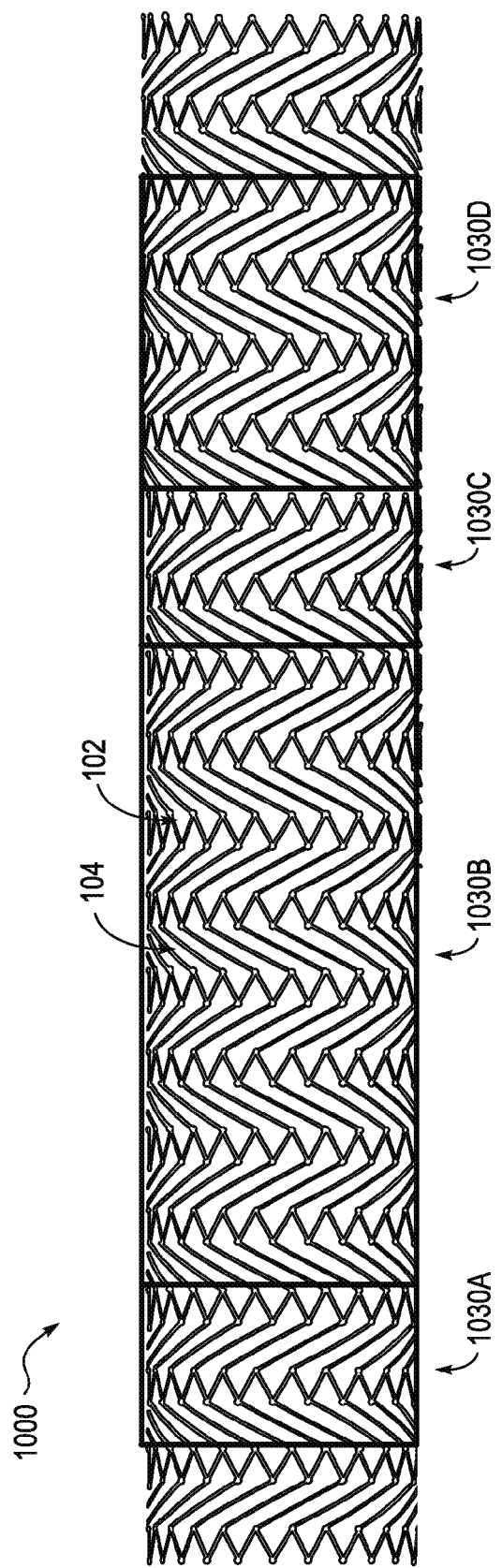
FIG. 10 shows an exemplary stent for a femoral artery.

Referring to FIG. 10, a stent 1000 for treatment of the femoral parties includes alternating circumferential bridging members 104 and expandable ring members 102. The stent can include sections 1030A, 1030B, 1030C, and 1030D that are configured to line up with regions 930A, 930B, 930C, and 930D, respectively, of the artery. Thus, the stent 1000 can have an expanded diameter of slightly more than the diameter of the femoral artery to provide sufficient outward force. For example, the stent 1000 can have an expanded diameter of 6-10 mm, such as approximately 8 mm.

The sections 1030A and 1030C intended to be placed in the pinned area of the adductor hiatus and canal can be configured to be of higher strength or stiffness relative to sections 1030B and 1030D. For example, the wall thickness can be increased relative to sections 1030B and 1030D and/or the ratio between the wall thickness and the strut width can be increased relative to sections 1030B and 1030D. The length of the strut members may be decreased to increase the hoop stiffness in this area. Furthermore, to increase the hoop stiffness in this area, the length and angle of the bridging elements may be increased.

Further, section 1030B of the stent 1000 that is intended to be placed in the highly mobile region 930B between the profunda 914 and the adductor hiatus (the termination of the Hunter's canal, 905) and in the mobile region 930D can be configured to be more flexible relative to sections 1030A, 1030C. For example, the alternating circumferential bridging members can be designed to allow increased flexibility by increasing the length and angle θ of bridging elements 140 in the bridging members 104 relative to sections 1030A and 1030C.

A femoral artery stent 1000 could vary in diameter from 6-10 mm, and vary in length from 20-150 mm. There could be 20 to 50 struts elements 120 in each expandable ring member 102. Further, the length, width and thickness of the strut elements 120 in each expandable ring member 102 can be between 1-4 mm, 0.05-0.2 mm, and 0.1-0.3 mm, respectively. Further, the length, width and thickness of the bridging elements 140 in the bridging members 104 can be between 1-10 mm, 0.03-0.2 mm, and 0.1-0.3 mm, respectively. The pitch of the bridging elements 140 can be between 20° and 70°.

Coronary Artery Stents

Figure 11:
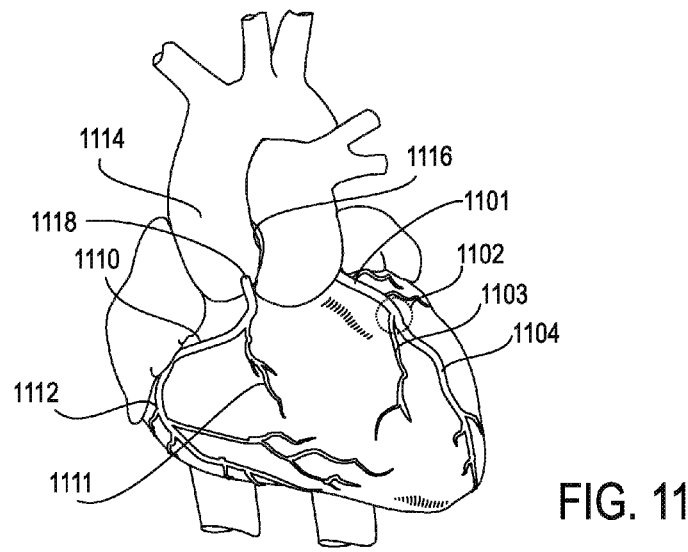
FIG. 11 shows the coronary arteries.

Coronary arterial disease is among the most important areas of interventional medicine. Traditionally, stenoses of the coronary arteries have been treated with balloon expandable stents because of their high strength, ease of use, and versatility. Referring to FIG. 11, the modular stent described herein could be useful in the coronary arteries, for bifurcation 1102 of the left main (LM) artery 1101 to the left anterior descending (LAD) artery 1104, the left main artery to the circumflex (CX) artery 1103, or in the region of side branches between right coronary artery (RCA) 1110, LAD 1104, or CX 1103 and corresponding diagonal branches along their length. Similarly, self expanding stents could be used for stenting the LM 1101 itself, and potentially the ostium of the LM 1116 and RCA 1118 at the location of the aortic root 1114. Particularly in these areas, it is critical that the stent accommodate significant variation in shape in-situ, i.e., the final contour of the implanted stent may need to be significantly non-cylindrical and include abrupt changes in local diameter or cross section.

Figure 12A:
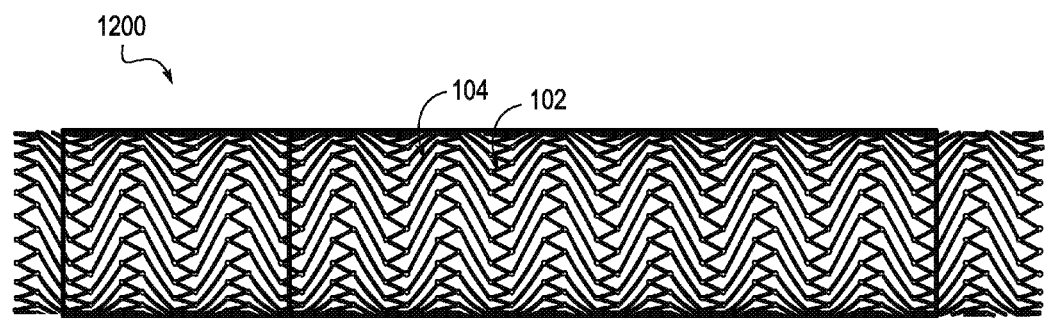
FIGS. 12A-12B show an exemplary stent for a coronary artery.
Figure 12B:
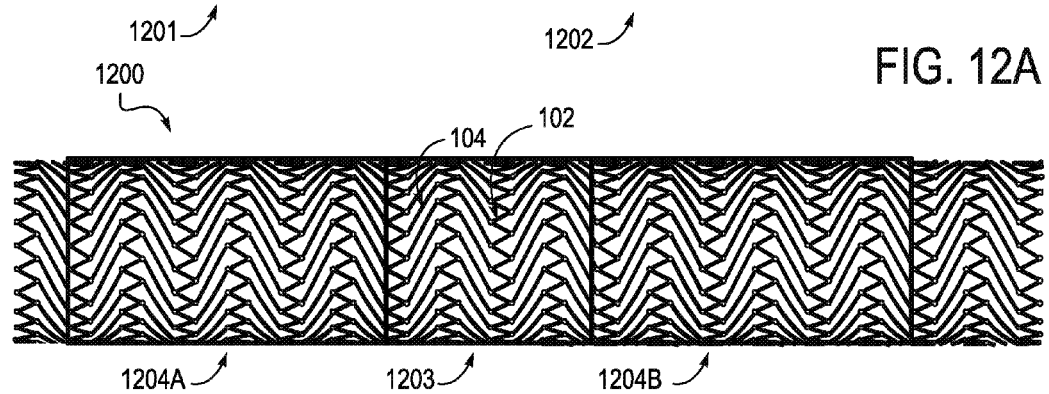

Referring to FIGS. 12A-12B, a stent 1200 for treatment of coronary artery disease includes alternating circumferential bridging members 104 and expandable ring members 102. The stent 1200 is configured to abruptly change one or more of its shape, contour, local diameter, or cross sectional profile to accommodate for the changes of the coronary arteries. In one embodiment, shown in FIG. 12A, the stent 1200 includes a section 1201 and a section 1202. Section 1201 can be configured to be positioned near an ostium or the origin of a branch vessel. Accordingly, section 1201 can be more flexible than section 1202. Thus, for example, the bridging elements of the bridging members 104 can be longer in section 1201 than in section 1202. Further, the pitch of the bridging members 104 in section 1201 can be increased relative to section 1202. Additionally, section 1202 can be configured to provide more uniform vessel support than section 1201 and/or can be configured to provide drug delivery to the remainder of the stented coronary artery. The shorter bridging elements and smaller pitch relative to section 1201 can provide increased support in section 1202.

In another embodiment, shown in FIG. 12B, the coronary artery stent 1200 includes a section 1203 between adjacent sections 1204A and 1204B. Section 1203 can be configured to be located at the site of a branch vessel, while sections 1204A and 1204B can be configured to be proximal and distal to the branch location. Accordingly, section 1203 can be configured to be more flexible than sections 1204A and 1204B. Thus, bridging elements 140 of the bridging members 104 in region 1203 can be longer and/or have a higher pitch than the bridging elements in regions 1204A and 1204B.

A coronary artery stent 1200 could vary in diameter from 2-3.5 mm, and vary in length from 8-33 mm. There could be 20 to 50 strut elements 120 in each expandable ring member 102. Further, the length, width and thickness of the strut elements 120 in each expandable ring member 102 can be between 0.5-1.5 mm, 0.03-0.0.08 mm, and 0.05-0.10 mm, respectively. Further, the length, width and thickness of the bridging elements 140 in the bridging member 104 can be between 0.5-4 mm, 0.01-0.06 mm, and 0.05-0.10 mm, respectively. The pitch of the bridging elements 140 can be between 20° and 70°.

Renal Artery Stents

Figure 13:
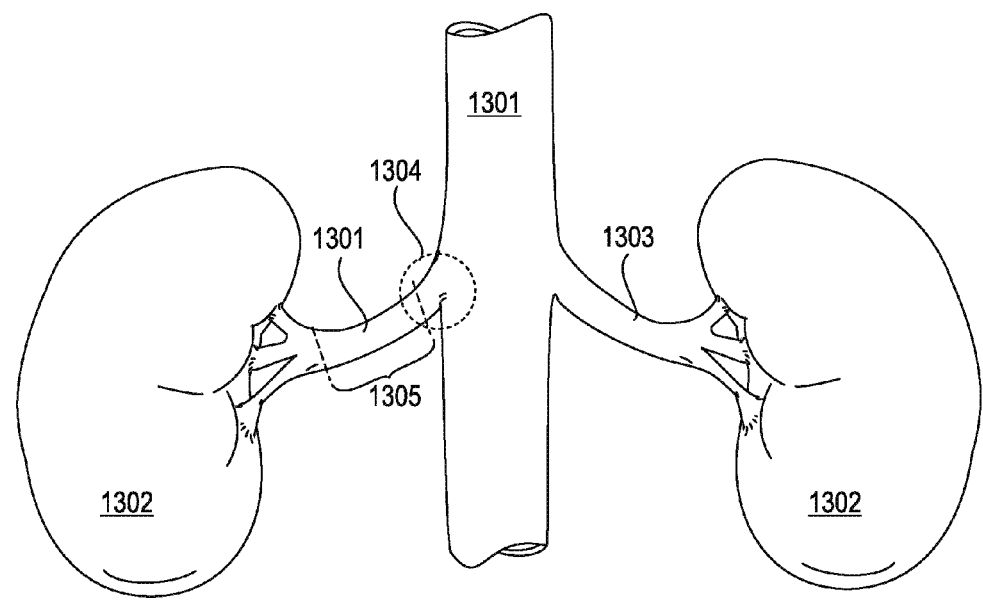
FIG. 13 shows the renal arteries.

Referring to FIG. 13, the renal arteries 1303 are prone to arterial disease, particularly in the ostium 1304. However, stenting can be difficult because the renal arteries 1303 are relatively mobile during the respiratory cycle. The kidney 1302 can move several millimeters during the respiratory cycle, while the aorta 1301 moves separately. The renal arteries 1303, joining the kidneys to the aorta, may therefore experience significant bending, angulation, or displacement between inhalation and expiration. Traditional inflexible stents may adversely impact the normal anatomy in this region, while flexible stents may experience large cyclic deformations and strains, potentially resulting in fracture. It is therefore important to provide a renal artery stent that can be sufficiently flexible, can accommodate the complex shape of the renal ostium, and can provide substantial radial stiffness for the body of the renal artery.

Figure 14:
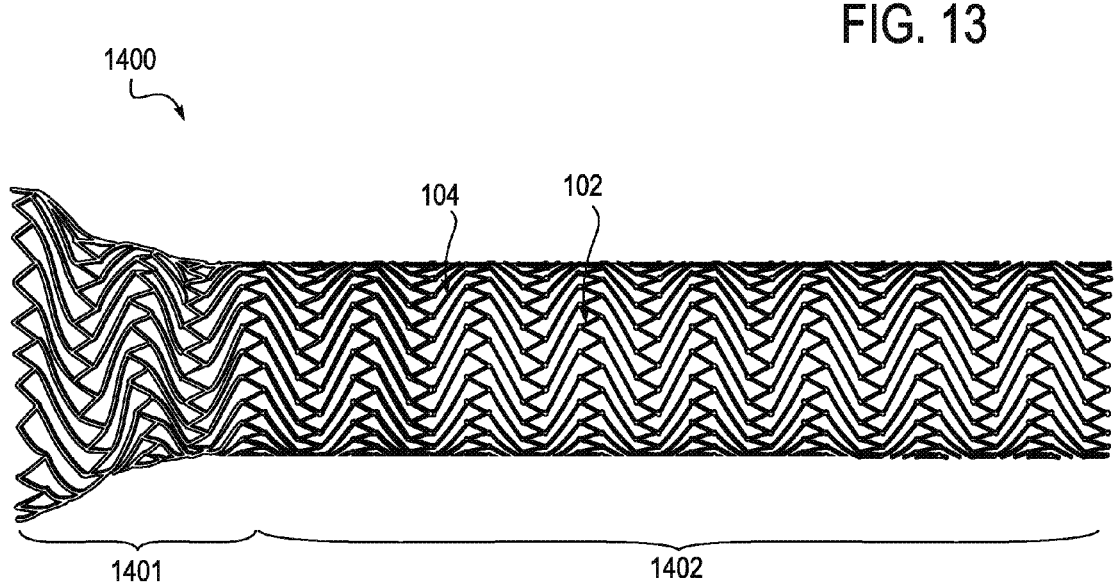
FIG. 14 shows an exemplary stent for a renal artery.

Referring to FIG. 14, a renal artery stent 1400 includes alternating circumferential bridging members 104 and expandable ring members 102. The stent includes a section 1401 configured to be placed at the ostial end of the rental artery and a section 1402 configured to be placed along the rest of the artery. Thus, section 1401 can be more flexible than section 1402 to accommodate the shape of the ostium. Conversely, section 1402 can be configured to provide higher strength or stiffness than section 1401 to adequately support the rest of the artery. Thus, for example, section 1401 can include longer bridging elements than section 1402, allowing for significant flaring of section 1401 to adequately cover the ostium 1304. Further, section 1402 can include shorter and stiffer struts than section 1401.

A renal artery stent 1400 could vary in diameter from 5-7 mm, and vary in length from 12-20 mm. There could be 20 to 50 strut elements 120 in each expandable ring member 102. Further, the length, width and thickness of the strut elements 120 in each expandable ring member 102 can be between 1-4 mm, 0.05-0.2 mm, and 0.1-0.3 mm, respectively. Further, the length, width and thickness of the bridging elements 140 in each bridging member 104 can be between 1-10 mm, 0.03-0.2 mm, and 0.1-0.3 mm, respectively. The pitch of the bridging elements 140 can be between 20° and 70°.

Carotid Artery Stents

Figure 15:
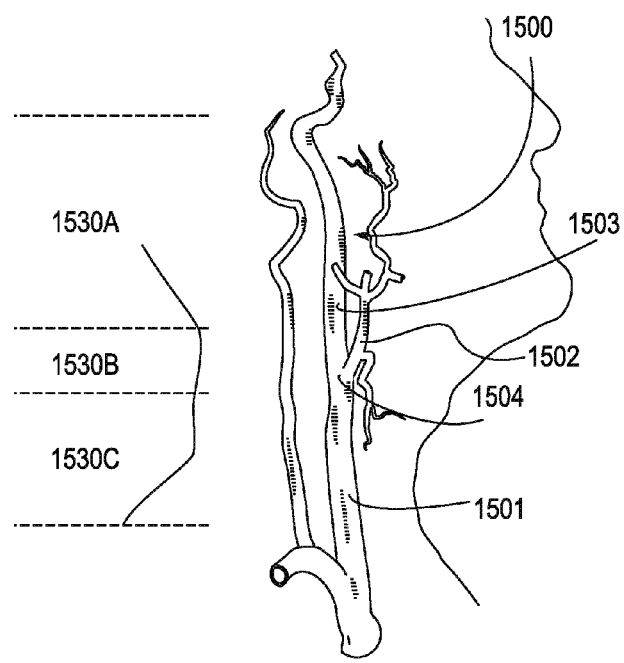
FIG. 15 shows the carotid arteries.

Referring to FIG. 15, the carotid arteries 1500 include the common carotid artery 1501, the internal carotid artery 1503, and the external carotid arteries 1502. The common carotid artery 1501 splits into the internal carotid artery 1503 which delivers flow to the brain, and external carotid arteries 1502 that deliver flow to the other areas of the head and face. The bifurcation 1504, where the common branches into the internal and external carotid arteries, is also described as the carotid bulb or carotid sinus. Carotid arterial disease commonly involves substantial plaque deposits and flow limiting narrowing in the common, and branch carotid vessels, and therefore commonly involves the sinus region. There are several important structures in the region 1530B of the carotid sinus including the baroreceptors in the adventitial layer of the carotid sinus. These baroreceptors are mechanoreceptors modulate the activity of the sympathetic and parasympathetic nervous systems on the basis of pressure and/or stresses in the vessel wall. Angioplasty and stenting in this region can create hemodynamic instability via stimulation of these baroreceptors, and consequent hypotension or hypertension. Conventional stents, with uniform outward force along the length of the structure, may exacerbate this effect. Accordingly, a stent is needed with enough support so support a lesion in the carotid artery, but enough flexibility to avoid hemodynamic instability.

Figure 16:
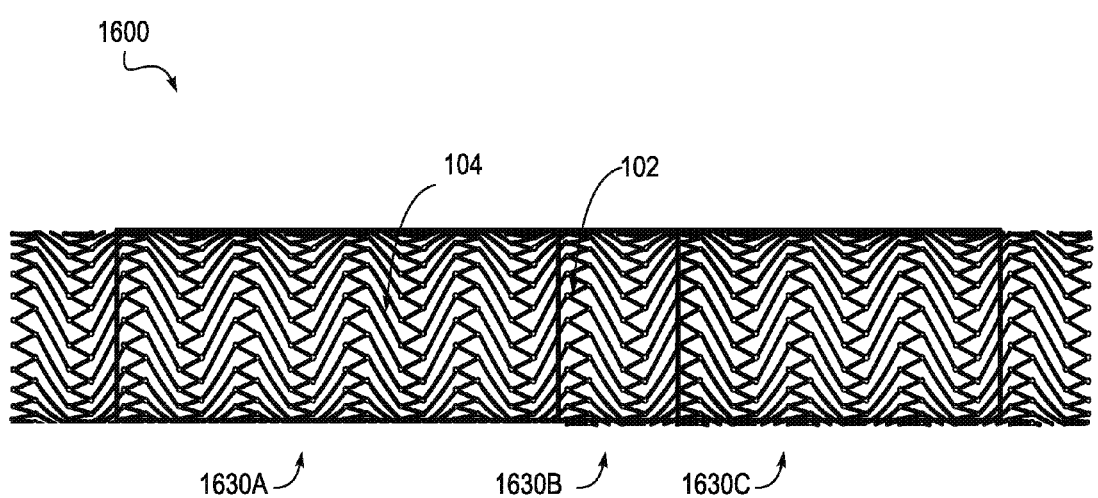
FIG. 16 shows an exemplary stent for a carotid artery.

Referring to FIG. 16, a carotid artery stent 1600 includes alternating circumferential bridging members 104 and expandable ring members 102. The stent includes sections 1630A, 1630B, and 1630C, which correspond to regions 1530A, 1530B, and 1530C, respectively, of the carotid artery. Region 1630B can be designed to allow for the abrupt change in diameter and shape in region 1530B while minimizing disruption of the carotid sinus. For example, the radial stiffness of section 1630B can be reduced and/or the flexibility of section 1630B can be increased relative to neighboring sections 1630A and 1630C. In addition, sections of the stent near side branches can be configured to be more flexible than other sections.

A carotid stent 1600 could vary in diameter from 4-10 mm, and vary in length from 20-60 mm. There could be 20 to 50 strut elements 120 in each expandable ring member 102. The length, width and thickness of the strut elements 120 in each expandable ring member 102 can be between 1-4 mm, 0.05-0.2 mm, and 0.1-0.3 mm, respectively. Further, the length, width and thickness of the bridging elements 140 in each bridging member 104 can be between 1-10 mm, 0.03-0.2 mm, and 0.1-0.3 mm, respectively. The pitch of the bridging elements 140 can be between 20° and 70°.

AV Graft and Fistula Stents

Arteriovenous (AV) fistulas are created to improve vascular access for hemodialysis patients. To create a fistula, a vascular surgeon joins an artery and a vein together via an anastamosis. Since this union bypasses the capillaries, blood flows rapidly through the fistula, enabling sufficient blood for flow hemodialysis to occur efficiently. Fistulas are usually created in the nondominant arm and may be situated on the hand, the forearm (in which the radial artery is anastomosed to the cephalic vein), or the elbow (usually a brachiocephalic fistula, where the brachial artery is anastomosed to the cephalic vein). While AV fistulas generally work well, they can close over time or develop aneurysms, thus a stent-graft could be used to prevent these complications.

Figure 17A:
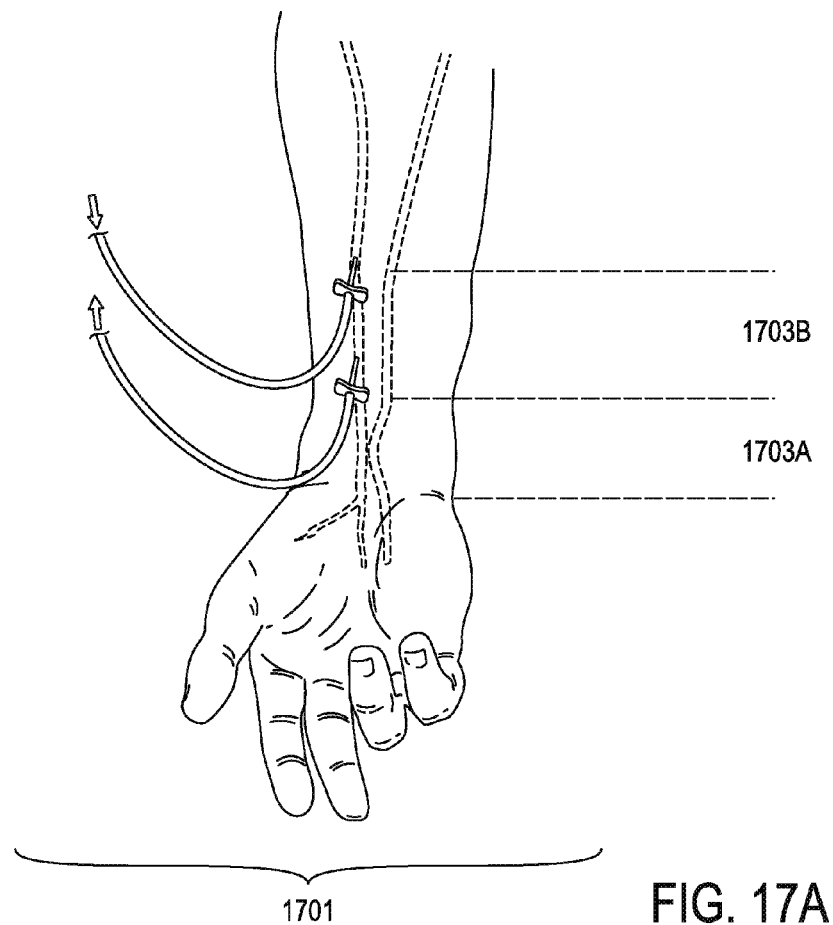
FIGS. 17A-B show hemodialysis access grafts and fistulae.
Figure 17B:
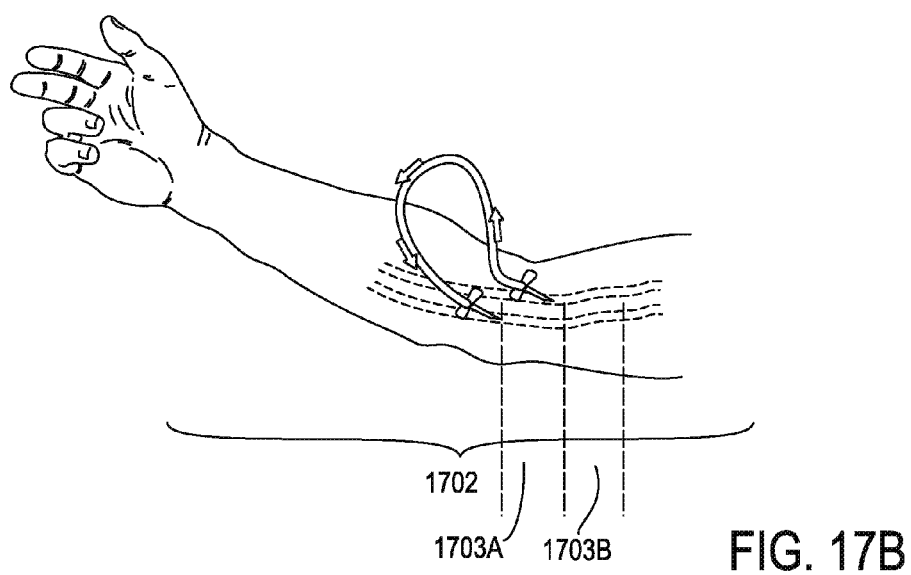

Referring to FIGS. 17A and 17B, the stent described herein could be used at the junction of hemodialysis fistulae 1701 or grafts 1702. Section 1703A of FIGS. 17A, 17B corresponds to the region where the fistula occurs or where the graft joins the native artery. Section 1703B of FIGS. 17A, 17B corresponds to the region of the native vessel. In these applications, a stent may need to be placed at the junction of an artery, vein, and/or synthetic graft, and therefore assume an abrupt angle. Furthermore, the stent may have to accommodate a significant diameter change at the site where the fistula or graft joins the native artery, making the modular stent described herein advantageous over traditional stents.

Figure 18:
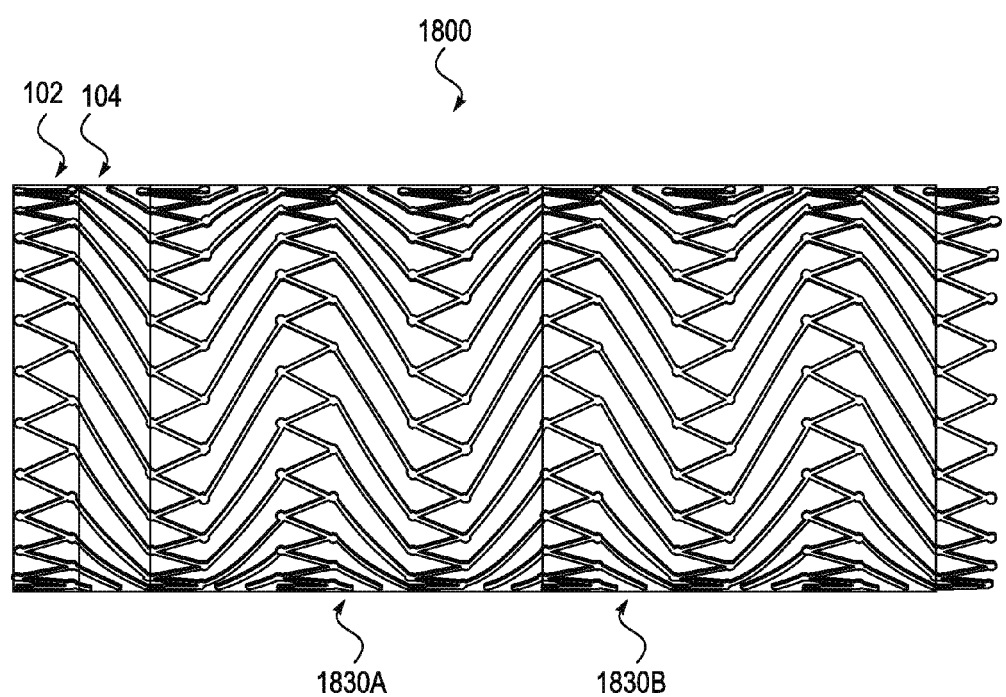
FIG. 18 shows an exemplary stent for a fistula.

Referring to FIG. 18, a fistula stent 1800 includes alternating circumferential bridging members 104 and expandable ring members 102. The stent includes sections 1830A and 1830B, which correspond to regions 1703A and 1703B, respectively. Region 1830A can be designed to correspond to region 1703A and thus allow for the abrupt change in diameter and shape or may need to assume an abrupt angle where the fistula or graft joins the native artery. For example, the radial stiffness of section 1830A can be reduced and/or the flexibility of section 1830A can be increased relative to neighboring section 1830B.

A fistula stent 1800 could vary in diameter from 5-10 mm, and vary in length from 20-80 mm. There could be 20 to 50 strut elements 120 in each expandable ring member 102. Further, the length, width and thickness of the strut elements 120 in each expandable ring member 102 can be between 1-4 mm, 0.05-0.2 mm, and 0.1-0.5 mm, respectively. Further, the length, width and thickness bridging elements 140 in each bridging member 104 can be between 1-10 mm, 0.05-0.2 mm, and 0.1-0.5 mm, respectively. The pitch of the bridging elements 140 can be between 20° and 70°.

Tracheal Stents

Figure 19A:
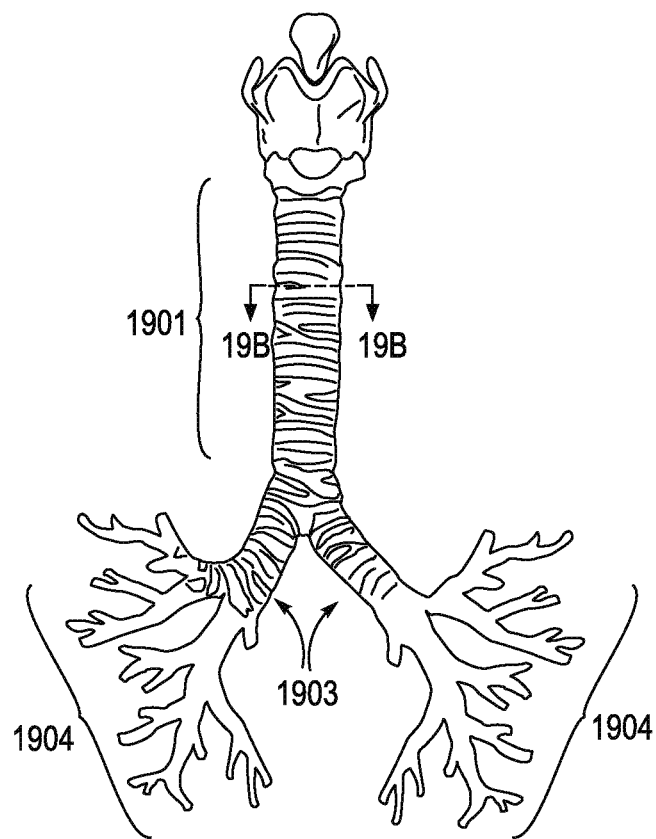
FIGS. 19A-19B show the trachea and bronchi.
Figure 19B:
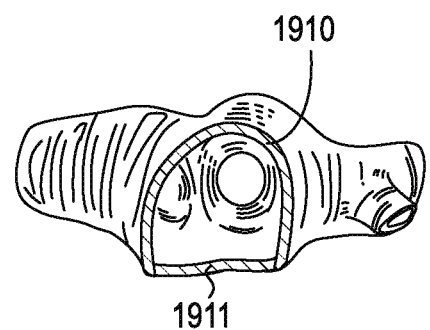
Figure 20A:
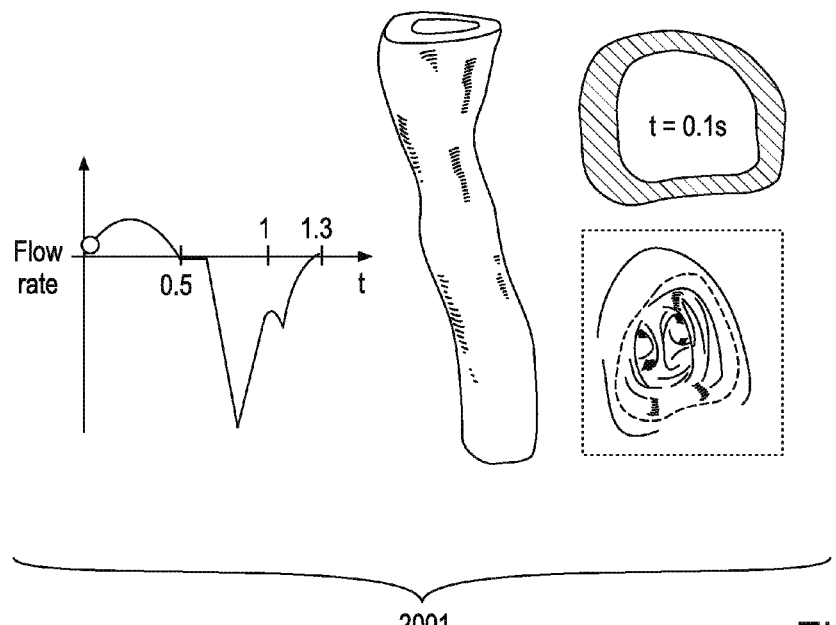
FIGS. 20A-20B show the response of the trachea during coughing.
Figure 20B:
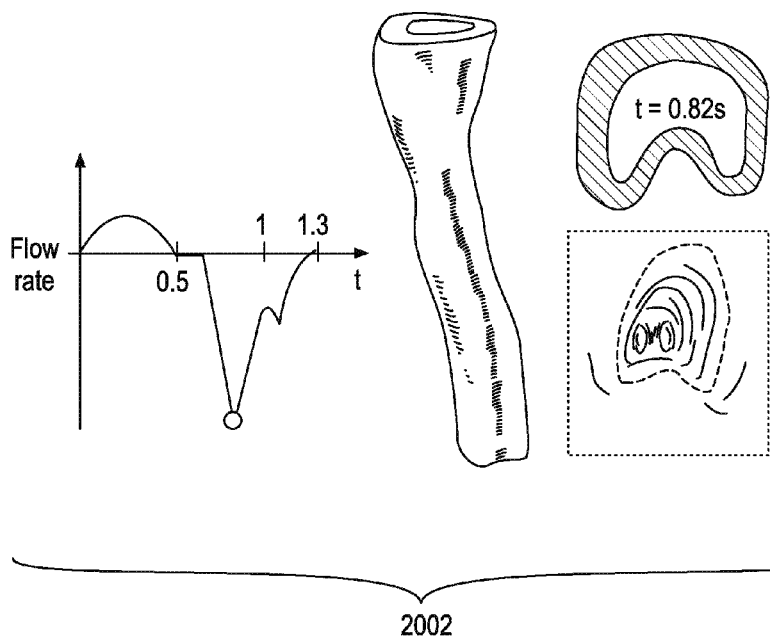

Referring to FIGS. 19A-19B, the trachea 1901 branches into the right and left main stem bronchi 1903, which further branch into lobar bronchi 1904 to feed the lungs. The main stem and lobar bronchi are circumferentially supported by irregular plates of hyaline cartilage. In the main stem, lobar bronchi and below, the cartilage 1910 is partially circumferential, taking the shape of the letter "C," with a fibrous membrane 1911 between the ends of the "C." When foreign matter, phlegm, or other debris becomes lodged in the bronchi or trachea, a cough reflex is triggered. The response of the human trachea during a cough is illustrated in FIGS. 20A-20B. When a cough occurs, the soft tissue in this region allows the substantially circular cross section of the trachea 2001 to collapse into a narrowed crescent shaped channel 2002. The reduced cross sectional area increases the velocity of the air exiting the lungs through this space, helping to propel material out of the trachea. The airways may become obstructed in the case of tumor growth in the region of the lungs or surrounding structures, causing compression of infiltration of the bronchi or trachea.

Stents can be placed in the trachea as a palliative or restorative therapy. Such a stent may provide outward forces to expand the lumen of the airways, prevent compression and/or ingrowth of the tumor, and/or deliver chemotherapeutic or other agents locally. Stents commonly used in this indication have several shortcomings. For example: silicone or polymer based stents have low outward force and can migrate or be expectorated; other stents designed primarily for cardiovascular use have been deployed with limited success, as these devices lack sufficient radial stiffness, thus allowing undesirable compression. Importantly, conventional stents are typically designed to have uniform radial outward forces along the length of the stent, which creates an incompatibility with the normal physiological and/or biomechanical movement of the airway. Furthermore, conventional stents may interrupt or degrade the normal mucociliary transport system of the bronchi and trachea with struts or coverings that are oriented in such a way as to inhibit the normal flow of mucus. Accordingly, a stent is needed that addresses some or all of these limitations.

Figure 21:
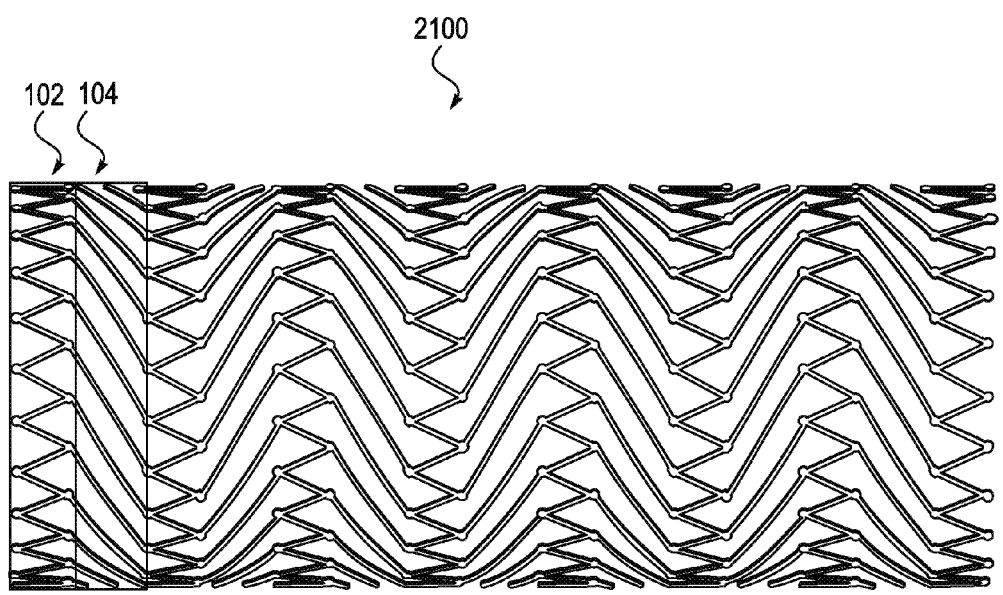
FIG. 21 shows an exemplary stent for a trachea.

Referring to FIG. 21, a tracheal stent 2100 includes alternating circumferential bridging members 104 and expandable ring members 102. The circumferential bridging member 104 could accommodate the need for the airways to transform between a substantially circular cross section to a substantially crescent shaped cross section during a cough. For example, an array of struts axially aligned in a circumferential band ranging up to 180 degrees of the circumference, and oriented toward the dorsal aspect of the airway, can be designed to be more flexible than the struts in an axial band oriented toward the ventral aspect of the airway. The normal configuration of the mucosal epithelium is spiral in nature. Further, the smooth muscle surrounding the airways tissue is arranged in a helical orientation. The epithelium and cilia follow the orientation of the innermost smooth muscle layer. In a preferred embodiment of the present invention, the circumferential bridge elements are oriented in such a way as to be consistent with this orientation. As such, an embodiment for this indication may favor circumferential bridges that are all oriented in the same direction, rather than alternating in direction along the length. Furthermore, the bridges are preferentially oriented in a direction that is closer to axial than circumferential, thus promoting functional mucociliary transport.

A tracheal stent 2100 could vary in diameter from 11-20 mm, and vary in length from 30-110 mm. For example, there can be 20 to 50 strut elements 120 in each expandable ring member 102. Further, the length, width and thickness of the struts elements 120 in each expandable ring member 102 can be between 2-8 mm, 0.1-0.5 mm, and 0.15-0.21 mm, respectively. Further, the length, width and thickness of bridging elements 140 in each bridging member 104 can be between 2-10 mm, 0.07-0.5 mm, and 0.15-0.21 mm, respectively. The pitch of the bridging elements 140 can be between 20° and 70°.

Neurovascular Stents

Figure 22:
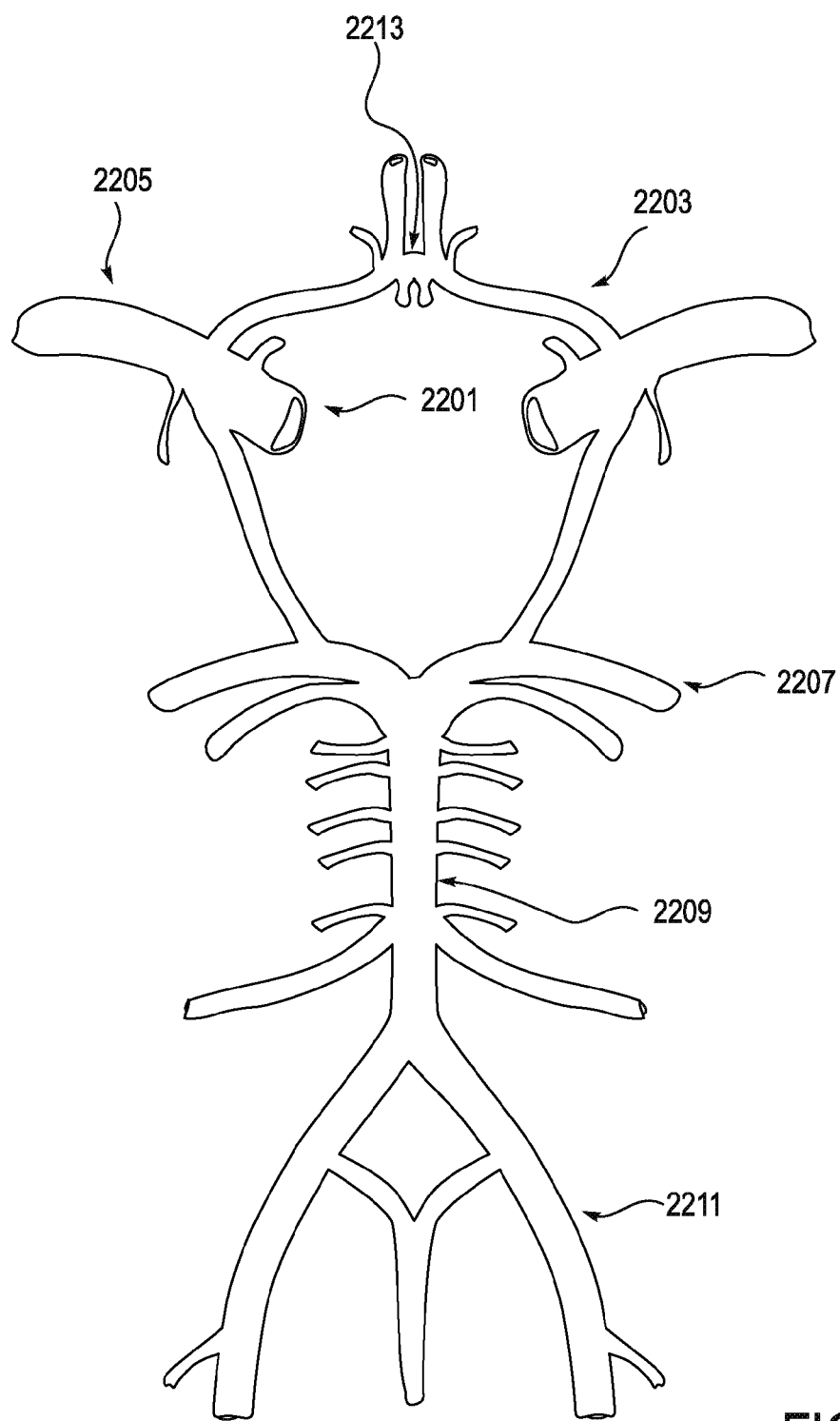
FIG. 22 shows part of the neurovascular system.

Atherosclerotic lesions are common in the cerebral vasculature of older adults. FIG. 22 shows common sites of cerebral atherosclerotic lesions, including the internal carotid arteries 2201, the anterior 2203, middle 2205, and posterior 2207 cerebral arteries, the basilar artery 2209, the vertebral arteries 2211, and the anterior communicating artery 2213. If a stenosis becomes severe enough, the blood flow to distal tissues can be compromised over time. More importantly, though, the thin fibrous cap on these atherosclerosis lesions can rupture, leading to clotting at the site of rupture. These clots can then travel downstream, and block blood flow to cerebral tissues, causing ischemic stroke. Indeed, intracranial stenosis account for about 5-10% of ischemic strokes. Atherosclerotic lesions that are prone to rupture are sometimes referred to as vulnerable plaques.

While anti-thrombotic therapy is generally the first choice for preventing ischemic stroke originating from atherosclerotic lesions, stenting is becoming a more popular choice for patients who have failed anti-thrombotic therapy. Indeed, atherosclerotic stenosis can be alleviated, and the risk of rupture can be reduced, by placing a stent across the lesion. However, cerebral stents must be carefully designed, as arterial rupture and dissection is more likely in the intracranial arteries compared to the extracranial arteries because of the weak muscularis and adventitial layers. In fact, some studies recommend undersizing a stent—making a stent that is smaller than native non-stenotic adjacent arteries—when treating stenosis in order to avoid rupture or dissection. The cerebral arteries vary widely in diameter and length thus a variety of sizes much be considered when designing a neurovascular stent.

Figure 23:
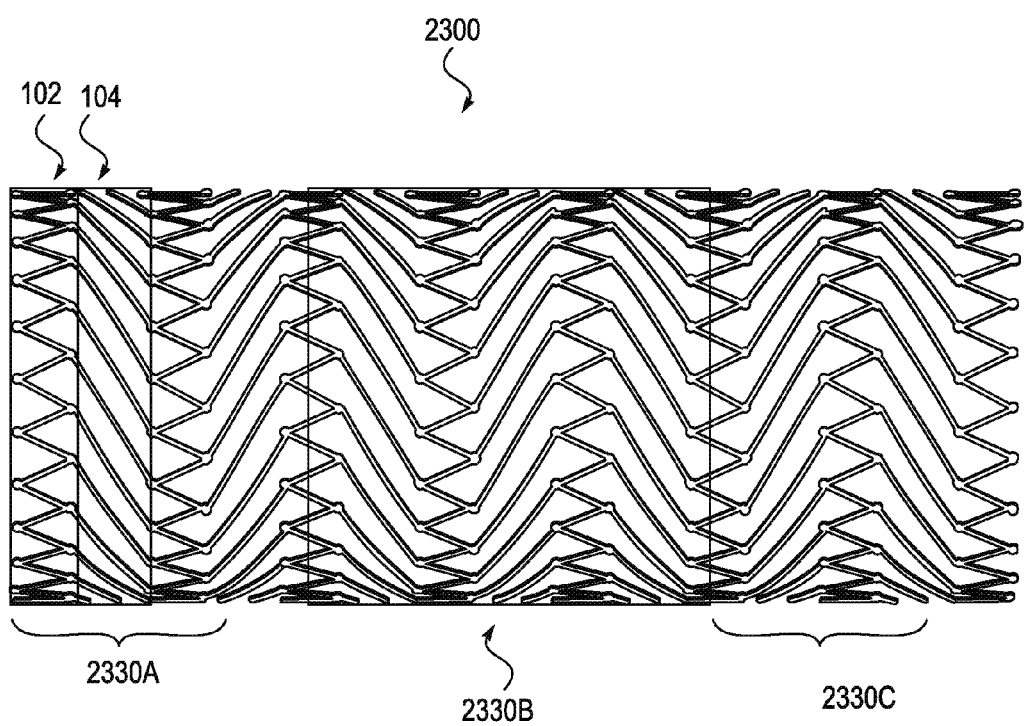
FIG. 23 shows an exemplary stent for a neurovascular system.

Referring to FIG. 23, a neurovascular stent 2300 includes alternating circumferential bridging members 104 and expandable ring members 102. A neurovascular stent 2300 must be designed to provide enough outward radial force to open up a cerebral atherosclerotic lesion, but not too much radial force to cause potentially fatal rupture of dissection. Thus the center section 2330B may be configured to be of a lower radial stiffness and more flexible than the end sections 2330A and 2330C in order to gently compression the lesion without rupture or dissection. Thus, in section 2330B, the length of the struts in the bridging member 104 and the expandable ring member 102 may be longer, and the width and thickness of these struts may be smaller compared to sections 2330A and 2330C. In fact, as mentioned earlier, it is possible that neurovascular stents would need to be undersized to avoid rupture or dissection.

A neurovascular stent 2300 could vary in diameter from 2-7 mm, and vary in length from 5-100 mm. For example, there can be 10 and 30 strut elements 120 in each expandable ring member 102. Further, the length, width and thickness of the strut elements 120 in each expandable ring member 102 can be between 0.5-1.5 mm, 0.03-0.08 mm, and 0.04-0.10 mm, respectively. Further, the length, width and thickness of the bridging elements 140 in each bridging member 104 can be between 0.5-4 mm, 0.01-0.06 mm, and 0.04-0.10 mm, respectively. The pitch of the bridging elements 140 can be between 30° and 60°.

Esophageal Stents

Figure 24:
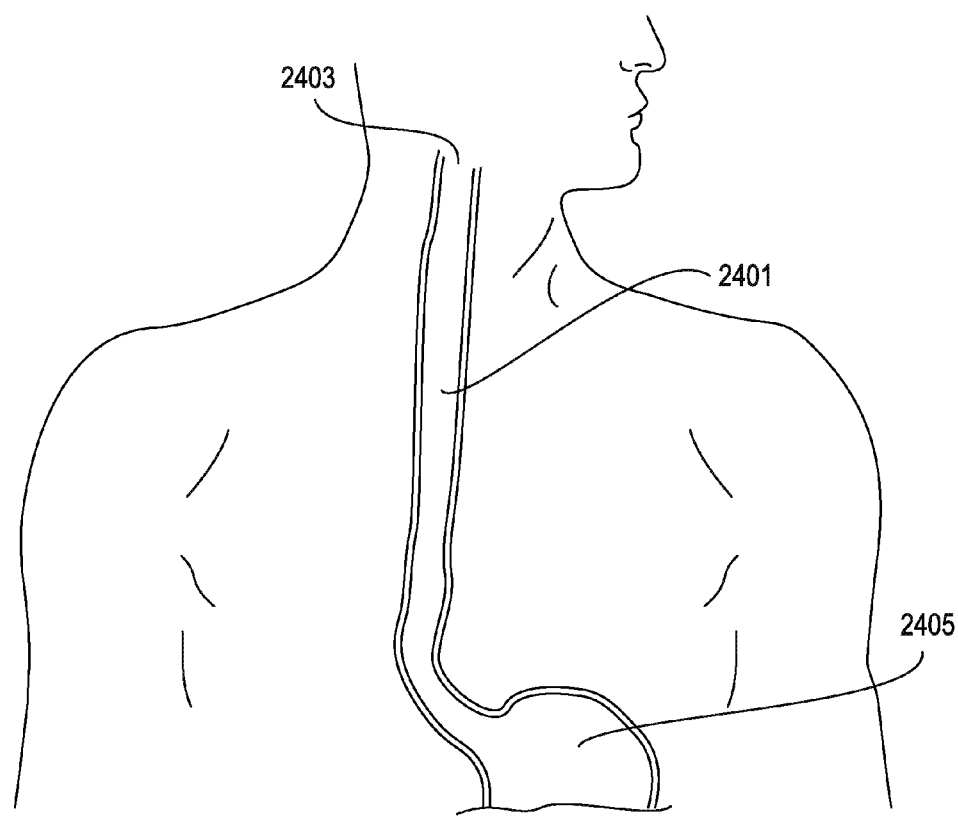
FIG. 24 shows an esophagus and surrounding anatomy.

Referring to FIG. 24, the esophagus 2401 is a muscular tube through which food passes from the pharynx 2403 to the stomach 2405. During swallowing, peristalsis pushes food down the esophagus into to the stomach. Benign or malignant lesions of the esophagus can prevent the passage of food into the stomach. Esophageal stenting can gently reopen the esophagus, leading to improved patency. In the case of malignant lesions, stenting is usually palliative, and may allow the patient to continue to consume food orally rather than through a feeding tube. Esophageal stenting can sometimes cause compression of the trachea, thus concomitant stenting of the trachea is often performed. Self-expanding stents are well-suited for the esophagus, as stent expansion that is too forceful may lead to tearing or fistulae. Esophageal stents need to have a low enough radial stiffness to allow peristalsis to occur, but must also exert sufficient radial outward force to avoid migration into the stomach. Lastly, a closed-cell design is beneficial so the device can be recaptured in the event of migration into the stomach.

Figure 25:
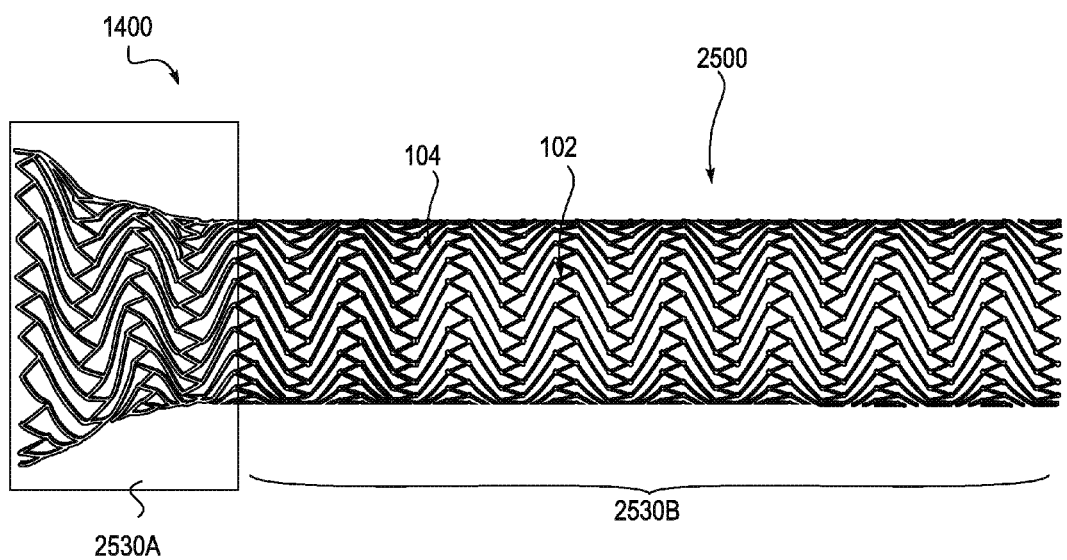
FIG. 25 shows an exemplary stent for an esophagus.

Referring to FIG. 25, an esophageal stent 2500 includes alternating circumferential bridging members 104 and expandable ring members 102. An end section 2530A may be flared and less radially stiff relative to the rest of the stent 2530B to accommodate the opening to the stomach 2405.

An esophageal stent 2500 could vary in diameter from 16-23 mm, and vary in length from 90-150 mm. For example, there can be 20-50 strut elements 120 in each expandable ring member 102. Further, the length, width and thickness of the strut elements 120 in each expandable ring member 102 can be between 2-8 mm, 0.1-0.5 mm, and 0.15-0.21 mm, respectively. Further, the length, width and thickness of the bridging elements 140 in each bridging member 104 can be between 2-10 mm, 0.07-0.5 mm, and 0.15-0.21 mm, respectively. The pitch of the bridging elements 140 can be between 20° and 70°.

CVS Stents

Figure 26:
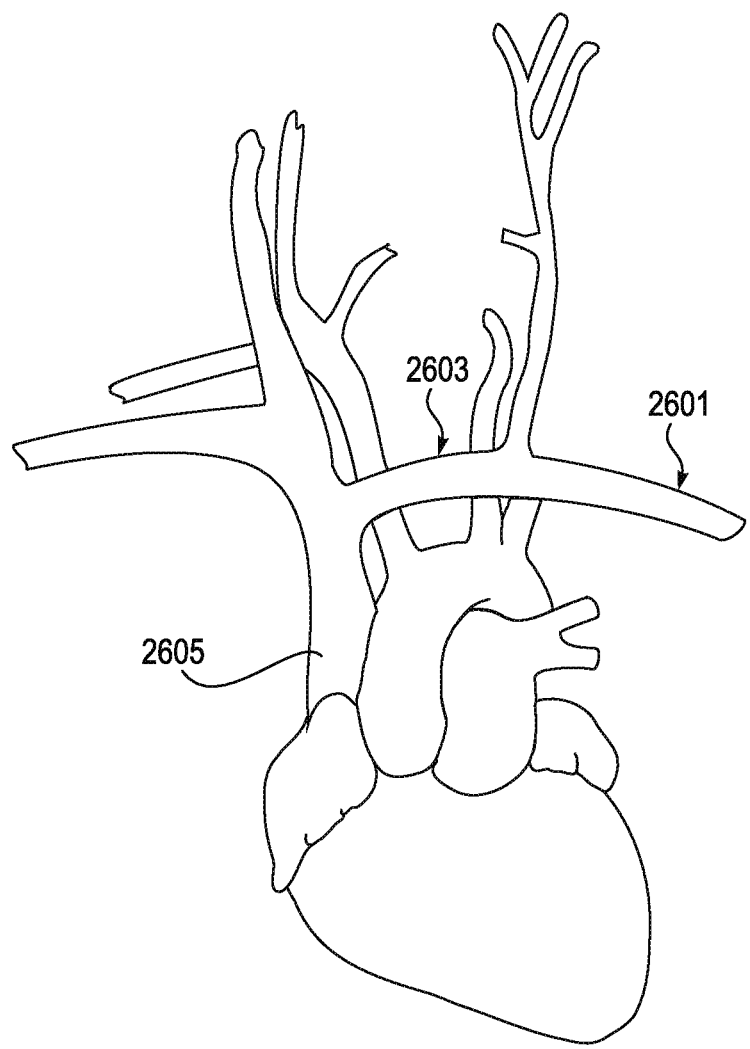
FIG. 26 shows the subclavian vein, the brachiocephalic vein (innominate vein), and the superior vena cava.

Referring to FIG. 26, Central Vein Stenosis (CVS) refers to a significant stenosis in a large intrathoracic vein, including the subclavian vein 2601, the brachiocephalic vein (innominate vein) 2603, and the superior vena cava 2605. CVS may be due to a variety of causes, both acute and chronic. In the acute case, spontaneous vein thrombosis involves compression of the axillary-subclavian vein, stasis of blood, and hypercoagulability. This condition is referred to as Paget-von Schrotter syndrome and also known as "effort-induced thrombosis." In the chronic case, axillary-subclavian-brachiocephalic veinprevious catheter placement for hemodialysis causes changes to venous hemodynamics, resulting in thrombus formation and venous obstruction, eventually culminating in total occlusion. Endovascular treatment for CVS includes balloon angioplasty and stenting to re-establish blood flow and prolong patency.

Figure 27:
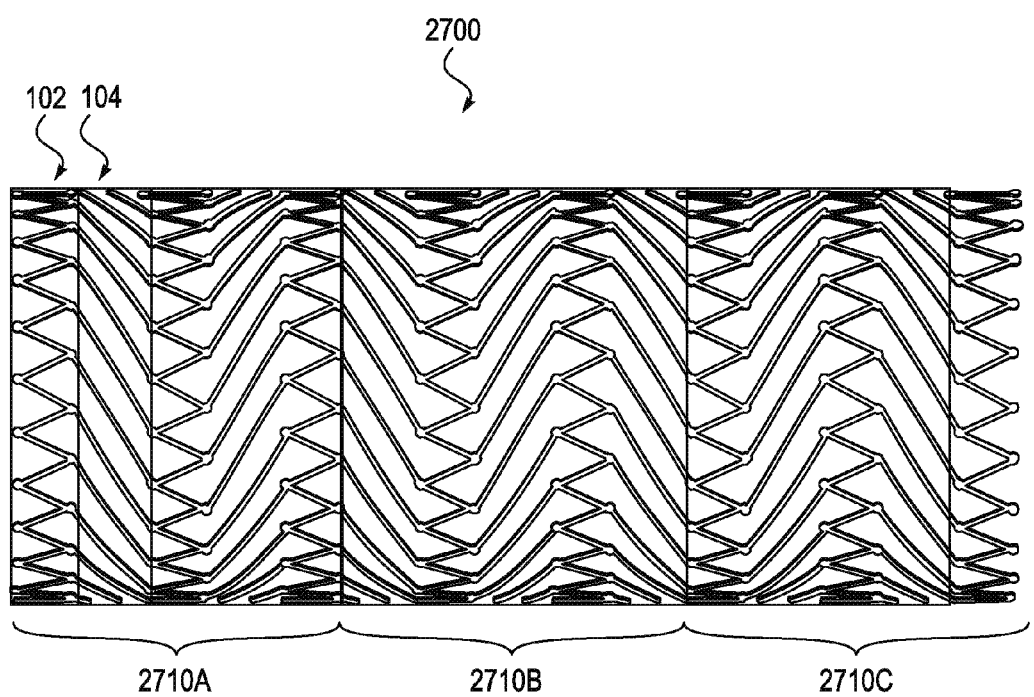
FIG. 27 shows an exemplary stent for the subclavian vein, brachiocephalic vein, and the superior vena cava.

Referring to FIG. 27, a stent 2700 having alternating circumferential bridging members 104 and expandable ring members 102 as described herein could be used to treat CVS. The CVS stent 2700 can include a first section 2710A and a second section 2710B. The strut elements 120 in the expandable ring members 102 could be shorter or wider in Section 2710B compared to adjacent sections in order to increase the radial stiffness and support the stenosis, thrombosis, or other compression in this region. Furthermore, in sections 2710A and 2710C, the bridging elements 140 in the bridging members 104 could be longer and thinner than adjacent sections in order to accommodate flexion of the shoulder. The stent 2700 could be configured to be placed in the transition from the superior vena cava 2605 to the subclavian vein 2601 and/or in the transition from the superior vena cava 2605 to the brachiocephalic vein 2603.

The CVS stent 2700 could vary in diameter from 8-16 mm, and vary in length from 20-100 mm. There could be 20 to 60 struts elements 120 in each expandable ring member 102. Further, the length, width and thickness of the strut elements 120 in each expandable ring member 102 can be between 1-4 mm, 0.1-0.3 mm, and 0.1-0.5 mm, respectively. Further, the length, width and thickness of the bridging elements 140 in the bridging members 104 can be between 1-10 mm, 0.05-0.3 mm, and 0.1-0.5 mm, respectively. Further, the pitch of the bridging elements 140 could be between 20° and 70°.

Customized Stents

The modular stents described herein can be used in a variety of different anatomies. As shown in FIG. 28, various characteristics of the stents can be modified to make such a stent optimal for the given anatomy.

Although various specific embodiments or examples have been described herein, it is to be understood that other combinations are possible. For example, the dimensions and relative values provided in the tables of FIG. 28 and FIG. 6C can be used to determine the relative dimensions of the sections of a particular stent. That is, if a first section is noted as requiring a particular flexibility, stiffness, change in diameter, or scaffolding performance relative to a second section, then the relative relationship between the stent characteristics (number, length, width, or thickness of the bridging elements or strut elements or the angle theta) of the various sections can be determined from FIG. 6C. In much the same way, the information detailed in FIG. 28 can be used to determine the dimensions based upon the relative stent characteristics. For example, if a particular stent characteristic is required to be "higher" in the first section than the second section, this can be read to mean that the characteristic is in the top ⅔, such as the top ½, for example, the top ⅓ or the top ¼ of the ranges provided in FIG. 28, while the same characteristic for the second section could be in the bottom ⅔, such as the bottom ½, for example, the bottom ⅓ or the bottom ¼ of the ranges provided in FIG. 28. Further, for any of the examples described herein, if one characteristic is said to be higher or lower in a first section than a second section, the characteristic can differ by approximately 5-50% from the first section to the second section. In summary, the various design details provided in FIGS. 6C and 28 may be used cooperatively to detail numerous alternative embodiments according to the various inventive aspects described herein.

Methods of Use

In operation, the stents described herein can be placed in the anatomy of interest. In some embodiments, the physician can use an imaging technique, such as injection of a radiopaque contrast medium into the anatomy of interest or ultrasonic techniques to visualize the path and caliber of the subject vessels. Using the imaging techniques, the physician can place a high pressure balloon at the site of the constriction and inflate to a pressure sufficient to dilate the narrowed area. This procedure may be repeated multiple times and at multiple locations to achieve a satisfactory result.

The stent can be constrained within a flexible sheath, preferably such that the sheath is compatible with an introducer sheath having a minimal profile. In some embodiments, the stent is constrained within this sheath at the time of manufacturing and packaging. Alternatively, the stent can be constrained within a capsule that is packaged separately from the delivery sheath, and coupled with the delivery device before insertion into the patient.

The physician can place a guidewire across the site of the target vessel. The delivery system can then be advanced over the guidewire to the target site. The stent can be positioned in the desired location using X-Ray and/or ultrasound guidance.

An actuation mechanism at the proximal end of the delivery system can then be used to retract the outer constraining sheath and allow the stent to expand to its memory diameter. Preferably, the stent will be held fixed relative to the vessel by means of an inner member that engages the stent and is held axially fixed during sheath retraction. The constraining sheath may be designed to retract in a "tip to hub" direction, thereby first expanding and anchoring the end of the stent farthest from the operator. Alternatively, the constraining sheath may be designed to retract from "hub to tip" direction, thereby first expanding and anchoring the end of the stent closest to the operator first. The application of the stent will determine the preferred direction of unsheathing.

After the stent has initially expanded and anchored, it may be advantageous to confirm accurate placement with ultrasound or X-Ray guidance. Further, the stent may contain markers to aid the physician in locating the proximal and distal ends of the stent, as well as any unique features along the length of the stent, or around its circumference. This can be particularly important in denoting the location of stent regions with modulated stiffness or flexibility as described above. Radiopacity enhancing features may include coatings, tabs, rivets, inserts, or other features composed of metals including tantalum, platinum, gold, palladium, silver, or combinations thereof. Alternatively or in addition, it may alsb be advantageous to similarly provide enhanced echogenecity at certain locations of the stent to enhance visualization of selected features during ultrasound diagnostic procedures.

Using visualization techniques, if the placement of the stent is not optimal, the physician may readvance the constraining sheath to recapture the deployed segment of stent, reposition the delivery system, and attempt the deployment again. Although the stent described herein is not necessary a closed-cell design, the ability to recapture the stent is another benefit of the closed cell architecture described above, and is another advantage to connecting all of the internal apices, particularly in the region of the stent that is first expanded. After the stent has been confirmed to be anchored in the intended location, the sheath is fully retracted, releasing the stent from the delivery system into position within the target vessel.

Once the stent has unloaded from its constrained diameter, it will contact the vessel. The chronic outward force of the stent will cause the vessel diameter, particularly at the point of the lesion in some applications, to enlarge to improve patency and/or restore flow through the vessel. As a final step, it can be advantageous to inflate a balloon within the stent, particularly in the region of the subject obstructive lesions. The balloon can assist in expanding the stent, even past its normal expanded diameter. When the balloon is deflated, the stent is again subjected to loading stresses, and therefore resists recoil of the vessel according to the radial resistive force (RRF) driven by the higher stress response of the upper plateau. With this method, the outward forces localized in the area of the obstructive lesion are maximized to ensure maximum luminal gain.

While numerous embodiments of the present invention have been shown and described herein, one of ordinary skill in the art will appreciate that such embodiments are provided by way of example only. Numerous variations, changes, and substitutions will now occur to those skilled in the art without departing from the invention. In addition, the intended uses of the present invention include a variety of medical applications as well as other applications where highly precise, compact devices for fluid transport are needed. It should be understood that various alternatives to these embodiments of the invention described herein may be employed in practicing the invention. It is intended that the following claims defined the scope of the invention and it methods and structures within the scope of these claims and their equivalents be covered thereby.

What is claimed is:

1. A stent comprising:
   a first section and a second section, the second section aligned with the first section along a longitudinal axis of the stent, each section including:
   a plurality of expandable modules, each expandable module including a plurality of strut elements that join together at a plurality of apices in a zig-zag shape,
   wherein a length of each strut element in the first section is 5-50% lower than a length of each strut element in the second section and
   wherein a width of each strut element in the first section is 5-50% higher than a width of each strut element in the second section; and
   a plurality of bridging modules, each bridging module including bridging elements that extend circumferentially and connect each apex of a first expandable module with each apex of a second immediately adjacent expandable module of the plurality of expandable modules,
   wherein a length of each bridging element in the first section is 5-50% shorter than a length of each bridging element in the second section,
   wherein a width of each bridging element in the first section is 5-50% higher than a width of each bridging element in the second section,
   wherein the plurality of bridging modules are arranged to alternate along the longitudinal axis between clockwise bridging modules and counterclockwise bridging modules, the clockwise bridging modules including bridging elements that extend at a clockwise angle with respect to the longitudinal axis, and the counterclockwise bridging modules including bridging elements that extend at a counterclockwise angle with respect to the longitudinal axis;
   wherein the stent is configured to be placed in a vein such that the first section is in a first region of the vein and the second section is in a second region of the vein, the first region subjected to a greater physiologic compression than the second region; and
   wherein the first section is approximately 1.1 to 3 times more radially stiff than the second section such that the first section is configured to withstand the greater physiologic compression of the first region.

2. The stent of claim 1, wherein the physiologic compression is arterial compression.

3. The stent of claim 1, wherein the clockwise bridging modules are configured to counterbalance any rotation caused by the counterclockwise bridging modules.

4. The stent of claim 1, wherein the stent is configured to be placed in an iliac vein, and wherein the first region is a portion of the left common iliac vein where the right common iliac artery crosses the left common iliac vein or a portion of the left external iliac vein where the left internal iliac artery crosses the left external iliac vein.

5. The stent of claim 1, wherein the first section has an axial length of between approximately 1 cm and 3 cm.

6. The stent of claim 5, wherein the axial length is approximately 2 cm.

7. The stent of claim 1, wherein the second section has an axial length of between approximately 4 cm and 10 cm.

8. The stent of claim 7, wherein the axial length is approximately 7 cm.

9. The stent of claim 1, wherein the first section has a radial stiffness that is approximately 2 times the radial stiffness of the second section.

10. The stent of claim 1, wherein the length of each strut element in the first section or in the second section is between approximately 1 mm and 4 mm.

11. The stent of claim 10, wherein the length of each strut element in the first section is approximately 2.1 mm, and wherein the length of each strut element in the second section is approximately 2.5 mm.

12. The stent of claim 1, wherein the width of each strut element in the first section or in the second section is between approximately 0.1 mm and 0.3 mm.

13. The stent of claim 12, wherein the width of each strut element in the first section is approximately 0.16 mm, and wherein the width of each strut element in the second section is approximately 0.12 mm.

14. The stent of claim 1, wherein the length of each bridging element in the first section or in the second section is between approximately 1 mm to 10 mm.

15. The stent of claim 14, wherein the length of each bridging element in the first section is approximately 6 mm, and wherein the length of each bridging element in the second section is approximately 7 mm.

16. The stent of claim 1, wherein the width of each bridging element in the first section or in the second section is approximately 0.07 mm to 0.3 mm.

17. The stent of claim 16, wherein the width of each bridging element in the first section is approximately 0.12 mm, and wherein the width of each bridging element in the second section is approximately 0.1 mm.

18. The stent of claim 1, further comprising a third section, the third section adjacent to the second section and located along the longitudinal axis of the stent, wherein the stent is configured to be placed in the vein such that the third section is in a third region of the vein, the third region subjected to a greater physiologic compression than the second region, and wherein the third section is more radially stiff than the second section such that the third section is configured to withstand the greater physiologic compression of the third region.

19. The stent of claim 18, wherein the third section is configured to have an axial length of approximately 1 cm to 3 cm.

20. The stent of claim 19, wherein the axial length is approximately 2 cm.

21. The stent of claim 18, wherein the stent is configured to be placed in the iliac vein, and wherein the first region is a portion of the left common iliac vein where a right common iliac artery crosses the left common iliac vein, and wherein the third region is a portion of the left external iliac vein where the left internal iliac artery crosses the left external iliac vein.

22. The stent of claim 18, further comprising a fourth section located along the longitudinal axis of the stent, the fourth section more flexible than the first and third sections, wherein the stent is configured to be placed in the vein such that the fourth section is in a fourth region of the vein, the fourth region having higher curvature than the first, second, or third sections.

23. The stent of claim 22, wherein the fourth section is configured to have an axial length of approximately 3 cm to 5 cm.

24. The stent of claim 23, wherein the axial length is approximately 4 cm.

25. The stent of claim 22, wherein the stent is configured to be placed in the iliac vein, and wherein the fourth region is a portion of the left common iliac vein where the left common iliac vein approaches or crosses an inguinal ligament.

26. A stent comprising:
a first section and a second section, the second section aligned with the first section along a longitudinal axis of the stent, each section including:
a plurality of expandable modules, each expandable module including a plurality of strut elements that join together at a plurality of apices in a zig-zag shape,
wherein a length of each strut element in the first section is 5-50% higher than a length of each strut element in the second section,
wherein a width of each strut element in the first section is 5-50% lower than a width of each strut element in the second section; and
a plurality of bridging modules, each bridging module including bridging elements that extend circumferentially and connect each apex of a first expandable module with each apex of a second immediately adjacent expandable module of the plurality of expandable modules;
wherein a length of each bridging element in the first section is 5-50% higher than a length of each bridging element in the second section,
wherein a width of each bridging element in the first section is 5-50% lower than a width of each bridging element in the second section,
wherein the plurality of bridging modules are arranged to alternate along the longitudinal axis between clockwise bridging modules and counterclockwise bridging modules, the clockwise bridging modules including bridging elements that extend at a clockwise angle with respect to the longitudinal axis, and the counterclockwise bridging modules including bridging elements that extend at a counterclockwise angle with respect to the longitudinal axis;
wherein the stent is configured to be placed in a vein such that the first section is in a first region of the vein and a second section is in a second region of the vein, the first region having a higher curvature than the second region; and
wherein the first section is approximately 1.1 to 3 times more flexible than the second section such that the first section is configured to withstand the higher curvature of the first region.

27. The stent of claim 26, wherein the first region is an area where the vein crosses a ligament.

28. The stent of claim 26, wherein the clockwise bridging modules are configured to counterbalance any rotation caused by the counterclockwise bridging modules.

29. The stent of claim 26, wherein the stent is configured to be placed in the iliac vein, and wherein the first region is a portion of the left common iliac vein where the left iliac vein approaches or crosses the inguinal ligament.

30. The stent of claim 26, wherein the first section has an axial length of between approximately 3 cm and 5 cm.

31. The stent of claim 30, wherein the axial length is approximately 4 cm.

32. The stent of claim 26, wherein the first section has a flexibility that is approximately 2 times the flexibility of the second section.

33. The stent of claim 26, wherein the length of each strut element in the first section or in the second section is between approximately 1 mm and 4 mm.

34. The stent of claim 33, wherein the length of each strut element in the first section is approximately 3.0 mm, and wherein the length of each strut element in the second section is approximately 2.5 mm.

35. The stent of claim 26, wherein the width of each strut element in the first section or in the second section is between approximately 0.1 mm and 0.3 mm.

36. The stent of claim 35, wherein the width of each strut element in the first section is approximately 0.1 mm, and wherein the width of each strut element in the second section is approximately 0.12 mm.

37. The stent of claim 26, wherein the length of each bridging element in the first section or in the second section is between approximately 1 mm and 10 mm.

38. The stent of claim 37, wherein the length of each bridging element in the first section is approximately 8 mm, and wherein the length of each bridging element in the second section is approximately 7 mm.

39. The stent of claim 26, wherein the width of each bridging element in the first section or in the second section is approximately 0.07 mm to 0.3 mm.

40. The stent of claim 39, wherein the width of each bridging element in the first section is approximately 0.08 mm, and wherein the width of each bridging element in the second section is approximately 0.1 mm.

41. The stent of claim 26, further comprising a third section, the third section adjacent to the second section and located along the longitudinal axis of the stent, the third section more radially stiff than the first and second sections, wherein the stent is configured to be placed in the vein such that the third section is in a third region of the vein, the third region subjected to higher physiologic compression than the first and second regions.

* * * * *